US011935311B2

(12) United States Patent
Egertson et al.

(10) Patent No.: US 11,935,311 B2
(45) Date of Patent: Mar. 19, 2024

(54) METHODS AND SYSTEMS FOR COMPUTATIONAL DECODING OF BIOLOGICAL, CHEMICAL, AND PHYSICAL ENTITIES

(71) Applicant: Nautilus Subsidiary, Inc., Seattle, WA (US)

(72) Inventors: Jarrett D. Egertson, Rancho Palos Verdes, CA (US); Vadim Lobanov, Seattle, WA (US); David Stern, San Carlos, CA (US); Parag Mallick, San Mateo, CA (US); Sujal M. Patel, Seattle, WA (US); Ryan K. Seghers, Kirkland, WA (US)

(73) Assignee: Nautilus Subsidiary, Inc., Seattle, WA (US)

( * ) Notice: Subject to any disclaimer, the term of this patent is extended or adjusted under 35 U.S.C. 154(b) by 406 days.

(21) Appl. No.: 17/344,769

(22) Filed: Jun. 10, 2021

(65) Prior Publication Data
US 2021/0390705 A1    Dec. 16, 2021

Related U.S. Application Data

(60) Provisional application No. 63/037,747, filed on Jun. 11, 2020.

(51) Int. Cl.
*G06V 20/69* (2022.01)
*C12Q 1/6876* (2018.01)
(Continued)

(52) U.S. Cl.
CPC ........... *G06V 20/69* (2022.01); *C12Q 1/6876* (2013.01); *G01N 21/6428* (2013.01);
(Continued)

(58) Field of Classification Search
CPC ...... G06V 20/69; G06V 10/25; C12Q 1/6876; G01N 21/6428; G01N 2021/6439;
(Continued)

(56) References Cited

U.S. PATENT DOCUMENTS 5,695,934 A    12/1997 Brenner
5,863,722 A    1/1999 Brenner
(Continued)

FOREIGN PATENT DOCUMENTS

WO    WO-2004018497 A2    3/2004
WO    WO-2004018497 A3    6/2004
(Continued)

OTHER PUBLICATIONS

Blatch, et al. The tetratricopeptide repeat: a structural motif mediating protein-protein interactions. Bioessays Nov. 1999;21 (11):932-939.
(Continued)

*Primary Examiner* — Dhaval V Patel
(74) *Attorney, Agent, or Firm* — Morgan, Lewis & Bockius LLP

(57) ABSTRACT

The present disclosure provides systems and methods for detecting components of an array of biological, chemical, or physical entities. In an aspect, the present disclosure provides a method for detecting an array of biological, chemical, or physical entities, comprising: (a) using one or more light sensing devices, acquiring pixel information from sites in an array, wherein the sites comprise biological, chemical, or physical entities that produce light; (b) processing the pixel information to identify a set of regions of interest (ROIs) corresponding to the sites in the array that produce the light; (c) classifying the pixel information for the ROIs into a categorical classification from among a plurality of distinct categorical classifications, thereby producing a plu-
(Continued)

rality of pixel classifications; and (d) identifying one or more components of the array of biological, chemical, or physical entities based at least in part on the plurality of pixel classifications.

26 Claims, 7 Drawing Sheets

(51) Int. Cl.
  *G01N 21/64* (2006.01)
  *G06T 7/00* (2017.01)
  *G06T 7/11* (2017.01)
  *G06V 10/25* (2022.01)
  *G06N 20/00* (2019.01)

(52) U.S. Cl.
  CPC .............. *G06T 7/0012* (2013.01); *G06T 7/11* (2017.01); *G06V 10/25* (2022.01); *G01N 2021/6439* (2013.01); *G06N 20/00* (2019.01); *G06T 2207/20081* (2013.01); *G06T 2207/30072* (2013.01)

(58) Field of Classification Search
  CPC .............. G06T 7/0012; G06T 7/11; G06T 2207/20081; G06T 2207/30072; G06N 20/00
  See application file for complete search history.

(56) References Cited

U.S. PATENT DOCUMENTS

| | | | |
|---|---|---|---|
| 5,888,737 | A | 3/1999 | DuBridge et al. |
| 6,140,489 | A | 10/2000 | Brenner |
| 6,175,002 | B1 | 1/2001 | DuBridge et al. |
| 7,057,026 | B2 | 6/2006 | Barnes et al. |
| 7,211,414 | B2 | 5/2007 | Hardin et al. |
| 7,306,904 | B2 | 12/2007 | Landegren et al. |
| 7,315,019 | B2 | 1/2008 | Turner et al. |
| 7,329,492 | B2 | 2/2008 | Hardin et al. |
| 7,329,860 | B2 | 2/2008 | Feng et al. |
| 7,351,528 | B2 | 4/2008 | Landegren |
| 7,405,281 | B2 | 7/2008 | Xu et al. |
| 7,598,363 | B2 | 10/2009 | Seeman et al. |
| 7,842,793 | B2 | 11/2010 | Rothemund |
| 7,855,054 | B2 | 12/2010 | Schneider et al. |
| 7,964,356 | B2 | 6/2011 | Zichi et al. |
| 8,013,134 | B2 | 9/2011 | Fredriksson |
| 8,222,047 | B2 | 7/2012 | Duffy et al. |
| 8,236,574 | B2 | 8/2012 | Duffy et al. |
| 8,268,554 | B2 | 9/2012 | Schallmeiner |
| 8,404,830 | B2 | 3/2013 | Zichi et al. |
| 8,415,171 | B2 | 4/2013 | Rissin et al. |
| 8,945,830 | B2 | 2/2015 | Heil et al. |
| 8,951,781 | B2 | 2/2015 | Reed et al. |
| 8,975,026 | B2 | 3/2015 | Zichi et al. |
| 8,975,388 | B2 | 3/2015 | Zichi et al. |
| 9,163,056 | B2 | 10/2015 | Rohloff et al. |
| 9,164,053 | B2 | 10/2015 | Collins et al. |
| 9,193,996 | B2 | 11/2015 | Buermann et al. |
| 9,395,359 | B2 | 7/2016 | Walt et al. |
| 9,404,919 | B2 | 8/2016 | Schneider et al. |
| 9,625,469 | B2 | 4/2017 | Marcotte et al. |
| 9,678,012 | B2 | 6/2017 | Rothberg et al. |
| 9,678,068 | B2 | 6/2017 | Duffy et al. |
| 9,777,315 | B2 | 10/2017 | Fredriksson et al. |
| 9,829,456 | B1 | 11/2017 | Jin et al. |
| 9,921,157 | B2 * | 3/2018 | Rothberg ............. C12Q 1/6874 |
| 9,926,566 | B2 | 3/2018 | Ochsner et al. |
| 9,938,314 | B2 | 4/2018 | Rohloff et al. |
| 10,036,064 | B2 | 7/2018 | Merriman et al. |
| 10,221,207 | B2 | 3/2019 | Rohloff et al. |
| 10,221,421 | B2 | 3/2019 | Jarvis et al. |
| 10,239,908 | B2 | 3/2019 | Rohloff et al. |
| 10,316,321 | B2 | 6/2019 | Zichi et al. |
| 10,392,621 | B2 | 8/2019 | Ochsner et al. |
| 10,473,654 | B1 | 11/2019 | Mallick |
| 10,545,153 | B2 | 1/2020 | Marcotte et al. |
| 10,605,730 | B2 | 3/2020 | Rothberg et al. |
| 10,712,274 | B2 | 7/2020 | Rothberg et al. |
| 10,775,305 | B2 | 9/2020 | Rothberg et al. |
| 10,858,703 | B2 | 12/2020 | Buermann et al. |
| 10,895,534 | B2 | 1/2021 | Finkelstein et al. |
| 2007/0007991 | A1 | 1/2007 | Lee et al. |
| 2008/0108082 | A1 | 5/2008 | Rank et al. |
| 2008/0170240 | A1 * | 7/2008 | Yamazoe ............. G03F 7/70725 356/620 |
| 2009/0026082 | A1 | 1/2009 | Rothberg et al. |
| 2009/0127589 | A1 | 5/2009 | Rothberg et al. |
| 2009/0247414 | A1 | 10/2009 | Obradovic et al. |
| 2010/0111768 | A1 | 5/2010 | Banerjee et al. |
| 2010/0137143 | A1 | 6/2010 | Rothberg et al. |
| 2010/0208955 | A1 | 8/2010 | Mehes et al. |
| 2010/0282617 | A1 | 11/2010 | Rothberg et al. |
| 2017/0240962 | A1 | 8/2017 | Merriman et al. |
| 2018/0051316 | A1 | 2/2018 | Collins et al. |
| 2018/0112265 | A1 | 4/2018 | Boyanov et al. |
| 2018/0155773 | A1 | 6/2018 | Gunderson et al. |
| 2018/0305727 | A1 | 10/2018 | Merriman et al. |
| 2019/0145982 | A1 | 5/2019 | Chee et al. |
| 2020/0082914 | A1 | 3/2020 | Patel et al. |
| 2020/0090785 | A1 | 3/2020 | Patel et al. |
| 2020/0173988 | A1 | 6/2020 | Mallick |
| 2020/0348307 | A1 | 11/2020 | Beierle et al. |
| 2020/0348308 | A1 | 11/2020 | Chee et al. |
| 2021/0101930 | A1 | 4/2021 | Gremyachinskiy et al. |
| 2021/0181086 | A1 * | 6/2021 | Chou ................. G01N 15/1484 |
| 2021/0239705 | A1 | 8/2021 | Mallick |

FOREIGN PATENT DOCUMENTS

| | | |
|---|---|---|
| WO | WO-2007123744 A2 | 11/2007 |
| WO | WO-2007123744 A3 | 11/2008 |
| WO | WO 2019/195633 A1 | 10/2019 |
| WO | WO 2019/236749 A3 | 12/2019 |
| WO | WO-2019236749 A2 | 12/2019 |
| WO | WO-2020223368 A1 | 11/2020 |
| WO | WO-2021087402 A1 | 5/2021 |

OTHER PUBLICATIONS

Capitán-Vallvey, et al. Recent developments in computer vision-based analytical chemistry: A tutorial review. Analytica chimica acta vol. 899 (2015): 23-56. doi:10.1016/j.aca.2015.10.009.

Chang, et al. Micro-sequence analysis of peptides and proteins using 4-NN-dimethylaminoazobenzene 4'-isothiocyanate/ phenylisothiocyanate double coupling method. FEBS Letters 93 (1978).

Duarte, et al. Single-pixel imaging via compressive sampling. IEEE Signal Processing Magazine. 2008; 25(2):83-91.

Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

Matula, et al. Single-cell-based image analysis of high-throughput cell array screens for quantification of viral infection. Cytometry. Part A: the journal of the International Society for Analytical Cytology vol. 75,4 (2009): 309-18. doi:10.1002/cyto.a.20662.

McKay, et al. Click Chemistry in Complex Mixtures: Bioorthogonal Bioconjugation. Chem Biol. Sep. 18, 2014; 21(9): 1075-1101.

Meldal, et al. Cu-catalyzed azide-alkyne cycloaddition. Chem Rev. Aug. 2008; 108(8):2952-3015. doi: 10.1021/cr0783479.

Newkome, et al. Poly(amidoamine), polypropylenimine, and related dendrimers and dendrons possessing different 1 → 2 branching motifs: An overview of the divergent procedures. Polymer 49 (2008): 1-173.

PCT/US21/036874 International Search Report and Written Opinion dated Oct. 1, 2021.

(56) References Cited

OTHER PUBLICATIONS

Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio. 5b00415. Epub Jul. 17, 2015.

Spicer et al. Achieving Controlled Biomolecule-Biomaterial Conjugation. Chemical reviews vol. 118, 16 (2018): 7702-7743.

Stohr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.

Swaminathan, J. et al. Highly parallel single-molecule identification of proteins in zeptomole-scale mixtures. Nature biotechnology, 10.1038/nbt.4278. Oct. 22, 2018, doi: 10.1038/nbt.4278.

* cited by examiner

METHODS AND SYSTEMS FOR COMPUTATIONAL DECODING OF BIOLOGICAL, CHEMICAL, AND PHYSICAL ENTITIES

CROSS-REFERENCE

This application claims the benefit of U.S. Provisional Patent Application No. 63/037,747, filed Jun. 11, 2020, which is incorporated by reference herein in its entirety.

BACKGROUND

Biological assays may be used for applications such as genome sequencing or protein expression. It may be beneficial to tailor the design of biological assays for the fast, high-confidence identification of a large number of small amounts of different biological, chemical, and/or physical entities. However, such requirements may introduce challenges in the form of competing constraints on the arrays, chips, liquid handling system (e.g., microfluidic devices), flow cells, sample preparation instrumentation, and detection systems (e.g., computational systems) used for such assays. For example, the large number of objects (e.g., entities or analytes) to be detected may impose constraints on the amount of material that can be used for each object, the density at which these objects can be loaded on a substrate of reasonable size, and the complexity of instrumentation and software that is used to assay samples to acquire data and/or to decode biological, chemical, and physical entities based on the acquired data.

SUMMARY

The present disclosure provides methods and systems for detecting components of an array of biological, chemical, or physical entities. Using particular configurations of the disclosed methods and systems, arrays of biological, chemical, or physical entities can be detected while achieving advantages such as: a reduction in the scanning time required by performing parallel imaging without moving parts during imaging, a reduction in noise levels by reducing the number of components in the imaging system, an improved resolution arising from efficiently detecting one or more objects using sensors, decreased crosstalk between neighboring object signals, improved detection sensitivity arising from improved imaging sensors, and improved detection specificity arising from accurate identification of emission signals corresponding to locations of biological, chemical, or physical entities.

In an aspect, the present disclosure provides a method for detecting one or more components of an array of biological, chemical, or physical entities, comprising: (a) subjecting the array of biological, chemical, or physical entities to a plurality of binding agents, wherein each of the plurality of binding agents is configured to selectively bind to at least a portion of the array of biological, chemical, or physical entities; (b) exposing the array of biological, chemical, or physical entities to electromagnetic radiation sufficient to excite the array, thereby producing an emission signal of the array; (c) using one or more light sensing devices, acquiring a plurality of pixel information of the emission signal of the array; (d) classifying each of the plurality of pixel information into a categorical classification from among a plurality of distinct categorical classifications, thereby producing a plurality of pixel classifications; and (e) detecting one or more components of the array of biological, chemical, or physical entities based at least in part on the pixel classifications. In some embodiments, (d) further comprises processing the plurality of pixel information to identify a set of regions of interest (ROIs) corresponding to a potential location of a biological, chemical, or physical entity from among the array of biological, chemical, or physical entities. In some embodiments, each of the set of ROIs comprises pixel information corresponding to a single cluster of pixels. In some embodiments, (d) further comprises applying a classifier to the set of ROIs to classify each of the plurality of pixel information into the categorical classification.

In some embodiments, an individual site in the array of biological, chemical, or physical entities comprises a biological, chemical, or physical entity selected from the group consisting of: (i) a single structured nucleic acid particle (SNAP); (ii) a single SNAP with at least one fluorescent label; (iii) a DNA origami; (iv) a DNA origami with at least one fluorescent label; (v) a single protein; (vi) a single protein bound to a single SNAP; (vii) a single protein bound to a single DNA origami; (viii) one or more fluorescent labels bound to a biological, chemical, or physical entity of (i)-(vii); (ix) one or more nanoparticles; (x) one or more optically active nanoparticles; (xi) one or more formulations of dendrimers; and (xii) a combination thereof. In some embodiments, the single protein comprises an antibody, an antigen, a peptide, or an aptamer. In some embodiments, each of the plurality of binding agents is configured to selectively bind to SNAP-protein complexes of the array of biological, chemical, or physical entities. In some embodiments, the one or more nanoparticles comprise organic, inorganic, or biological nanoparticles. In some embodiments, the one or more optically active nanoparticles comprise quantum dots.

In some embodiments, an imaging system comprises the one or more light sensing devices. The imaging system may be separate from the array, and comprise a movable stage (e.g., a microscope stage) configured to move the array of biological, chemical, or physical entities relative to the one or more light sensing devices. In some embodiments, the movement may comprise movement in an XY plane and/or movement in a Z plane. For example, the one or more light sensing devices may comprise cameras or other image sensors, such as charge coupled device (CCD) sensors, complementary metal-oxide-semiconductor (CMOS) sensors, charge injection device (CID) sensors, or JOT image sensors (Quanta).

Alternatively, the imaging system may comprise a substrate that is integrated (e.g., physically coupled) to the one or more light sensing devices. Methods of integrating light sensing devices with an array of biological, chemical, or physical entities may be described by, for example, international PCT patent application No. PCT/US2020/030501, which is incorporated by reference herein in its entirety. In some embodiments, the one or more light sensing devices comprises one or more device features selected from the group consisting of: (i) a surface coating to promote adhesion of specific biological, chemical, or physical entities; (ii) a surface coating to prevent nonspecific binding of specific biological, chemical, or physical entities; (iii) a differential surface coating to promote binding of a first type of biological, chemical, or physical entities in some locations and to prevent non-specific binding in other locations; (iv) a single-layer surface coating; (v) a multiple-layer surface coating; (vi) a surface coating deposited by atomic layer deposition (ALD), molecular layer deposition (MLD), chemical layer deposition (CVD), physical layer deposition (PLD); (vii) a surface coating patterned by lithography and/or etching processes; (viii) a surface coating with one or more optical properties; (ix) a compartment of each pixel with nanowell-like structures to prevent cross-talk; (x) a compartment of each pixel with nanowell-like structures to increase fluorescent light collection; and (xi) a combination thereof. In some embodiments, the surface coating comprises $ZrO_2$, silane, or thiols. In some embodiments, the surface coating comprises phosphate, phosphonate, polyethylene glycol (PEG)-silane, or PEG-thiols. In some embodiments, the PLD is evaporation, spin coating, dipping, or a combination thereof. In some embodiments, the one or more optical properties comprise bandpass filters, polarization filters, anti-reflection, fluorescent, or reflective coatings. In some embodiments, the nanowell-like structures have opaque walls. In some embodiments, the nanowell-like structures have photo-sensitive walls.

In some embodiments, the one or more light sensing devices comprise one or more flow cells. In some embodiments, the one or more flow cells are fabricated directly on top of the one or more light sensing pixels.

In some embodiments, the one or more light sensing devices comprise one or more instruments selected from the group consisting of: (i) an instrument configured for detection of an array of immobilized biological, chemical, or physical entities by scanning a detector of the instrument; (ii) an instrument configured for detection of an array of immobilized biological, chemical, or physical entities without scanning a detector of the instrument; (iii) an instrument configured for detection of an array of immobilized biological, chemical, or physical entities without any lens of a detector of the instrument; (iv) an instrument configured for detection of an array of immobilized biological, chemical, or physical entities without a focusing mechanism of a detector of the instrument; (v) an instrument configured for parallel excitation of immobilized fluorescent markers; and (vi) a combination thereof. In some embodiments, the instrument is configured to use four-beam interference to create a two-dimensional sine wave pattern.

In some embodiments, the one or more light sensing devices comprise a material compatible with complementary metal-oxide semiconductor (CMOS) processing, and the one or more light sensing devices are configured to be functionalized.

In some embodiments, the one or more light sensing devices are fabricated using one or more process steps selected from the group consisting of: (i) differential functionalization of an active surface of the array of light sensing devices; (ii) integration of nanowells to prevent cross-talk; (iii) integration of nanowells to increase light collection; (iv) assembly of flow cell directly on array of light sensing devices; and (v) a combination thereof.

In some embodiments, the one or more light sensing devices comprises an array of light sensing devices, wherein a dimension and/or pitch of individual devices of the array of light sensing devices is matched to a dimension and/or pitch of individual entities of the array of biological, chemical, or physical entities.

In some embodiments, the one or more light sensing devices comprise a coating comprising materials selected from the group consisting of: a metal; a metal oxide; and a metal nitride. In some embodiments, the metal is gold. In some embodiments, the metal oxide is $ZrO_2$. In some embodiments, the metal nitride is TiN.

In some embodiments, the one or more light sensing devices comprise a surface chemistry selected from the group consisting of: silanes; phosphates; phosphonates; and thiols. In some embodiments, the silanes comprise (3-Aminopropyl)triethoxysilane (APTES). In some embodiments, the phosphonates comprises (Aminomethyl)phosphonic acid or free phosphate. In some embodiments, the thiols comprise Thiol-PEG-Amine or mPEG-Thiol.

In some embodiments, individual devices of the one or more light sensing devices are surrounded by a microwell or nanowell to prevent crosstalk between the individual devices and/or to increase light collection.

In some embodiments, the classifier comprises a trained machine learning classifier. In some embodiments, the trained machine learning classifier comprises a supervised machine learning algorithm. In some embodiments, the supervised machine learning algorithm comprises a support vector machine (SVM), a linear regression, a logistic regression, a nonlinear regression, a neural network, a Random Forest, a deep learning algorithm, a naïve Bayes classifier, or a combination thereof. In some embodiments, the trained machine learning classifier comprises an unsupervised machine learning algorithm. In some embodiments, the unsupervised machine learning algorithm comprises clustering analysis (e.g., k-means clustering, hierarchical clustering, mixture models, DBSCAN, OPTICS algorithm), principal component analysis, independent component analysis, non-negative matrix factorization, singular value decomposition, anomaly detection (e.g., local outlier factor), neural network (e.g., autoencoder, deep belief network, Hebbian learning, generative adversarial network, self-organizing map), expectation-maximization algorithm, method of moments, or a combination thereof.

In some embodiments, the plurality of distinct categorical classifications comprises a first categorical classification associated with an emission signal of the array indicative of a potential presence of a biological, chemical, or physical entity, and a second categorical classification associated with an emission signal of the array indicative of a potential absence of a biological, chemical, or physical entity. In some embodiments, the first categorical classification is indicative of a potential presence of a SNAP-protein complex. In some embodiments, the first categorical classification is indicative of a likelihood of the presence of the SNAP-protein complex that is at least a first pre-determined threshold. In some embodiments, the first pre-determined threshold is at least about 50%, 55%, 60%, 65%, 70%, 75%, 80%, 85%, 90%, 95%, 96%, 97%, 98%, or 99%. In some embodiments, the second categorical classification is indicative of a potential absence of a SNAP-protein complex. In some embodiments, the second categorical classification is indicative of a likelihood of the presence of the SNAP-protein complex that is less than a second pre-determined threshold. In some embodiments, the second pre-determined threshold is at least about 50%, 45%, 40%, 35%, 30%, 25%, 20%, 15%, 10%, 5%, 4%, 3%, 2%, or 1%. In some embodiments, detecting the one or more components of the array of biological, chemical, or physical entities comprises identifying a presence or an absence of one or more proteins or peptides among the or more components of the array of biological, chemical, or physical entities. In some embodiments, detecting the one or more components of the array of biological, chemical, or physical entities comprises identifying a presence or an absence of one or more proteins among the or more components of the array of biological, chemical, or physical entities. In some embodiments, detecting the one or more components of the array of biological, chemical, or physical entities comprises identifying a presence or an absence of one or more peptides among the or more components of the array of biological, chemical, or physical entities. In some embodiments, the method further comprises identifying an abundance of the one or more proteins or peptides. In some embodiments, the abundance of the one or more proteins or peptides comprises a differential protein or peptide abundance, a relative protein or peptide abundance, an absolute protein or peptide abundance, or a combination thereof.

In another aspect, the present disclosure provides a system for detecting one or more components of an array of biological, chemical, or physical entities, comprising: (a) an array of biological, chemical, or physical entities, wherein the array of biological, chemical, or physical entities is configured to produce an emission signal upon exposure to electromagnetic radiation sufficient to excite the array; (b) one or more light sensing devices configured to acquire a plurality of pixel information of the emission signal of the array; and (c) a non-transitory computer-readable storage medium comprising machine-executable code that, upon execution by one or more computer processors, implements a method for detecting one or more components of an array of biological, chemical, or physical entities, the method comprising: (i) using the one or more light sensing devices, acquiring a plurality of pixel information of the array, (ii) classifying each of the plurality of pixel information into a categorical classification from among a plurality of distinct categorical classifications, thereby producing a plurality of pixel classifications, and (iii) detecting one or more components of the array of biological, chemical, or physical entities based at least in part on the plurality of pixel classifications.

In another aspect, the present disclosure provides a non-transitory computer-readable medium comprising machine-executable code that, upon execution by one or more computer processors, implements a method for detecting one or more components of an array of biological, chemical, or physical entities, the method comprising: obtaining the array of biological, chemical, or physical entities, wherein the array is configured to produce an emission signal upon exposure to electromagnetic radiation sufficient to excite the array; using one or more light sensing devices configured to acquire a plurality of pixel information of the emission signal of the array, acquiring a plurality of pixel information of the array; classifying each of the plurality of pixel information into a categorical classification from among a plurality of distinct categorical classifications, thereby producing a plurality of pixel classifications; and detecting one or more components of the array of biological, chemical, or physical entities based at least in part on the pixel classifications.

Another aspect of the present disclosure provides a non-transitory computer-readable medium comprising machine-executable code that, upon execution by one or more computer processors, implements any of the methods above or elsewhere herein.

Another aspect of the present disclosure provides a system comprising one or more computer processors and computer memory coupled thereto. The computer memory comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the methods and apparatus of the present disclosure are capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
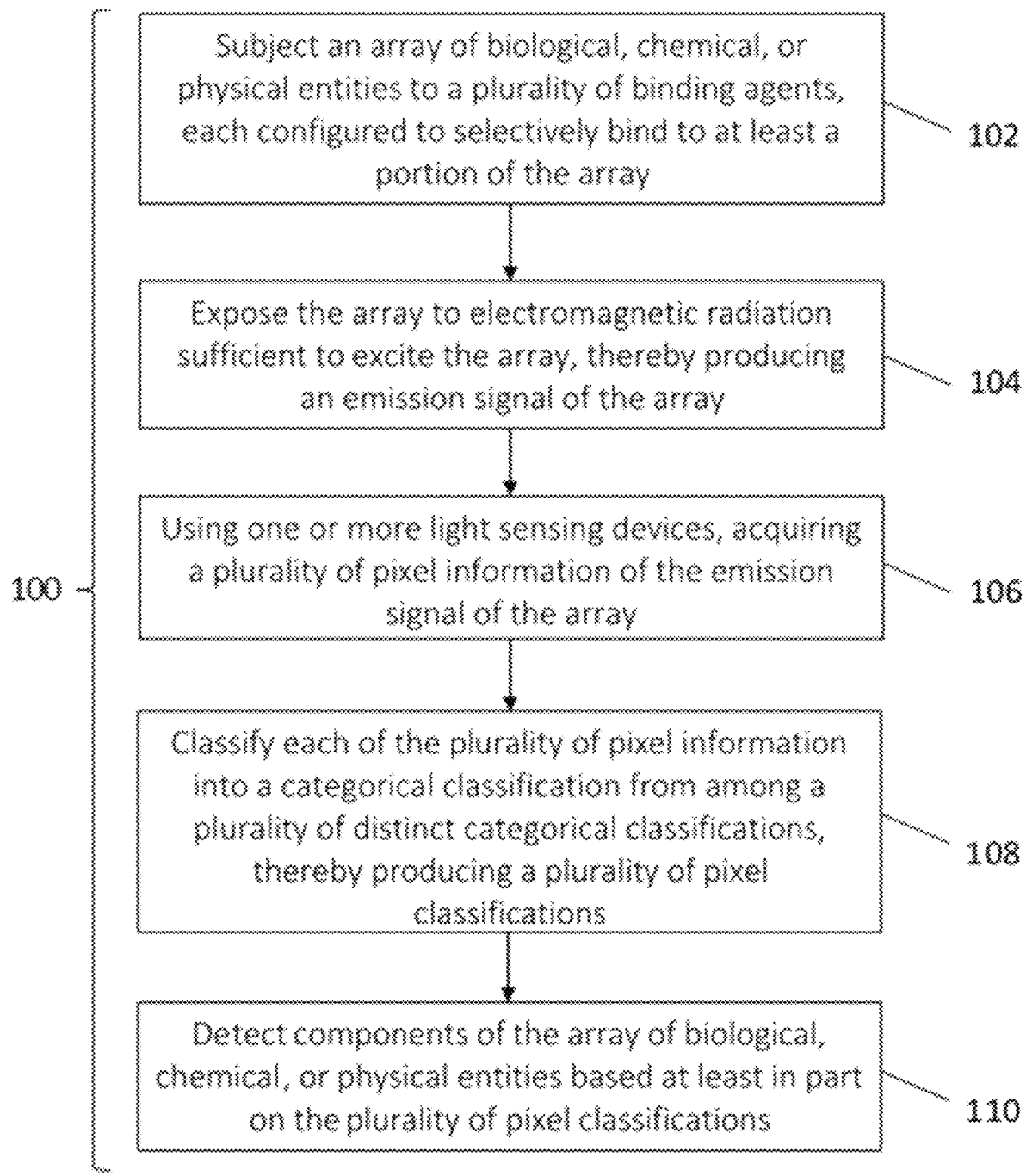
FIG. 1 illustrates an example workflow of a method for detecting components of an array of biological, chemical, or physical entities.

Biological assays may be used for applications such as genome sequencing or determining protein abundance. It may be beneficial to tailor the design of biological assays for the fast, high-confidence identification of a large number of small amounts of different biological, chemical, and/or physical entities. However, such requirements may introduce challenges in the form of competing constraints on the arrays, chips, liquid handling system (e.g., microfluidic devices), flow cells, sample preparation instrumentation, and detection systems (e.g., computational systems) used for such assays. For example, the large number of objects to be detected may impose constraints on the amount of material that can be used for each object, the density at which these objects can be loaded on a substrate of reasonable size, and the complexity of instrumentation and software that is used to assay samples to acquire data and/or to decode biological, chemical, and physical entities based on the acquired data.

The present disclosure provides methods and systems for detecting components of an array of biological, chemical, or physical entities. Using disclosed methods and systems, arrays of biological, chemical, or physical entities can be detected while achieving advantages such as: a reduction in the scanning time required by performing parallel imaging without moving parts during imaging, a reduction in noise levels by reducing the number of components in the imaging system, an improved resolution arising from efficiently detecting object signals using sensors, decreased crosstalk between neighboring object signals, improved detection sensitivity arising from improved imaging sensors, or improved detection specificity arising from accurate identification of emission signals corresponding to locations of biological, chemical, or physical entities. One or more of these advantages may be provided by particular embodiments or configurations of the methods and systems set forth herein.

Terms used herein will be understood to take on their ordinary meaning in the relevant art unless specified otherwise. Several terms used herein and their meanings are set forth below.

As used herein, the term "affinity agent" refers to a molecule or other substance that is capable of specifically or reproducibly binding to an analyte, binding partner or other entity. Binding can optionally be used to identify, track, capture, alter, or influence the entity. The entity can optionally be larger than, smaller than or the same size as the affinity agent. An affinity agent may form a reversible or irreversible interaction with an entity such as an analyte or binding partner. An affinity agent may bind with an entity in a covalent or non-covalent manner. An affinity agent may be configured to perform a chemical modification (e.g., ligation, cleavage, concatenation, etc.) that produces a detectable change in the analyte, binding partner or other entity, thereby permitting observation of the interaction that occurred. Affinity agents may include reactive affinity agents or catalytic affinity reagents (e.g., kinases, ligases, proteases, nucleases, etc.) or non-reactive affinity agents (e.g., antibodies, antibody fragments, aptamers, DARPins, peptamers, etc.). An affinity agent may include one or more known and/or characterized binding components or binding sites (e.g., complementarity-defining regions) that mediate or facilitate binding with a binding partner. Accordingly, an affinity agent can be monovalent or multivalent (e.g., bivalent, trivalent, tetravalent, etc.). An affinity agent may be non-reactive and non-catalytic, thereby not permanently altering the chemical structure of a substance to which it binds in a method set forth herein. The terms "binding agent," "binding reagent," and "affinity reagent" are used herein synonymously with the term "affinity agent."

As used herein, the term "analyte" refers to an entity or substance that is to be detected, identified, located, characterized or measured; that is detected, identified, located, characterized or measured; or that is being detected, identified, located, characterized or measured. An analyte can be a probe (e.g., an affinity agent) or target (e.g., an entity that binds an affinity reagent) depending upon the context and perspective in which the term is used. Exemplary analytes include, but are not limited to, proteins, polypeptides, peptides, antibodies, amino acids, nucleic acids (e.g., DNA, RNA or analogs thereof), oligonucleotides, nucleotides, polysaccharides, oligosaccharides, sugars, enzyme cofactors, metabolites, particles, biological cells, subcellular components, organelles and the like.

As used herein, the term "array" refers to a population of entities that are attached to one or more solid supports such that an entity at one site can be distinguished from entities at other sites. The attachment can be covalent or non-covalent (e.g., ionic bond, hydrogen bond, van Der Waals forces etc.). An array can include different entities that are each located at different sites on a solid support. Alternatively, an array can include separate solid supports each functioning as an site that bears a different entity, wherein the different entities can be identified according to the locations of the solid supports on a surface to which the solid supports are attached, or according to the locations of the solid supports in a liquid such as a fluid stream. The entities of the array can be, for example, molecules, nucleic acids such as SNAPs, polypeptides, proteins, peptides, oligopeptides, enzymes, ligands, or receptors such as antibodies, functional fragments of antibodies or aptamers. The sites of an array can optionally be optically observable and, in some configurations, adjacent sites can be optically distinguishable when detected using a method or apparatus set forth herein.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "epitope" generally refers to an affinity target within a protein, polypeptide or other molecule. Epitopes may comprise amino acid sequences that are sequentially adjacent in the primary structure of a protein or amino acids that are structurally adjacent in the secondary, tertiary or quaternary structure of a protein. An epitope can optionally be recognized by or bound to an antibody. In other configurations of the compositions and methods set forth herein an epitope need not necessarily be recognized by any antibody, for example, instead being recognized by an aptamer or other binding agent. An epitope can optionally bind an antibody to elicit an immune response. In other configurations of the compositions and methods set forth herein an epitope need not necessarily participate in eliciting an immune response.

As used herein, the term "nucleic acid nanoball" generally refers to a globular or spherical nucleic acid structure. A nucleic acid nanoball may comprise a concatemer of oligonucleotides that arranges in a globular structure. A nucleic acid nanoball may include DNA, RNA, PNA, modified or non-natural nucleic acids, or combinations thereof.

As used herein, the term "nucleic acid origami" generally refers to a nucleic acid construct comprising an engineered tertiary (e.g., folding and relative orientation of secondary structures) or quaternary structure (e.g., hybridization between strands that are not covalently linked to each other) in addition to the naturally-occurring secondary structure (e.g., helical structure) of nucleic acid(s). A nucleic acid origami may include DNA, RNA, PNA, modified or non-natural nucleic acids, or combinations thereof. A nucleic acid origami can include a scaffold strand. The scaffold strand can be circular (i.e., lacking a 5' end and 3' end) or linear (i.e., having a 5' end and/or a 3' end). A nucleic acid origami may include a plurality of oligonucleotides that hybridize via sequence complementarity to produce the engineered structuring of the origami particle. For example, the oligonucleotides can hybridize to a scaffold strand and/or to other oligonucleotides. A nucleic acid origami may comprise sections of single-stranded or double-stranded nucleic acid, or combinations thereof. Exemplary nucleic acid origami structures may include nanotubes, nanowires, cages, tiles, nanospheres, blocks, and combinations thereof.

As used herein, the term "protein" generally refers to a molecule comprising two or more amino acids joined by a peptide bond. A protein may also be referred to as a polypeptide or a peptide. A protein can be a naturally-occurring molecule, or an artificial or synthetic molecule. A protein may include one or more non-natural, modified amino acids, or non-amino acid linkers. A protein may contain D-amino acid enantiomers, L-amino acid enantiomers or both. A protein may be modified naturally or synthetically, such as by post-translational modifications.

As used herein, the term "single-analyte" generally refers to a chemical entity that is individually manipulated or distinguished from other chemical entities. A single-analyte may possess a distinguishing property such as volume, surface area, diameter, electrical charge, electrical field, magnetic field, electronic structure, electromagnetic absorbance, electromagnetic transmittance, electromagnetic emission, radioactivity, atomic structure, molecular structure, crystalline structure, or a combination thereof. The distinguishing property of a single-analyte may be a property of the single-analyte that is detectable by a detection method that possesses sufficient spatial resolution to detect the individual single-analyte from any adjacent single-analytes. The distinguishing property of a single-analyte may be a unique combination of properties, whether or not the individual properties that make up the combination are unique. A single-analyte may be a single-molecule (e.g., single-protein or single-SNAP), a single-complex of molecules (e.g., single-SNAP-protein complex), a single-particle, or a single-chemical-entity comprising multiple conjugated molecules or particles. A single-analyte may be distinguished based on spatial or temporal separation from other analytes, for example, in a system or method set forth herein. Moreover, reference herein to a 'single-analyte' in the context of a composition, system or method does not necessarily exclude application of the composition, system or method to multiple single-analytes that are manipulated or distinguished individually, unless indicated contextually or explicitly to the contrary.

As used herein, the term "site," when used in reference to an array, generally refers to a location in an array where a particular entity is present. A site can contain only a single-entity, or it can contain a population of several entities of the same species (i.e., an ensemble of the entities). Alternatively, a site can include a population of entities that are different species. Sites of an array may be discrete. The discrete sites can be contiguous, or they can have interstitial spaces between each other. An array useful herein can have, for example, sites that are separated by less than 100 microns, 50 microns, 10 microns, 5 microns, 1 micron, or 0.5 micron. Alternatively or additionally, an array can have sites that are separated by at least 0.5 micron, 1 micron, 5 microns, 10 microns, 50 microns or 100 microns. The sites can each have an area of less than 1 square millimeter, 500 square microns, 100 square microns, 25 square microns, 1 square micron or less.

As used herein, the term "solid support" (also referred to herein as "substrate") generally refers to a material that is insoluble in aqueous liquid. Optionally, the material can be rigid. The material can be non-porous or porous. The material can optionally be capable of taking up a liquid (e.g., due to porosity) and can, but not necessarily, be sufficiently rigid that the material does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, gels, and polymers.

As used herein, the term "structured nucleic acid particle" (or "SNAP") generally refers to a single- or multi-chain polynucleotide molecule having a compacted three-dimensional structure. The compacted three-dimensional structure can optionally have a characteristic tertiary structure. For example, a SNAP can be configured to have an increased number of interactions between regions of a polynucleotide strand, less distance between the regions, increased number of bends in the strand, and/or more acute bends in the strand, as compared to the same nucleic acid molecule in a random coil or other non-structured state. Alternatively or additionally, the compacted three-dimensional structure can optionally have a characteristic quaternary structure. For example, a SNAP can be configured to have an increased number of interactions between polynucleotide strands or less distance between the strands, as compared to the same nucleic acid molecule in a random coil or other non-structured state. In some configurations, the secondary structure (i.e., the helical twist or direction of the polynucleotide strand) of a SNAP can be configured to be more dense than the same nucleic acid molecule in a random coil or other non-structured state. SNAPs may include deoxyribonucleic acid (DNA), ribonucleic acid (RNA), peptide nucleic acid (PNA), and combinations thereof. SNAPs may have naturally-arising or engineered secondary, tertiary, or quaternary structures. Exemplary SNAPs may include nucleic acid nanoballs (e.g., DNA nanoballs), nucleic acid nanotubes (e.g., DNA nanotubes), and nucleic acid origami (e.g., DNA origami). A SNAP may be functionalized to include one or more reactive handles or other moieties.

Referring to FIG. 1, in an aspect, the present disclosure provides a method 100 for detecting components of an array of biological, chemical, or physical entities. The method 100 may comprise subjecting the array of biological, chemical, or physical entities to a plurality of binding agents (as in operation 102). In some embodiments, each of the plurality of binding agents is configured to selectively bind to at least a portion of the array of biological, chemical, or physical entities. Next, the method 100 may comprise exposing the array of biological, chemical, or physical entities to electromagnetic radiation sufficient to excite the array, thereby producing an emission signal of the array (as in operation 102). Next, the method 100 may comprise using one or more light sensing devices, acquiring a plurality of pixel information of the emission signal of the array (as in operation 104). Next, the method 100 may comprise classifying each of the plurality of pixel information into a categorical classification from among a plurality of distinct categorical classifications, thereby producing a plurality of pixel classifications (as in operation 106). Next, the method 100 may comprise detecting one or more components of the array of biological, chemical, or physical entities based at least in part on the plurality of pixel classifications (as in operation 108). The method set forth in FIG. 1 is exemplary. In various embodiments, modifications can be made. For example, operation 102 can be modified such that one or more reagents is contacted with the array, the reagent(s) reacting with one or more of the biological, chemical, or physical entities to produce an emission signal or other detectable signal. Alternatively or additionally, operation 104 can be modified to detect a signal other than an emission signal. For example, a label or probe other than a luminophore can be used. Labels and probes that produce optical signals other than luminescence emission, or that produce non-optical signals, are set forth herein.

Methods and systems of the present disclosure may comprise, or may be configured to allow, immobilization of one or more biological, chemical, or physical entities at one or more sites of an array. For example, the sites can be aligned with at least one pixel of a set of one or more light sensor devices (e.g., a light sensor array). Alignment of sites to pixels can be achieved through space, for example, by relative motion between the array and an objective of the detection system. Alternatively, sites can be physically aligned to pixels by integrating the array with one or more components of a detection system. Exemplary biological, chemical, or physical entities that can be present at one or more sites of an array may be selected from: (i) a single-structured nucleic acid particle (SNAP); (ii) a single-SNAP with at least one fluorescent label; (iii) a nucleic acid origami (e.g., DNA or RNA origami); (iv) a nucleic acid origami (e.g., DNA or RNA origami) attached (covalently or non-covalently) to at least one fluorescent label; (v) a single-protein (antibody, antigen, peptide, aptamer, or other protein); (vi) a single-protein (antibody, antigen, peptide, aptamer, or other proteins) attached (covalently or non-covalently) to a single-SNAP; (vii) a single-protein (antibody, antigen, peptide, aptamer, or other proteins) attached (covalently or non-covalently) to a single-nucleic acid origami (e.g., DNA or RNA origami); (viii) one or more fluorescent labels attached (covalently or non-covalently) to a biological, chemical, or physical entity of (i)-(vii); (ix) one or more nanoparticles (e.g., organic, inorganic, or biological); (x) one or more nanoparticles with optical properties (e.g., quantum dots); (xi) one or more formulations of dendrimers; and (xii) a combination thereof. In some embodiments, a SNAP is configured to attach to one or more proteins or peptides. In some embodiments, a SNAP is configured to attach to one protein or peptide. In some embodiments, a SNAP is configured to attach to two proteins or peptides. In some embodiments, a SNAP is configured to attach to three or more proteins or peptides.

Methods and systems of the present disclosure may comprise one or more flow cells. For example, the one or more flow cells may comprise a flow cell fabricated to be in direct contact with an array of light sensing pixels. For example, a flow cell can be fabricated directly on top of an array of light sensing pixels.

Methods and systems of the present disclosure may comprise one or more instruments. For example, the one or more instruments may be selected from: (i) an instrument configured for detection of an array of immobilized biological, chemical, or physical entity without scanning a detector of the instrument; (ii) an instrument configured for detection of an array of immobilized biological, chemical, or physical entities without any lens of a detector of the instrument; (iii) an instrument configured for detection of an array of immobilized biological, chemical, or physical entities without a focusing mechanism of a detector of the instrument; (iv) an instrument configured for parallel excitation of immobilized fluorescent markers (e.g., configured to use four-beam interference to create a two-dimensional sine wave pattern); and (v) a combination thereof.

As an example, methods and systems of the present disclosure may comprise immobilization of SNAPs on an array of functionalized sites, each site having a 300 nm diameter and the pitch being 1.625-µm for the sites in the array. The dimensions of the functionalized sites and/or the pitch may be chosen, for example, to be close to the dimensions of suitable image sensing arrays (e.g., commercially available image sensing arrays). In some embodiments, surfaces of sensing arrays are able to be functionalized because they are made of material compatible with complementary metal-oxide semiconductor (CMOS) processing.

Methods and systems of the present disclosure may comprise one or more process steps. For example, the one or more process steps may be selected from: (i) differential functionalization of an active surface of the array of light sensing devices; (ii) integration of nanowells to prevent cross-talk; (iii) integration of nanowells to increase light collection; (iv) assembly of a flow cell directly on array of light sensing devices; and (v) a combination thereof.

In some instances it may be desirable to produce a microarray or nanoarray wherein a plurality of biological, chemical, or physical entities are spatially distributed over and stably associated with the surface of a solid support such that each individual biological, chemical, or physical entity is spatially separated from each other biological, chemical, or physical entity.

In some embodiments, this disclosure provides methods of producing an array of spatially separated biological, chemical, or physical entities, a method may comprise: obtaining a solid support with attachment sites, obtaining a sample comprising biological, chemical, or physical entities, obtaining seeds, each with a functional group, covalently attaching each biological, chemical, or physical entity to a single seed via the functional group, growing each attached seed to one or more SNAPs of desired size, and attaching the SNAPs to the attachment sites of the array, thereby producing an array (e.g., a regular array) of biological, chemical, or physical entities. The steps exemplified in this method can be performed in different orders, one or more steps can be omitted or other processes can be added as additional steps. For example, a biological, chemical or physical entity can be attached to a seed prior to attaching the SNAP to the attachment sites on the array. For example, a seed can be a primer that is extended to form a SNAP or a seed can be a functionalized nucleotide that is incorporated into a nucleic acid strand of a SNAP. In an alternative method, the biological, chemical or physical entity can be attached to a SNAP after attaching the SNAP to the attachment sites on the array. The biological, chemical or physical entity can be attached to a seed region that is present in a SNAP (e.g., a primer or nucleotide having a moiety that is reactive to the entity), or the attachment can occur at another region of the SNAP whether or not the seed is a retained component of the SNAP. Moreover, a biological, chemical or physical entity can be attached to a seed before or after a SNAP is produced from the seed.

SNAPs can be composed of any type of nucleic acid-based nanoparticle, such as rolling circle amplification-based nanoparticles (i.e., RCA amplicons), plasmids, or nucleic acid origami nanoparticles (e.g., DNA or RNA origami nanoparticles). A nucleic acid-based nanoparticle can contain DNA, RNA or other nucleic acid. Nucleic acids can be useful components of nanoparticles, for example, due to the relative ease with which the nanoparticles can be produced using nucleic acid amplification techniques. However, nucleic acids need not be amplified in a method set forth herein. Whether or not amplification is employed, nucleic acids can be assembled by exploiting their complementary hybridization properties. For example, nucleic acids can be assembled into origami structures that form nanoparticles. Various methods may be used for making and using nucleic acid origami to attach one or more biological, chemical or physical entities to a solid support, such as an array.

In particular configurations, methods of producing an array of biological, chemical, or physical entities, such as proteins, may comprise attachment of a protein to an oligonucleotide primer via a linker. The primer can be then annealed to a circular DNA template, and rolling circle amplification can be performed to produce a SNAP (indicated in this example as a DNA cluster). In this way the primer functions as a seed for the SNAP that is produced by rolling circle amplification. The SNAP can be then deposited onto a chip. In this example, the negative charge of the DNA backbone can interact with positively charged features of an array, such that the SNAP becomes immobilized on the array.

As another example, methods of producing an array of biological, chemical, or physical entities may begin with initiating rolling circle amplification using a primer having a linker and a circular DNA template. The resulting SNAP (indicated in this example as a DNA cluster) thus comprises a linker, which can then be conjugated or otherwise attached to a protein. The SNAP can be then deposited onto a chip. In this example, the negative charge of the DNA backbone can interact with positively charged features of an array, such that the SNAP becomes immobilized on the array.

As another example, methods of producing an array of biological, chemical, or physical entities may begin with a primer initiating rolling circle amplification with a circular DNA template. The resulting SNAP (indicated in this example as a DNA cluster) can then be joined with a crosslinker, which can then be conjugated or otherwise attached with a protein, to result in a SNAP which is crosslinked to a protein. The SNAP can be then deposited onto a chip. In this example, the negative charge of the DNA backbone can interact with positively charged features of an array, such that the SNAP becomes immobilized on the array.

SNAPs may be created, for example by rolling circle amplification spontaneous assembly of complementary nucleic acids (e.g., scaffold strand and oligonucleotide strands) and/or other acceptable method. These SNAPs can be then deposited onto a chip. For example, the negative charge of the DNA backbone can interact with positively charged features of an array, such that the SNAP becomes immobilized on the array. Separately, proteins can be modified with chemical handles which can bind a chemical moiety which can be on the SNAPs. The handled proteins can then be applied to the SNAPs, such that they covalently attach to the SNAPs.

In some embodiments, the present disclosure provides arrays of single-molecules and methods and kits for producing arrays of single-molecules. In some embodiments, this disclosure provides arrays of biological, chemical, or physical entities and methods and kits for producing arrays of biological, chemical, or physical entities. In some examples, an array of biological, chemical, or physical entities may comprise an ordered series of biological, chemical, or physical entities arrayed on a solid support. The entities may be present at sites that are arranged in an ordered pattern (i.e., a repeating pattern of sites). In other examples, an array of biological, chemical, or physical entities may comprise an irregular array of biological, chemical, or physical entities. The entities may be present at sites that are in a non-patterned arrangement (i.e., a non-repeating pattern of sites).

In some embodiments, biological, chemical, or physical entities on an array may be separated by less than about 10 nm, 20 nm, 30 nm, 40 nm, 50 nm, 60 nm, 70 nm, 80 nm, 90 nm, 100 nm, 250 nm, 500 nm, 750 nm, 1 m, 5 m, 10 m, 25 m, 50 m, 100 m, 500 m, or more. Alternatively or additionally, biological, chemical, or physical entities on an array may be separated by more than about 10 nm, 20 nm, 30 nm, 40 nm, 50 nm, 60 nm, 70 nm, 80 nm, 90 nm, 100 nm, 500 nm, 1 m, 5 m, 10 m, 100 m, 500 m, or more. In some embodiments, biological, chemical, or physical entities on the array may be separated by between about 50 nm and about 1 m, about 50 nm and about 500 nm, about 100 nm and about 400 nm, about 200 nm and about 300 nm, about 500 nm and about 10 m, about 50 nm and about 1 m, or about 300 nm and about 1 m. In some embodiments, the spacing of biological, chemical, or physical entities on the array may be determined by the presence of attachment sites arrayed on a solid support.

In some embodiments, an array is created on a solid support. The solid support may be any solid surface to which molecules can be covalently or non-covalently attached. Non-limiting examples of solid supports include slides, surfaces of elements of devices, surface coatings of elements of devices, membranes, flow cells, wells, chambers, and macrofluidic chambers. Solid supports used herein may be flat or curved, or can have other shapes, and can be smooth or textured. In some embodiments, solid support surfaces may contain microwells. In some embodiments, substrate surfaces may contain nanowells. In some embodiments, solid support surfaces may contain one or more microwells in combination with one or more nanowells. In some embodiments, the solid support can be composed of silica, glass, carbohydrates such as dextrans, plastics such as polystyrene or polypropylene, polyacrylamide, latex, silicon, metals (such as gold, chromium, titanium, or tin, titanium oxide, or tin oxide), or cellulose. In some examples, the solid support may be a slide or a flow cell.

In some embodiments, surfaces of the solid support may be modified to allow or enhance covalent or non-covalent attachment of molecules such as the SNAPs described herein. The solid support and process for molecule attachment are preferably stable for repeated binding, washing, imaging and eluting steps. In some embodiments, surfaces may be modified to have a positive or negative charge. In some embodiments, surfaces may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The surfaces may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane.

In some embodiments, the solid support may be modified to reduce non-specific attachment of SNAPs to the solid support. In some embodiments, the solid support, or one or more regions thereof, may be modified to reduce non-specific attachment of biological entities and/or chemical entities to the solid support. In some embodiments, the solid support may be passivated. In some further embodiments, the surface of the solid support, or one or more regions thereof, may be passivated. In some embodiments, the passivation layer may include diamond-like carbon, hexamethyldisilizane, Teflon, fluorocarbon, a polymer such as polyethylene glycol (PEG) and/or Parylene. In some embodiments, a solid support may be passivated by the attachment of Polyethylene glycol (PEG) molecules across all of, or across one or more regions of, the solid support. In some embodiments, a solid support may be passivated using salmon sperm DNA, DNA origami tiles, glycols, albumin, or a combination of the above. In some embodiments, a solid support may be passivated using one or more components selected from the group consisting of salmon sperm DNA, DNA origami tiles, glycols, and albumin. In some embodiments, passivation components may be exposed to a surface. In some embodiments, passivation components may not be covalently bound to a surface. In some embodiments, passivation materials may be non-covalently bound to the solid support.

In some embodiments, the solid support may be modified across the entire surface to which molecules are to be attached. For example, the surface can lack unreactive regions that may otherwise form interstitial regions between reactive sites that attach to the molecules. In other embodiments, the solid support may contain one or more regions which are modified to allow attachment of molecules and one or more regions which are not modified, or one or more regions which are modified to decrease attachment of molecules and one or more regions which are not modified, or one or more regions which are modified to increase attachment of molecules and one or more regions which are modified to decrease attachment of molecules. For example, unmodified regions can form interstitial regions between sites where molecules have attached. In some embodiments, attachment sites may be created in an array, for example an ordered array.

An ordered array of attachment sites may be created by, for example, photolithography, Dip-Pen nanolithography, nanoimprint lithography, nanosphere lithography, cluster lithography, nanopillar arrays, nanowire lithography, scanning probe lithography, thermochemical lithography, thermal scanning probe lithography, local oxidation nanolithography, molecular self-assembly, stencil lithography, double-beam interference lithography, or electron-beam lithography. Attachment sites in an ordered array may be located such that each attachment site is less than about 20 nanometers (nm), 50 nm, 75 nm, 100 nm, 125 nm, 150 nm, 175 nm, 200 nm, 250 nm, 300 nm, 400 nm, 500 nm, 750 nm, 1000 nm, 1500 nm, 2000 nm, or more from any other attachment site.

In some embodiments, the spacing of attachment sites on the solid support may be selected depending on the size of the SNAPs to be used. For example the spacing of the attachment sites may be selected such that the closest distance between the edges of any two attachment sites is greater than the diameter of the SNAP used. In the case of non-circular SNAPs, the spacing of the attachment sites may be selected such that the closest distance between the edges of any two attachment sites is greater than the longest dimension of the SNAP used.

In some embodiments, the size of the attachment sites on the solid support may be selected depending on the size of the SNAPs to be used. For example the size of the attachment sites may be selected such that the diameter of each attachment sites is less than the diameter of the SNAP used. Optionally, the area of the attachment sites may be smaller than the area (i.e., footprint) of the SNAP used. Alternatively, the area of the attachment sites may be roughly equivalent to the occupied area (i.e., footprint) of the SNAP used or larger than the occupied area (i.e., footprint) of the SNAP used. Optionally, the area of the attachment sites may be sized to accommodate no more than a single SNAP, thereby preventing more than one SNAP from occupying the site at any time.

In some embodiments, the attachment sites may be provided in microwells or nanowells. In some embodiments, the attachment sites may be wells, such as nanowells or microwells. Optionally, the volume of the wells may be roughly equivalent to the volume of the SNAP used or larger than the volume of the SNAP used. Optionally, the cross sectional area of the wells may be roughly equivalent to the cross sectional area of the SNAP used or larger than the cross sectional area of the SNAP used. Optionally, the volume or cross sectional area of the wells may be sized to accommodate no more than a single SNAP, thereby preventing more than one SNAP from occupying the well at any time.

In some embodiments, sites or functional groups may be present in a random spacing and at a density such that sites or functional groups are on average at least about 50 nm, 100 nm, 200 nm, 300 nm, 400 nm, 500 nm, 600 nm, 700 nm, 800 nm, 900 nm, 1000 nm, or more from any other site or functional group. Alternatively or additionally, sites or functional groups may be present in a random spacing and at a density such that sites or functional groups are on average at most about 50 nm, about 100 nm, about 500 nm, about 1000 nm, or more from any nearest neighbor site or functional group.

The solid support may be indirectly functionalized. For example, the solid support may be PEGylated and a functional group may be applied to all or a subset of the PEG molecules.

In some embodiments, SNAPs can be used to indirectly functionalize proteins or other analytes to a solid support. The efficiency of attachment of SNAPs to the solid support may be high, moderate or low. The efficiency of the attachment of the SNAPs to the solid support may be influenced by many factors, including, but not limited to: sequence of clusters, size of SNAPs relative to size of a corresponding binding site (e.g., large clusters may not bind well to very small sites), the extent to which SNAPs have had their structure modified in such a way so as to influence their binding, age of SNAPs, storage conditions of a buffer or buffers that come into contact with SNAPs, storage conditions of SNAPs, pH or other properties of solvent in which the binding is desired to be achieved, concentration of positive cations, and temperature. The reliability of attachment of the SNAPs to the solid support may be high, moderate or low.

In some embodiments, a portion, portions, or all of the solid support may be optically opaque. In some embodiments, a portion, portions, or all of the solid support may be optically clear at one or more wavelengths. In some embodiments, a portion, portions, or all of the solid support may be partially optically clear, or may be optically clear in some regions. For example, an optical coating on the solid support may be optically opaque in regions that are not functionalized, and optically clear in regions that are functionalized.

In some configurations of the methods and systems set forth herein, a light sensing device can be integrated with a substrate (e.g., a solid support) to which analytes (e.g., biological, chemical, or physical entities) or other objects are attached. For example the substrate can include an array of landing sites or other sites, and light sensing device can be configured to observe analytes or other objects on or near a surface of the substrate. In some configurations, an array of sites on the surface of the substrate can be aligned with the integrated sensing device such that each of the sites is aligned with a single pixel or a cluster of pixels. For example, each of the sites can be aligned with a cluster of no more than 1 pixel, 2 pixels, 4 pixels, 9 pixels or 16 pixels. Integration allows the alignment to be maintained throughout the course of a method set forth herein or for the duration of using a light sensing device set forth herein. An example method for producing a solid support and integrated light sensing devices with attachment sites arrayed at desired intervals may begin with providing a substrate that positions an array of pixels forming a light sensing device (e.g., a commercially available light sensing device). The substrate may comprise, for example, a charge-coupled device (CCD) light sensing array, a complementary metal oxide semiconductor (CMOS) devices light sensing array, a light sensing array with a combination of CCD and CMOS devices, a charge injection device (CID) light sensing array, or a JOT image sensor. Substrate materials can be used in accordance with desired properties for positioning pixels, for positioning sites (e.g., landing sites) of an array, and for passing radiation at a wavelength that is produced by a substance to be detected by the pixels. The substrate may be made out of CMOS-compatible materials, thereby allowing their imaging side to be differentially functionalized, and biological, chemical, or physical entities can then be bound to specific locations. In some embodiments, the substrate may be glass. In particular, in some embodiments, the substrate may be amorphous glass, fused silica, or quartz, among other examples. In some embodiments, the substrate may be silicon. In some embodiments, the thickness of the substrate may be less than 100 microns, 100 microns, 150 microns, 200 microns, 300 microns, 400 microns, 500 microns, 600 microns, 700 microns, 800 microns, 900 microns, 1 millimeter, 2 millimeters, or more than 2 millimeters. In some embodiments, one biological, chemical, or physical entity to be detected is bound on each light sensing device (pixel). In some embodiments, the light path between the object to be imaged and the light sensing device can be advantageously reduced, thereby reducing the noise and distortions created along this light path by optical or flow cell components. In some embodiments, the substrate on which the biological, chemical, or physical entities are immobilized may not need to be scanned, thereby saving time, operation costs, and wear on the expensive parts of the instrument.

Initially, the substrate may be cleaned, such as with a piranha cleaning. In some embodiments, a substrate may be cleaned using a strong acid so as to clean the substrate without etching the substrate. In some embodiments, the substrate may be cleaned using a detergent. Alternatively, the substrate may be cleaned with solvent, sonication or with plasma such as $O_2$ or $N_2$ plasma, or with a combination thereof.

Once the substrate has been cleaned, a chrome layer can be deposited on the backside of the substrate. Deposition methods may include, for example, evaporation or sputtering. In some embodiments, a backside chrome evaporation may not be applied when a substrate is opaque. A backside chrome evaporation may have an average, maximum or minimum thickness of one Angstrom, two Angstroms, 10 Angstroms, 10 nanometers, 20 nanometers, 30 nanometers, 40 nanometers, 50 nanometers, 60 nanometers, 70 nanometers, 80 nanometers, 90 nanometers, 100 nanometers, 200 nanometers, 300 nanometers, 400 nanometers, 500 nanometers, or more. Alternatively, other metals can be used for deposition on the backside of the substrate, such as Aluminum, Tungsten, and/or Titanium, among other examples. Alternatively, dielectric mirrors can be used for deposition on the backside of the substrate.

In some embodiments, the analytes (e.g., biological, chemical, or physical entities) or objects to be imaged may be immobilized on a surface that is not integrated with a light sensing device. An example is a system configured to transmit radiation to or from a substrate using total internal reflection (TIR). In the case of luminescence detection, excitation can be delivered to an object at or near the surface of a substrate and emission can be transmitted through space for detection by a light sensing device. Another useful configuration is one in which an excitation source is positioned to send radiation through space to an object (e.g., an analyte on the surface of a solid support) and a light sensing device is positioned to receive radiation transmitted through space from the object or analyte. A particularly useful configuration is an epiluminescent configuration in which excitation and emission are transmitted to and from the same side of an object, for example, along parallel paths, albeit in opposite directions akin to a two lane highway.

Further, fiducials may be created on a face of a substrate that is to be detected such as the front side of the substrate. Fiducials may be created by adding at least one layer of material and by patterning this at least one layer. In some embodiments, such material can be chrome, and/or such materials may be other metals like tungsten or gold. Alternatively, dielectric mirrors may be used as a material for fiducials. Alternatively, metal oxide may be used for the fiducials as for example $ZrO_2$. The patterning of such materials can be performed in a variety of ways. A first way to pattern the fiducial material is to deposit a blanket layer of the material, then to protect this material in selected areas and remove the material in the areas where it is not protected. This can for example be achieved by coating the front side of the substrate with photosensitive material (e.g., photoresist), patterning this photoresist by exposing it to UV light through a mask and then developing it. The etching of the fiducial material can then be performed by wet etch (for example acid) or dry etch (for example Reactive Ion Etching, RIE). Alternatively, the photoresist may be deposited and patterned first. In some embodiments, where the photoresist is deposited and patterned first, areas are defined that are free of such photoresist and then the fiducial material may be deposited on top of the photoresist. The photoresist may then be removed (for example, in a solvent bath with sonication) and the fiducial material may be left on the areas that were initially free of photoresist (e.g., using a lift-off technique). Alternatively, fiducials may be created by removing material from the substrate in selected areas, for example by patterning a layer of photoresist on the front side of the substrate and then by dry etching the substrate in the areas that are not coated with photoresist. In another alternative, fiducials may be defined by modifying the substrate locally (for example by laser melting and/or fractioning). Fiducials may come in a variety of shapes, lines, and/or orientations. In some embodiments, a pattern of fiducials may be applied to the substrate. In yet another embodiment, the shape of fiducials may vary in order to code information about their location on the surface of the substrate. Another useful type of fiducial is a substance that is delivered to a substrate after being manufactured such that the substance is deposited on the substrate at a location within the field of view of an imaging device. One or more of such substances can attach to the substrate at (a) specified position(s) or random position(s). Substances that are retained at their attached positions of an array throughout multiple imaging steps can be used for image registration, thereby allowing the multiple images of the array to be aligned with respect to each other. A subset of such fiducials can be useful for image registration even if others in the set are not retained or visible throughout multiple imaging steps. Moreover, substances at a particular fiducial can be replaced or modified to provide viable signals across multiple imaging steps.

Particularly useful substances include analytes set forth herein, affinity agents set forth herein, or substances used to mediate attachment of analytes to substrates such as SNAPs or linkers. The substances can be labeled with luminophores or other moieties set forth herein and can be detected by an imaging device that is used for detecting other analytes. The fiducial substances can also be attached to analytes that are to be characterized or measured for purposes other than image registration, but fiducial substances need not be attached to such analytes.

Before, during or after creating a pattern of fiducials on the front side of a substrate, this front side may be differentially coated to define features where objects of interest (for example, nucleic acid clusters or SNAPs covalently attached to a protein) may be immobilized. In a first embodiment, the surface may be differentially patterned with two silanes, for example HMDS or a PEG-silane in the field (e.g., interstitial regions between immobilization sites) and APTES on the immobilization sites. This differential patterning is achieved by, for example, depositing an initial HMDS layer on the surface, followed by a lift-off layer, followed by an optional anti-reflective layer, and followed by a photoresist layer. In some embodiments, an anti-reflective layer may not be provided when an opaque substrate is being used.

Once the photoresist is applied, a second lithography step may be provided. In particular, desired features may be provided. In some embodiments, desired features may have a length of approximately 300 nm. In some embodiments, features may have a length of less than 50 nm, 100 nm, 200 nm, 300 nm, 400 nm, 500 nm, 600 nm, 700 nm, or more. In some further embodiments, one or more layers deposited on the surface to perform this second lithography may not be etched by the developing step of this second lithography (for example, the antireflective coating).

In embodiments where a backside coating is provided, the backside coating may be removed, such as through the use of a wet etch or dry etch etc. Further, a directional reactive ion etch (RIE) may be provided so as to remove layers that haven't been removed by the lithography step (for example the antireflective coating).

In some embodiments, cleaning may be performed, which may include an oxygen plasma cleaning and activation step. Once the chip has been cleaned, an amino-silane deposition may be provided. Once the amino-silane deposition is provided, portions of the chip manufacture may be lifted-off, such as using hot DMF. Further, a sonication step may be performed. The resulting chip may be used (for example, in flow cells) for assessments of biological assays or other processes.

In an alternative embodiment, the surface may be differentially patterned with a silane layer and a metal layer (for example, (3-Aminopropyl)triethoxysilane (APTES) on the immobilization sites and chrome in the interstitial regions between the sites or elsewhere in the field). In another embodiment, the surface may be differentially patterned with a silane layer and a metal oxide layer (for example a PEG-silane layer in the interstitial regions between the sites or elsewhere in the field and a $ZrO_2$ layer on the immobilization sites). In yet another embodiment, the surface may be differentially patterned with a silane layer on the immobilization sites (for example, acyl protein thioesterases (APTS)) and a metal oxide layer (for example a $ZrO_2$) and a PEG-phosphonic acid layer in the interstitial regions between the sites or elsewhere in the field.

For configurations that utilize array-based detection, the biological, chemical, or physical entities of this disclosure may be any biological, chemical, or physical entities for which spatial separation is desired. In some embodiments, the biological, chemical, or physical entities are proteins. In some embodiments, the proteins may be proteins from a cell or tissue homogenate, from a biological fluid, or from an environmental sample. The proteins can be relatively short, such as proteins that are often referred to as polypeptides or oligopeptides, or the proteins can be relatively large such as those that form higher order tertiary or quaternary structures. In some embodiments, the biological, chemical, or physical entities may be antibodies or other receptors. In some embodiments, the biological, chemical, or physical entities are nucleic acids. For example the biological, chemical, or physical entities may be DNAs, RNAs, mRNAs, tRNAs, or miRNAs. The nucleic acids can be peptide nucleic acid (PNAs) or other synthetic analogs of naturally occurring nucleic acids. In some embodiments, the biological, chemical, or physical entities are carbohydrates, metabolites, hormones or molecules having biological activity. In some embodiments, the biological, chemical, or physical entities are complex polymers. In some embodiments, the biological, chemical, or physical entities are small molecules, for example, chemical compounds rather than complex polymers.

The biological, chemical, or physical entities of this disclosure may be attached to seeds. These seeds are molecules which can be used as a starting moiety or monomeric moiety to grow a larger polymeric molecule. The seed may be a monomer, oligomer or other precursor capable of incorporation into a polymer. Generally, the seeds are molecules (or moieties of molecules) which can be covalently attached to biological, chemical, or physical entities set forth herein. The seeds may have a polarity such that only one functional group of the seed is able to bind to a biological, chemical, or physical entity, while another one or more functional groups of the seed can form the starting point for a polymer.

Examples of monomers or precursors which may be present in a seed include, but are not limited to, oligonucleotides, nucleotides, carbohydrates, sugars, proteins, amino acids, amyloids, fibrils, and tetratricopeptide repeats. In some embodiments, the seeds are small molecules. Particularly useful monomers are nucleotides that can be incorporated into nucleic acid polymers, or oligonucleotides (e.g., primers) that can be extended or ligated to form nucleic acid polymers.

The seeds may comprise a monomer and a functional group able to bind to a biological, chemical, or physical entity to be separated. Examples of such functional groups may include, but are not limited to, amines, thiols, carboxylic acids, triple bonds, double bonds, epoxides, alkynes, alkenes, cycloalkynes, azides, cyclo-octynes, cycloalkynes, norbornenes, tetrazines, cyclloctanes, epoxides, and hydroxyls. In some embodiments, the seed may comprise a functional group that is compatible with a click chemistry. Various click chemistry reagents and techniques can be used in this embodiment or others set forth herein. In some embodiments, the seed may also comprise a linker or spacer between the seed and the functional group. In some embodiments, the linker or spacer may comprise a photo-cleavable bond. In some embodiments, the seed may comprise an oligonucleotide conjugated to an amine group, for example, on the 5' terminal nucleotide of the oligonucleotide. In some embodiments, the seed may comprise an oligonucleotide conjugated to a click chemistry component, for example, on the 5' terminal nucleotide of the oligonucleotide.

In some embodiments, bioconjugation may be used to form a covalent bond between two molecules, at least one of which is a biomolecule. For example, bioconjugation can attach a SNAP to a protein or to another analyte that is to be detected or manipulated in a method set forth herein. In some embodiments, bioconjugation may be used to form a covalent bond between a biomolecule and a moiety on the surface of a solid support. For example, bioconjugation can attach a SNAP to a solid support. Exemplary moieties include, but are not limited to, silanes and other functional groups set forth herein in the context of attaching molecules to surfaces.

Bioconjugation may be formed, for example, via chemical conjugation, enzymatic conjugation, photo-conjugation, thermal-conjugation, or a combination thereof (Spicer, C. D., Pashuck, E. T., & Stevens, M. M., Achieving Controlled Biomolecule-Biomaterial Conjugation. Chemical Reviews., 2018, 118, Pgs. 7702-7743, and Greg T. Hermanson, "Bioconjugate Techniques", Academic Press; $3^{rd}$ Edition, 2013, herein incorporated by reference for this disclosure). In some embodiments, both the seed and the biological (e.g., SNAP), chemical, or physical entity may be functionalized. Functionalizing both partners may improve the efficiency or speed of a conjugation reaction. For example, a sulfhydryl group (—SH) or amine (—$NH_2$) of a chemically active site of a seed, biological, chemical, or physical entity may be functionalized to allow for greater reactivity or efficiency of a conjugation reaction. Any of a variety of sulfhydryl-reactive (or thiol-reactive) or amine conjugation chemistries may be used to couple chemical moieties to sulfhydryl or amine groups. Examples include, but are not limited to, use of haloacetyls, maleimides, aziridines, acryloyls, arylating agents, vinylsulfones, pyridyl disulfides, TNB-thiols and/or other sulfhydryl-reactive/amine-reactive/thiol-reactive agents. Many of these groups conjugate to sulfhydryl groups through either alkylation (e.g., by formation of a thioether or amine bond) or disulfide exchange (e.g., by formation of a disulfide bond). More strategies and detail regarding reactions for bioconjugation are described down below and may be extended to other appropriate biomolecules.

Bioconjugation can be accomplished in part by a chemical reaction of a chemical moiety or linker molecule with a chemically active site on the biomolecule. The chemical conjugation may proceed via an amide formation reaction, reductive amination reaction, N-terminal modification, thiol Michael addition reaction, disulfide formation reaction, copper(I)-catalyzed alkyne-azide cycloaddition (CuAAC) reaction, strain-promoted alkyne-azide cycloaddtion reaction (SPAAC), Strain-promoted alkyne-nitrone cycloaddition (SPANC), invers electron-demand Diels-Alder (IEDDA) reaction, oxime/hydrazone formation reaction, free-radical polymerization reaction, or a combination thereof. Enzyme-mediated conjugation may proceed via transglutaminases, peroxidases, sortase, SpyTag-SpyCatcher, or a combination thereof. Photoconjugated and activation may proceed via photoacrylate cross-linking reaction, photo thiol-ene reaction, photo thiol-yne reaction, or a combination thereof. In some embodiments, conjugation may proceed via noncovalent interactions, these may be through self-assembling peptides, binding sequences, host-guest chemistry, nucleic acids, or a combination thereof.

In some embodiments, site-selectivity methods may be employed to modify reaction moieties of biomolecules to increase conjugation efficiency, ease of use, reproducibility. Various strategies may be employed for site-selective bioconjugation. (i) Modification strategies that can select a single motif among many, rather than targeting a generic reactive handle. This may be determined by surrounding a sequence, local environment, or subtle differences in reactivity. The ability of enzymes to modify a specific amino acid within a protein sequence or a glycan at a single position are particularly prominent. Reactions that display exquisite chemo-selectivity also fall within this category, such as those that target the unique reactivity of the protein N-terminus or the anomeric position of glycans. (ii) The site-specific incorporation of unnatural functionalities, by hijacking native biosynthetic pathways may be utilized. (iii) The installation of unique reactivity via chemical synthesis may be utilized. The complete or partial synthesis of peptides and oligonucleotides is widespread, particularly using solid-phase approaches. These techniques allow access to sequences of up to 100 amino acids or 200 nucleotides, with the ability to install a wide variety of functionalized monomers with precise positional control.

In some embodiments, chemical conjugation techniques may be applied for creating biomaterial-biomolecule conjugates. Functional groups used for bioconjugation may be native to the biomolecule or may be incorporated synthetically. In the illustrations below, R and R' may be a biomolecule (for example, but not limited to: SNAP, proteins, amino acids, nucleic acids, nucleotides, carbohydrates, lipids, metabolites, small molecules, monomers, oligomers, polymers) and/or a solid support (e.g., a silane, linker or functional group that is attached to the solid support).

In some embodiments, reductive amination may be utilized for bioconjugation. Amines can react reversibly with aldehydes to form a transient imine moiety, with accompanying elimination of water. This reaction takes place in rapid equilibrium, with the unconjugated starting materials being strongly favored in aqueous conditions due to the high concentration of water. However, in a second step the unstable imine can be irreversibly reduced to the corresponding amine via treatment with sodium cyanoborohydride. This mild reducing reagent enables the selective reduction of imines even in the presence of unreacted aldehydes. As a result, irreversible conjugation of a biomolecule can gradually occur to a biomaterial of interest. In contrast, stronger reducing agents such as sodium borohydride are also able to reduce aldehydes. This two-step reductive amination process can also be utilized for the modification of ketones. For example, reductive amination has therefore been primarily used for the modification of sodium periodate-treated alginate and chitosan scaffolds. The order of reactivity may also be reversed for the attachment of reducing sugars, by exploiting the terminal aldehyde/ketone generated in the open-chain form. This strategy, for example, may be exploited to mimic the glucosylation, glycosylation, and/or galactosylation patterns of native collagen in ECM, via reductive amination of maltose and lactose respectively.

In some embodiments, isothiocyanates of a biomolecule or solid support may be utilized for bioconjugation. For example, isothiocyanate of a biomolecule may react with nucleophiles such as amines, sulfhydryls, the phenolate ion of tyrosine side chains or other biomolecules to form a stable bond between two molecules.

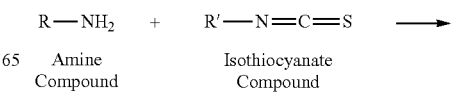

R—$NH_2$ + R'—N=C=S ⟶

Amine Compound     Isothiocyanate Compound

-continued

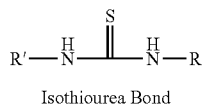

Isothiourea Bond

In some embodiments, an isocyanate of a biomolecule or solid support may be utilized for bioconjugation. For example, isocyanates can react with amine-containing molecules to form stable isourea linkages.

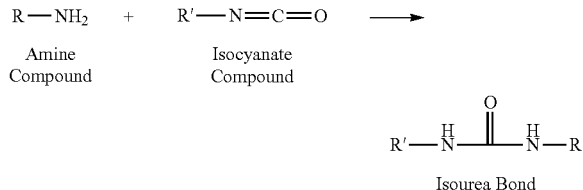

Isourea Bond

In some embodiments, an acyl azide of a biomolecule or solid support may be utilized for bioconjugation. For example, acyl azide are activated carboxylate groups that can react with primary amines to form amide bonds.

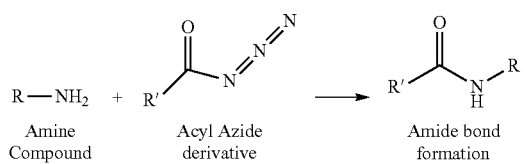

In some embodiments, an amide of a biomolecule or solid support may be utilized for bioconjugation. For example, the use of reactive N-hydroxysuccinimide (NHS) esters is particularly widespread. While NHS-esters can be performed, often they are instead generated in situ through the use of N-(3-(dimethylamino)propyl)-N'-ethylcarbodiimide (EDC) coupling chemistry and coupled directly to the species of interest. Although formation of the activated NHS-ester is favored under mildly acidic conditions (pH~5), subsequent amide coupling is accelerated at higher pHs at which the amine coupling partner is not protonated. One-step modification at an intermediate pH of ~6.5 is possible. Conjugation can be undertaken by first forming the active NHS-ester at pH 5, before raising the pH to ~8 and adding the amine coupling partner in a two-step procedure. In some embodiments, water-soluble derivative sulfo-NHS may be utilized as an alternative. In some embodiments, NHS esters of a biomolecule can react and couple with tyrosine, serine, and threonine —OH groups as opposed to N-terminal α-amines and lysine side-chain C-amines.

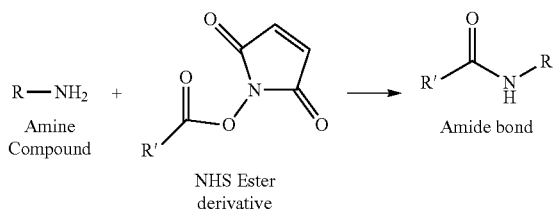

In some embodiments, a sulfonyl chloride of a biomolecule or solid support may be utilized for bioconjugation. For example, reaction of a sulfonyl chloride compound with a primary amine-containing molecule proceeds with loss of the chlorine atom and formation of a sulfonamide linkage.

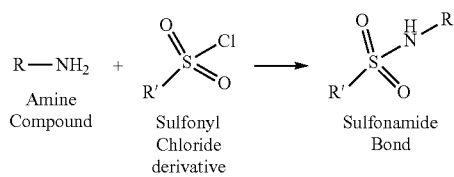

In some embodiments, a tosylate ester of a biomolecule or solid support may be utilized for bioconjugation. For example, reactive groups comprising tosylate esters can be formed from the reaction of 4-toluenesulfonyl chloride (also called tosyl chloride or TsCl) with a hydroxyl group to yield the sulfonyl ester derivative. The sulfonyl ester may couple with nucleophiles to produce a covalent bond and may result in a secondary amine linkage with primary amines, a thioether linkage with sulfhydryl groups, or an ether bond with hydroxyls.

In some embodiments, a carbonyl of a biomolecule or solid support may be utilized for bioconjugation. For example, carbonyl groups such as aldehydes, ketones, and glyoxals can react with amines to form Schiff base intermediates which are in equilibrium with their free forms. In some embodiments, the addition of sodium borohydride or sodium cyanoborohydride to a reaction medium containing an aldehyde compound and an amine-containing molecule may result in reduction of the Schiff base intermediate and covalent bond formation, creating a secondary amine linkage between the two molecules.

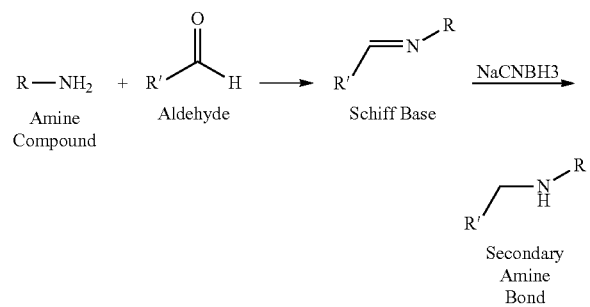

In some embodiments, an epoxide or oxirane of a biomolecule or solid support may be utilized for bioconjugation. For example, an epoxide or oxirane group of a biomolecule may react with nucleo-philes in a ring-opening process. The reaction can take place with primary amines, sulfhydryls, or hydroxyl groups to create secondary amine, thioether, or ether bonds, respectively.

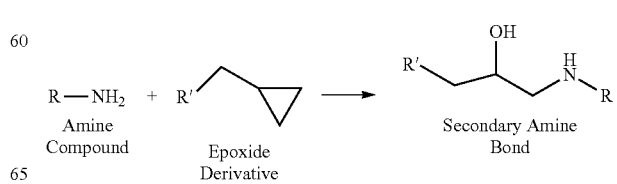

In some embodiments, a carbonate of a biomolecule or solid support may be utilized for bioconjugation. For example, carbonates may react with nucleophiles to form carbamate linkages, disuccinimidyl carbonate, can be used to activate hydroxyl-containing molecules to form amine-reactive succinimidyl carbonate intermediates. In some embodiments, this carbonate activation procedure can be used in coupling polyethylene glycol (PEG) to proteins and other amine-containing molecules. In some embodiments, nucleophiles, such as the primary amino groups of proteins, can react with the succinimidyl carbonate functional groups to give stable carbamate (aliphatic urethane) bonds

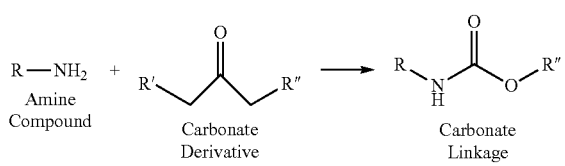

In some embodiments, an aryl halide of a biomolecule or solid support may be utilized for bioconjugation. For example, aryl halide compounds such as fluorobenzene derivatives can be used to form covalent bonds with amine-containing molecules like proteins. Other nucleophiles such as thiol, imidazolyl, and phenolate groups of amino acid side chains can also react to form stable bonds with a biomolecule or solid support. In some embodiments, fluorobenzene-type compounds have been used as functional groups in homobifunctional crosslinking agents. For example, their reaction with amines involves nucleophilic displacement of the fluorine atom with the amine derivative, creating a substituted aryl amine bond.

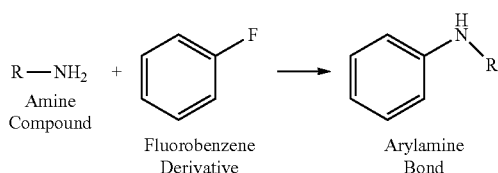

In some embodiments, an imidoester of a biomolecule or solid support may be utilized for bioconjugation. For example, the α-amines and ε-amines of proteins may be targeted and crosslinked by reacting with homobifunctional imidoesters. In some embodiments, after conjugating two proteins with a bifunctional imidoester crosslinker, excess imidoester functional groups may be blocked with ethanolamine.

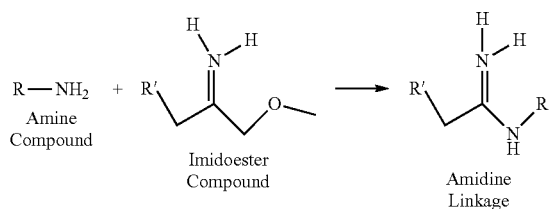

In some embodiments, carbodiimides may be utilized for bioconjugation. Generally, carbodiimides are zero-length crosslinking agents that may be used to mediate the formation of an amide or phosphoramidate linkage between a carboxylate group and an amine or a phosphate and an amine, respectively. Carbodiimides are zero-length reagents because in forming these bonds no additional chemical structure is introduced between the conjugating molecules. In some embodiments, N-substituted carbodiimides can react with carboxylic acids to form highly reactive, O-acylisourea derivatives. This active species may then react with a nucleophile such as a primary amine to form an amide bond. In some embodiments, sulfhydryl groups may attack the active species and form thioester linkages. In some embodiments, hydrazide-containing compounds can also be coupled to carboxylate groups using a carbodiimide-mediated reaction. Using bifunctional hydrazide reagents, carboxylates may be modified to possess terminal hydra-zide groups able to conjugate with other carbonyl compounds.

In some embodiments, a biomolecule or solid support containing phosphate groups, such as the 5' phosphate of oligonucleotides, may also be conjugated to amine-containing molecules or moieties by using a carbodiimide-mediated reaction. For example, the carbodiimide of a biomolecule may activate the phosphate to an intermediate phosphate ester similar to its reaction with carboxylates. In the presence of an amine, the ester reacts to form a stable phosphoramidate bond.

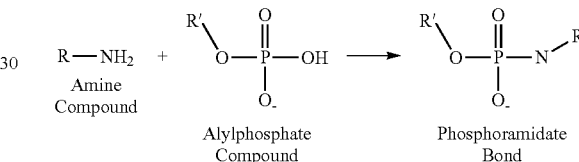

In some embodiments, an acid anhydride of a biomolecule or solid support may be utilized for bioconjugation. Anhydrides are highly reactive toward nucleophiles and are able to acylate a number of the important functional groups of proteins and other biomolecules. For example, protein functional groups able to react with anhydrides include but not limited to the α-amines at the N-terminals, the ε-amine of lysine side chains, cysteine sulfhydryl groups, the phenolate ion of tyrosine residues, and the imid-azolyl ring of histidines. In some embodiments, the site of reactivity for anhydrides in protein molecules is modification of any attached carbohydrate chains. In some embodiments, in addition to amino group modification in a polypeptide chain, glycoproteins may be modified at their polysaccharide hydroxyl groups to form esterified derivatives.

In some embodiments, a fluorophenyl ester of a biomolecule or solid support may be utilized for bioconjugation. Flurophenyl esters can be another type of carboxylic acid derivative that may react with amines consists of the ester of a fluorophenol compound, which creates a group capable of forming amide bonds with proteins and other molecules. In some embodiments, fluorophenyl esters may be: a pentafluorophenyl (PFP) ester, a tetrafluorophenyl (TFP) ester, or a sulfo-tetrafluoro-phenyl (STP) ester. In some embodiments, fluorophenyl esters react with amine-containing molecules at slightly alkaline pH values to give the same amide bond linkages as NHS esters.

In some embodiments, hydroxymethyl phosphine of a biomolecule or solid support may be utilized for bioconjugation. Phosphine derivatives with hydroxymethyl group substitutions may act as bioconjugation agents for coupling or crosslinking purposes. For example, tris(hydroxymethyl)

phosphine (THP) and β-[tris(hydroxymethyl)phos-phino] propionic acid (THPP) are small trifunctional compounds that spontaneously react with nucleophiles, such as amines, to form covalent linkages.

In some embodiments, the thiol reactivity of a biomolecule or solid support may be utilized for bioconjugation. For example, the thiol group of cysteine is the most nucleophilic functional group found among the 20 proteinogenic amino acids. Through careful control of pH, selective modification over other nucleophilic residues such as lysine can be achieved. As another example, thiol modification of oligonucleotides may be used to enable derivatization, though the ease with which alternative reactive handles with enhanced chemical orthogonality can be installed has limited use for biomaterial-conjugation. Further, the conjugate addition of thiols to α,β-unsaturated carbonyls, also referred to as Michael addition, may be used to form polypeptide conjugates in the fields of tissue engineering, functional materials, and protein modification. In general, reaction rates and conjugation efficiencies are primarily controlled by three factors and may be modified as needed: (i) the $pK_a$ of the thiol; (ii) the electrophilicity of the Michael-acceptor; (iii) the choice of catalyst. Regarding (i): the thiolate anion is the active nucleophile during Michael addition, and the propensity of the thiol to undergo deprotonation may determine thiolate concentration and thus reaction rates. For example, the lower $pK_a$ of aromatic thiols, when compared to their aliphatic counterparts, leads to a higher rate of reaction rate a weak base is used to catalyze the. As a result, local structure can significantly alter conjugation efficiency, particularly for polypeptide substrates. The $pK_a$ and reactivity of cysteine containing peptides can be altered significantly through rational choice of surrounding amino acids, the presence of positively charged amino acids, such as lysine and arginine, acts to lower the thiol $pK_a$ and thus enhance reactivity. Regarding (ii): the Michael-acceptor becomes more electron deficient it becomes more activated toward nucleophilic attack, and thus reaction rates increase. Within the most widely utilized acceptors in the biomaterial field, a trend of reactivity can be generalized as maleimides>vinyl sulfones>acrylates>acrylamides>methacrylates. Regarding (iii): Michael additions can be accelerated by either basic or nucleophilic catalysis (although both act by increasing the concentration of the active thiolate).

In some embodiments, the unique nucleophilicity of thiols can be exploited for selective reaction with a number of alternative electrophiles, which allow efficient and selective biomolecule attachment to be achieved. For example, one such group are α-halocarbonyls, with iodoacetamide based reagents finding particular utility. Higher thiol selectivity may be achieved using less electrophilic bromo and even chloro derivatives, though reactivity is also drastically reduced. More recently, methylsulfonyl heteroaromatic derivatives have emerged as promising reagents for thiol-specific conjugation. In other cases, alternative thiol-reactive handles, such as disulfide-bridging pyridazinediones, carbonylacrylic reagents, and cyclopropenyl ketones may be utilized for bioconjugation.

In some embodiments, sulfhydryl of a biomolecule or solid support may be utilized for bioconjugation. In some embodiments, three forms of activated halogen derivatives can be used to create sulfhydryl-reactive compounds: haloacetyl, benzyl halides, and alkyl halides. In each of these compounds, the halogen group may be easily displaced by an attacking nucleophilic substance to form an alkylated derivative with loss of HX (where X is the halogen and the hydrogen comes from the nucleophile). Haloacetyl compounds and benzyl halides can be iodine or bromine derivatives, whereas the halo-mustards can employ chlorine and bromine forms. Iodoacetyl groups have also been used successfully to couple affinity ligands to chromatography supports.

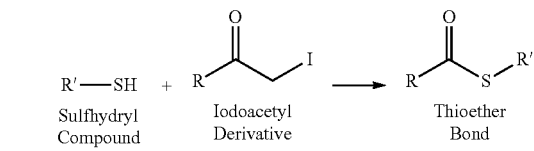

Sulfhydryl Compound    Iodoacetyl Derivative    Thioether Bond

In some embodiments, a maleimide of a biomolecule or solid support may be utilized for bioconjugation. The double bond of maleimides may undergo an alkylation reaction with sulfhydryl groups to form stable thioether bonds.

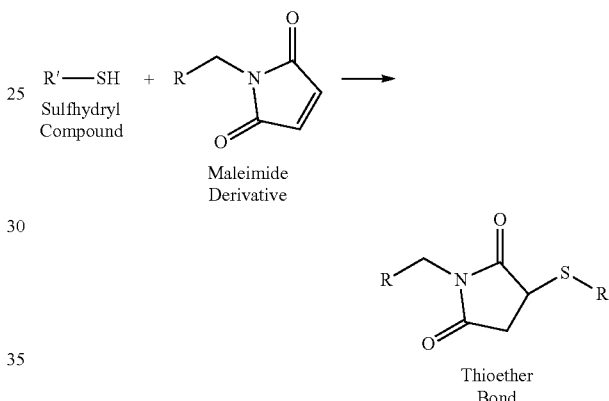

Sulfhydryl Compound    Maleimide Derivative

Thioether Bond

In some embodiments, an aziridine of a biomolecule or solid support may be utilized for bioconjugation. The highly hindered nature of this heterocyclic ring gives it strong reactivity toward nucleophiles. For example, sulfhydryls may react with aziridine-containing reagents in a ring-opening process, forming thioether bonds. The simplest aziridine compound, ethylenimine, can be used to transform available sulfhydryl groups into amines. In some embodiments, substituted aziridines may be used to form homobifunctional and trifunctional crosslinking agents.

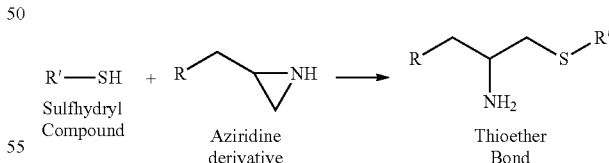

Sulfhydryl Compound    Aziridine derivative    Thioether Bond

In some embodiments, thiol-maleimide reactions are particularly useful for undertaking conjugation at low concentrations or when requiring extremely high efficiencies due to the value of the biomolecule substrate. The use of maleimides in bioconjugation is further enhanced by the ease with which they may be introduced into a wide range of scaffold materials, through the modification of amines with the difunctional reagent succinimidyl 4-(N-maleimidomethyl) cyclohexane-1-carboxylate, more commonly referred to by its abbreviation SMCC. For example, this reagent has been widely used to first introduce a maleimide reactive handle on a biomaterial of choice and then to enable the attachment of both peptides and growth factors to produce bioactive scaffolds.

In some embodiments, an acryloyl of a biomolecule or solid support may be utilized for bioconjugation. The reactive double bonds are capable of undergoing additional reactions with sulfhydryl groups. In some embodiments, the reaction of an acryloyl compound with a sulfhydryl group occurs with the creation of a stable thioether bond. In some embodiments, the acryloyl has found use in the design of the sulfhydryl-reactive fluorescent label, 6-acryloyl-2-dimethyl-aminonaphthalene.

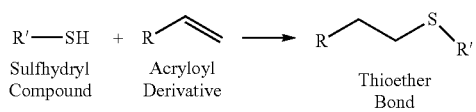

In some embodiments, an aryl group of a biomolecule or solid support may be utilized for bioconjugation with a sulfhydryl group. Although aryl halides may be used to modify amine-containing molecules to form aryl amine derivatives, they also may react quite readily with sulfhydryl groups. For example, fluorobenzene-type compounds have been used as functional groups in homobifunctional crosslinking agents. Their reaction with nucleophiles involves bimolecular nucleophilic substitution, causing the replacement of the fluorine atom with the sulfhydryl derivative and creating a substituted aryl bond. Conjugates formed with sulfhydryl groups are reversible by cleaving with an excess of thiol (such as DTT).

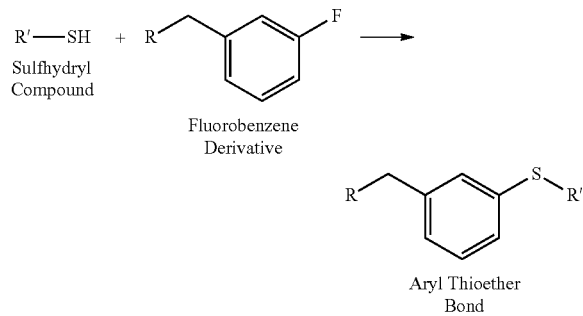

In some embodiments, the disulfide group of a biomolecule or solid support may be utilized for bioconjugation. In some embodiments, compounds containing a disulfide group are able to participate in disulfide exchange reactions with another thiol. The disulfide exchange (also called interchange) process involves attack of the thiol at the disulfide, breaking the —S—S— bond, with subsequent formation of a new mixed disulfide comprising a portion of the original disulfide compound. The reduction of disulfide groups to sulfhydryls in proteins using thiol-containing reductants proceeds through the intermediate formation of a mixed disulfide. In some embodiments, crosslinking or modification reactions may use disulfide exchange processes to form disulfide linkages with sulfhydryl-containing molecules

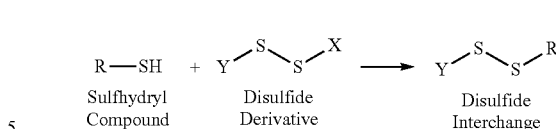

In some embodiments, disulfide bonds may be utilized for bioconjugation. For example, the use of disulfide exchange reactions may be favored for introducing peptides or proteins of interest. Commonly used reagents in tissue engineering may be based upon reactive pyridylthio-disulfides, which undergo rapid thiol-exchange to release the poorly nucleophilic and spectroscopically active 2-mercaptopyridine. Additionally, due to the reversible nature of disulfide bond formation, cleavage can be controlled with temporal precision by the addition of reducing agents such as dithiothreitol (DTT) or glutathione.

In some embodiments, a pyridyl dithiol functional group may be used in the construction of crosslinkers or modification reagents for bioconjugation. Pyridyl disulfides may be created from available primary amines on molecules through the reaction of 2-iminothiolane in tandem with 4,4'-dipyridyl disulfide. For instance, the simultaneous reaction among a protein or other biomolecule, 2-iminothiolane, and 4,4'-dipyri-dyl disulfide yields a modification containing reactive pyridyl disulfide groups in a single step. A pyridyl disulfide may readily undergo an interchange reaction with a free sulfhydryl to yield a single mixed disulfide product.

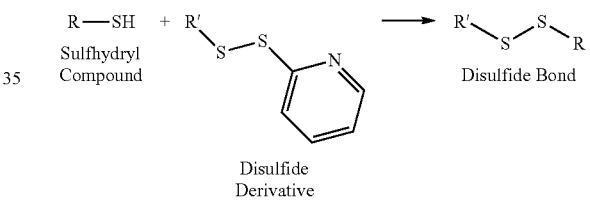

In some embodiments, sulfhydryl groups activated with the leaving group 5-thio-2-nitrobenzoic acid can be used to couple free thiols by disulfide interchange similar to pyridyl disulfides, as described herein. The disulfide of Ellman's reagent readily undergoes disulfide exchange with a free sulfhydryl to form a mixed disulfide with concomitant release of one molecule of the chromogenic substance 5-sulfido-2-nitroben-zoate, also called 5-thio-2-nitrobenzoic acid (TNB). The TNB-thiol group can again undergo interchange with a sulfhydryl-containing target molecule to yield a disulfide crosslink. Upon coupling with a sulfhydryl compound, the TNB group is released.

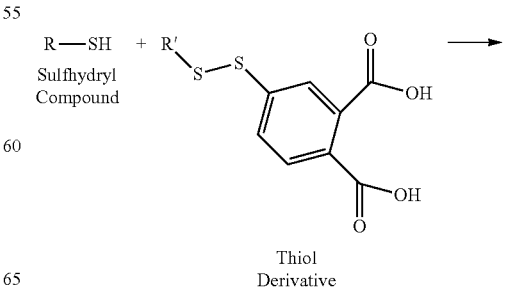

-continued

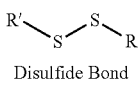
Disulfide Bond

In some embodiments, disulfide reduction may be performed using thiol-containing compounds such as TCEP, DTT, 2-mercaptoethanol, or 2-mercaptoethylamine.

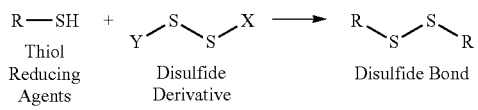

In some embodiments, a vinyl sulfone group of a biomolecule or solid support may be utilized for bioconjugation. For example, the Michael addition of thiols to activated vinyl sulfones to form biomolecule-material conjugates have been used to demonstrate that cysteine capped peptides may cross-link vinyl-sulfone functionalized multiarm PEGs to form protease responsive hydrogels, enabling cell invasion during tissue growth. In some embodiments, in addition to thiols, vinyl sulfone groups can react with amines and hydroxyls under higher pH conditions. The product of the reaction of a thiol with a vinyl sulfone gives a single stereoisomer structure. In addition, crosslinkers and modification reagents containing a vinyl sulfone can be used to activate surfaces or molecules to contain thiol-reactive groups.

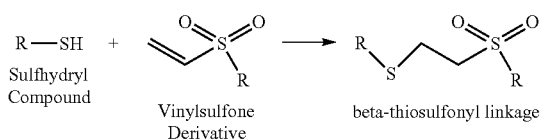

In some embodiments, thiol-containing biomolecules can interact with metal ions and metal surfaces to form dative bonds for bioconjugation. In some embodiments, oxygen- and nitrogen-containing organic or biomolecules may be used to chelate metal ions, such as in various lanthanide chelates, bifunctional metal chelating compounds, and FeBABE. In addition, amino acid side chains and prosthetic groups in proteins frequently form bioinorganic motifs by coordinating a metal ion as part of an active center.

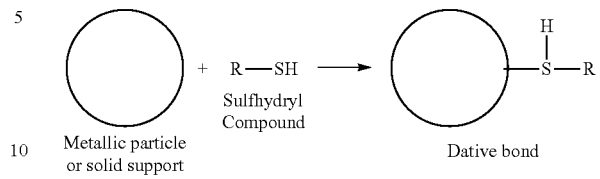

In some embodiments, thiol organic compounds may be used routinely to coat metallic surfaces or particles to form biocompatible layers or create functional groups for further conjugation of biomolecules. For instance, thiol-containing aliphatic/PEG linkers have been used to form self-assembled monolayers (SAMs) on planar gold surfaces and particles.

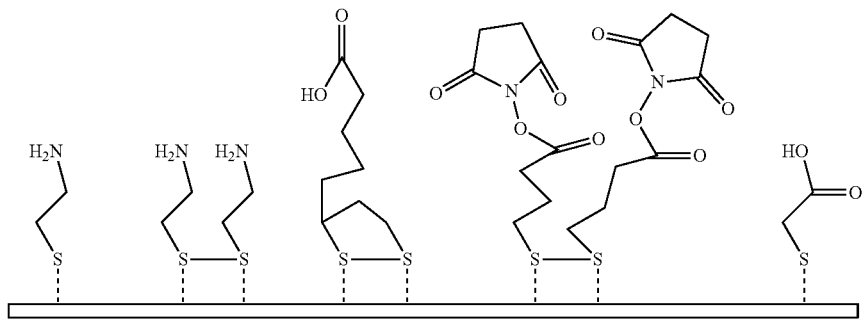

In some embodiments, a number of alternative coupling systems may be used for biomolecule functionalization. These include the use of O-nitrophenyl esters (which possess reduced stability in aqueous conditions) or 1,1'-carbonyldiimidazole (CDI) to form amine-bridging carbamate linkages rather than amides. Hydrazines can also be used in place of amines during EDC/NHS mediated couplings. Hydrazine-functionalized peptides can be coupled to biomaterials in a single step at pH 5-6. In doing so, a degree of site-selectivity can be achieved over lysine residues present. This approach has been successfully implemented to conjugate reactive groups to alginate hydrogels, enabling indirect functionalization with growth factors and adhesion peptides.

In some embodiments, N-terminal modification of a biomolecule may be utilized for bioconjugation. For example, 2-pyridinecarboxaldehyde modified acrylamide hydrogels may react specifically with the N-terminus of ECM proteins, forming a cyclic imidazolidinone product with the adjacent amide bond and enabling the orientated display of these key bioinstructive motifs.

In some embodiments, acrylates, acrylamides, and methacrylates of a biomolecule or solid support may be utilized for bioconjugation. In some embodiments, thiol-ynes of a biomolecule or solid support may be utilized for bioconjugation.

In some embodiments, thiol-reactive conjugation such as native chemical ligation (NCL) can be utilized to attach peptides and proteins to biomaterial scaffolds via peptide bond formation. For example, a peptide having a C-terminal thioester reacts with an N-terminal cysteine residue in another peptide to undergo a trans-thioesterification reaction, which results in the formation of an intermediate thioester with the cysteine thiol.

In some embodiments, strong binding of (strept)avidin for the small molecule biotin may be used for bioconjugation. In some embodiments, (strept)avidin and biotin may be attached to a biomolecule and solid support (respectively or vice versa) for bioconjugation. In some embodiments, modification reagents can add a functional biotin group to proteins, nucleic acids, and other biomolecules. In some embodiments, depending on the functionality present on the biotinylation compound, specific reactive groups on antibodies or other proteins may be modified to create a (strept)avidin binding site. Amines, carboxylates, sulfhydryls, and carbohydrate groups can be specifically targeted for biotinylation through the appropriate choice of biotin derivative. In some embodiments, photoreactive biotinylation reagents are used to add non-selectively a biotin group to molecules containing no convenient functional groups for modification. In some embodiments, biotin-binding proteins can be immobilized onto surfaces, chromatography supports, microparticles, and nanoparticles for use in coupling biotinylated molecules. In some embodiments, a series of (strept)avidin-biotin interactions can be built upon each other to utilize the multivalent nature of each tetrameric (strept)avidin molecule and enhance the detection capability for the target. In some embodiments, amine-reactive biotinylation reagents that may contain reactive groups off biotin's valeric acid side chain are able to form covalent bonds with primary amines in proteins and other molecules. In some embodiments, NHS esters spontaneously react with amines to form amide linkages whereas carboxylate-containing biotin compounds can be coupled to amines via a carbodiimide-mediated reaction using EDC. In some embodiments, NHS-iminobiotin can be used to label amine-containing molecules with an iminobiotin tag, providing reversible binding potential with avidin or streptavidin. In some embodiments, Sulfo-NHS—SS-biotin (also referred to as NHS—SS-biotin) is sulfosuccinimidyl-2-(biotinamido)ethyl-1,3-dithio-propionate, a long-chain cleavable bio-tinylation reagent that can be used to modify amine-containing proteins and other molecules. In some embodiments, 1-biotinamido-4-[4'-(maleimidomethyl) cyclohexane-carboxamido]butane, a biotinylation reagent containing a maleimide group at the end of an extended spacer arm reacts with sulfhydryl groups in proteins and other molecules to form stable thioether linkages. In some embodiments, N-[6-(biotinamido)hexyl]-3'-(2'-pyridyldithio)propionamide where the reagent contains a 1,6-diaminohexane spacer group which is attached to biotin's valeric acid side chain, the terminal amino group of the spacer may be further modified via an amide linkage with the acid precursor of SPDP to create a terminal, sulfhydryl-reactive group. The pyridyl disulfide end of biotin-HPDP may react with free thiol groups in proteins and other molecules to form a disulfide bond with loss of pyridine-2-thione.

In some embodiments, a carboxylate of a biomolecule or solid support may be utilized for bioconjugation. In some embodiments, diazomethane and other diazoalkyl derivatives may be used to label carboxylate groups. In some embodiments, N,N'-Carbonyl diimidazole (CDI) may be used to react with carboxylic acids under nonaqueous conditions to form N-acylimidazoles of high reactivity. An active carboxylate can then react with amines to form amide bonds or with hydroxyl groups to form ester linkages. In addition, activation of a styrene/4-vinylbenzoic acid copolymer with CDI may be used to immobilize an enzyme lysozyme or other biomolecule through its available amino groups to the carboxyl groups on to a matrix.

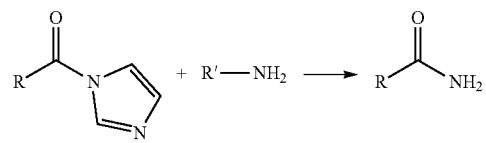

In some embodiments, carbodiimides function as zero-length crosslinking agents capable of activating a carboxylate group for coupling with an amine-containing compound for bioconjugation to a biomolecule or a solid support. In some embodiments, carbodiimides are used to mediate the formation of amide or phosphoramidate linkages between a carboxylate and an amine or a phosphate and an amine.

In some embodiments, N,N'-disuccinimidyl carbonate or N-hydroxysuccinimidyl chloroformate may be utilized in bioconjugation. N,N'-Disuccinimidyl carbonate (DSC) consists of a carbonyl group containing, in essence, two NHS esters. The compound is highly reactive toward nucleophiles. In aqueous solutions, DSC may hydrolyze to form two molecules of N-hydroxysuccinimide (NHS) with release of one molecule of $CO_2$. In nonaqueous environments, the reagent can be used to activate a hydroxyl group to a succinimidyl carbonate derivative. DSC-activated hydroxylic compounds can be used to conjugate with amine-containing molecules to form stable crosslinked products.

In some embodiments, sodium periodate can be used to oxidize hydroxyl groups on adjacent carbon atoms, forming reactive aldehyde residues suitable for coupling with amine- or hydrazide-containing molecules for bioconjugation. For example, these reactions can be used to generate crosslinking sites in carbohydrates or glyco-proteins for subsequent conjugation of amine-containing molecules by reductive amination.

In some embodiments, enzymes may be used to oxidize hydroxyl-containing carbohydrates to create aldehyde groups for bioconjugation. For example, the reaction of galactose oxidase on terminal galactose or N-acetyl-d-galactose residues proceeds to form C-6 aldehyde groups on polysaccharide chains. These groups can then be used for conjugation reactions with amine- or hydrazide-containing molecules.

In some embodiments, reactive alkyl halogen compounds can be used to specifically modify hydroxyl groups in carbohydrates, polymers, and other biomolecules for bioconjugation.

In some embodiments, an aldehyde or ketone of a biomolecule or solid support may be used for bioconjugation. For example, derivatives of hydrazine, especially the hydrazide compounds formed from carboxylate groups, can react specifically with aldehyde or ketone functional groups in target biomolecules. To further stabilize the bond between a hydrazide and an aldehyde, the hydrazone may be reacted with sodium cyanoborohydride to reduce the double bond and form a secure covalent linkage.

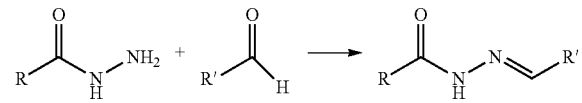

In some embodiments, an aminooxy group of a biomolecule or solid support may be used for bioconjugation. For example, the chemoselective ligation reaction that occurs between an aldehyde group and an aminooxy group yields an oxime linkage (aldoxime) that has been used in many bioconjugation reactions, as well as in the coupling of ligands to insoluble supports including surfaces. This reaction is also quite efficient with ketones to form an oxime called a ketoxime.

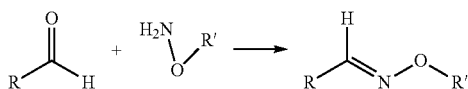

In some embodiments, cycloaddition reactions may be utilized for bioconjugation. In cycloaddition reactions for bioconjugation, two or more unsaturated molecules are brought together to form a cyclic product with a reduction in the degree of unsaturation, these reaction partners required can be absent from natural systems, and so the use of cycloadditions for conjugation requires the introduction of unnatural functionality within the biomolecule coupling partner.

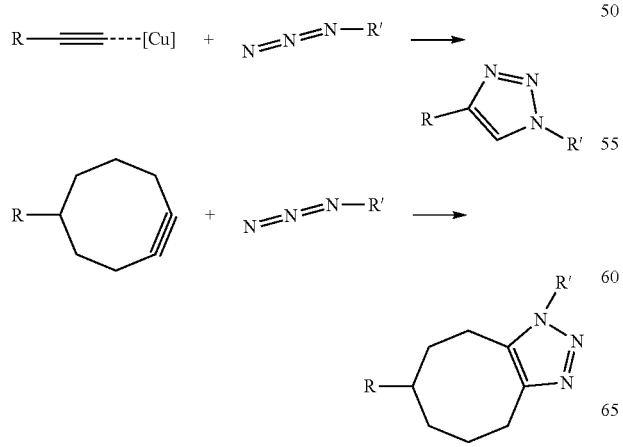

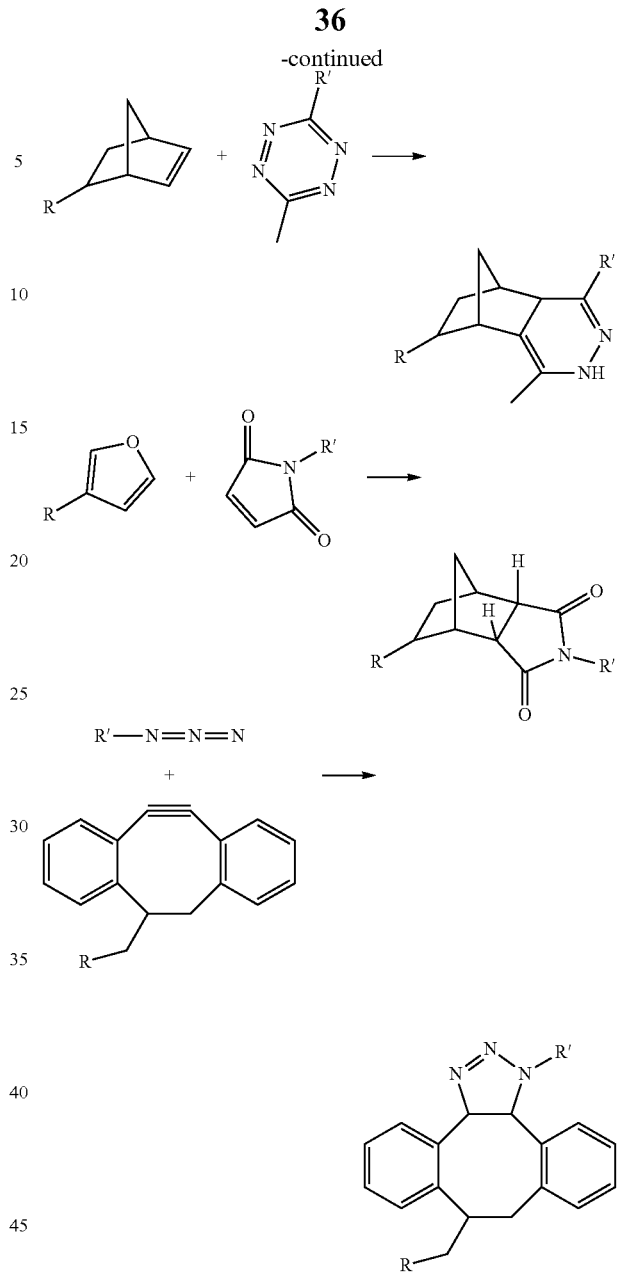

In some embodiments, Copper-Catalyzed Azide-Alkyne Cycloadditions may be utilized for bioconjugation. In some embodiments, the (3+2) cycloaddition between an azide and alkyne proceeds spontaneously at high temperatures (>90° C.), producing a mixture of two triazole isomers. In some embodiments, this reaction proceeds at room temperature, ambient, oxygenated, and/or aqueous environments. In some embodiments, for example, the formation of peptide-material conjugates by CuAAC, using alkyne-capped peptides to form hydrogels with azide-functionalized PEG. In some embodiments, CuAAC has been widely used to functionalize scaffolds with alkyne and azide functionalized peptides and carbohydrates, in part due to the ease with which the amino acids azidolysine and homopropargylglycine can be introduced by solid-phase peptide synthesis. In some embodiments, to achieve biomaterial conjugation via CuAAC, the required copper(I) catalyst can either be added directly, or generated in situ by reduction of an initial copper(II) complex, which may use ascorbic acid. The addition of a reducing agent further reduces the sensitivity of the CuAAC ligation to oxygen. Although no additional ligand is necessary for triazole formation, the addition of tertiary amine-based ligands may be used.

In some embodiments, Strain-Promoted Azide-Alkyne Cycloadditions (SPAAC) may be utilized for bioconjugation. In some embodiments, highly strained cyclooctynes react readily with azides to form triazoles under physiological conditions, without the need for any added catalyst. In some embodiments, in addition to the use of SPAAC for peptide conjugation, a number of prominent reports have used SPAAC to conjugate protein substrates to cyclooctyne functionalized biomaterials via the introduction of an unnatural azide motif into the protein coupling partner. In some embodiments, for example, this is achieved by including maleimide functionalization of native cysteines present in bone morphogenetic protein-2 (BMP-2), via enzyme-mediated N-terminal modification of IFN-γ, or via codon reassignment with the unnatural amino acid 4-azidophenyl-alanine in a number of protein substrates. In some embodiments, supramolecular host-guest interactions can also be used to promote azide-alkyne cycloaddition. For example, by bringing two reactive partners into close proximity within the cavity of a cucurbit[6]uril host, efficient cycloaddition may be achieved on the surface of proteins, this strategy may be extended to other appropriate biomolecules.

In some embodiments, inverse-electron demand Diels-Alder reactions (IEDDA) may be utilized for bioconjugation. For example, the inverse-electron demand Diels-Alder (IEDDA) reaction between 1,2,4,5-tetrazines and strained alkenes or alkynes may be employed. A wide range of suitable derivatives for undertaking biomolecule conjugation have been reported, for example, a series of increasingly strained (and thus reactive) trans-cyclooctenes may be utilized. In some embodiments, functionalized norbornene derivatives may be utilized for undertaking IEDDA reactions. In some embodiments, triazines may be utilized. In some embodiments, spirohexene may be utilized. These strategies may be extended to other appropriate biomolecules. In some embodiments, hetero-Diels-Alder cycloaddition of maleimides and furans may be utilized for bioconjugation. For example, the coupling of furan-functionalized RGDS peptides to maleimide-functionalized PEG-hydrogels may be utilized, this strategy may be extended to other appropriate biomolecules. In some embodiments, furan-functionalized hyraluronic acid hydrogels can be cross-linked with a dimaleimide-functionalized peptide via Diels-Alder cycloaddition. MMP-cleavable peptides enable the migration of seeded cancer through the gel.

In some embodiments, oxime and hydrazone formation may be utilized for bioconjugation. In some embodiments, the stable attachment of peptides and DNA to biomaterials via hydrazone formation can be achieved via difunctional cross-linking, this strategy may be extended to other appropriate biomolecules. In some embodiments, the attachment of ketone or aldehyde modified green fluorescent protein (GFP) or metallothionein to hydroxylamine-functionalized synthetic polymers may be extended to other appropriate biomolecules. For example, protein cross-linked hydrogels were produced through oxime modification at both the protein N- and C-termini.

In some embodiments, the Diels-Alder reaction consists of the covalent coupling of a diene with an alkene to form a six-membered ring complex for bioconjugation.

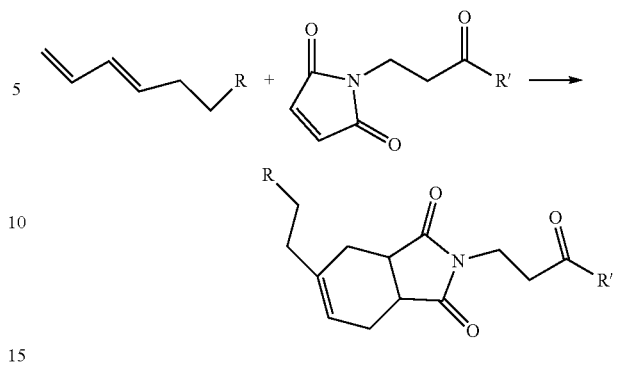

In some embodiments, transition metal complexes may be utilized for bioconjugation. The nature of late transition metals may make a transition metal complex well suited to the manipulation of unsaturated and polarizable functional groups (olefins, alkynes, aryl iodides, arylboronic acids, etc.). For example, Pd(O)-functionalized microspheres may mediate allyl carbamate deprotections and Suzuki-Miyaura cross-coupling in the cytoplasm. In other examples, a ruthenium catalyst may be used to mediate allyl carbamate deprotection of a caged fluorophore inside living cells. In some embodiments, applications of palladium-based applications in cell culture include copper-free Sonagashira coupling, extracellular Suzuki coupling on the surface of *E. coli* cells, and conjugation of thiol groups with allyl selenosulfate salts. In some embodiments, olefin metathesis may be utilized for bioconjugation. For example, with ruthenium complexes, S-allylcysteine can be easily introduced into proteins by a variety of methods, including conjugate addition of allyl thiol to dehydroalanine, direct allylation of cysteine, desulfurization of allyl disulfide, or metabolic incorporation as a methionine surrogate in methionine auxotrophic *E. coli*.

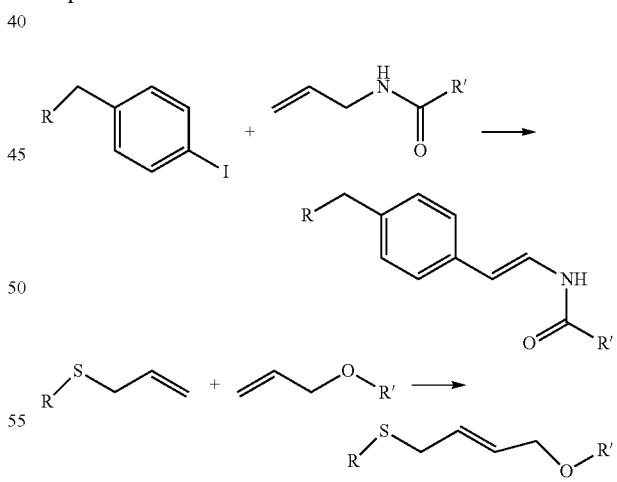

In some embodiments, complex formation with boronic acid derivatives may be used for bioconjugation. For example, boronic acid derivatives are able to form ring structures with other molecules having neighboring functional groups consisting of 1,2- or 1,3-diols, 1,2- or 1,3-hydroxy acids, 1,2- or 1,3-hydroxylamines, 1-2- or 1,3-hydroxyamides, 1,2- or 1,3-hydroxyoximes, as well as various sugars or biomolecules containing these species.

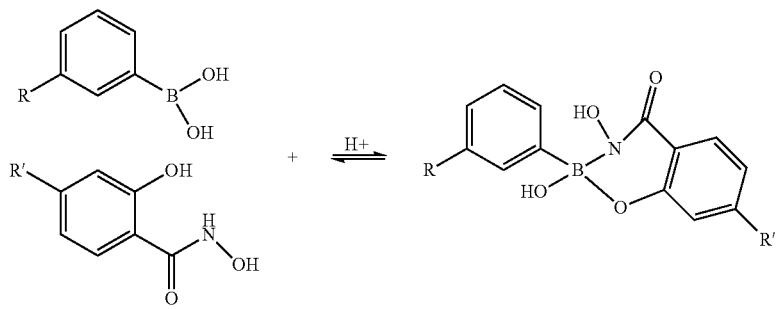

In some embodiments, enzyme-mediated conjugation may be utilized for bioconjugation. For example, the transglutaminase enzyme family catalyzes the formation of isopeptide bonds between the primary amine of lysine side chains and the amide bonds of a complementary glutamine residue, this strategy may be extended to other appropriate biomolecules. In other cases, peroxidase-mediated conjugation may be utilized for bioconjugation. For example, horse radish peroxidase (HRP) may be utilized to oxidize a wide range of organic substrates such as phenol group of tyrosine to generate a highly reactive radical or quinone intermediate that undergoes spontaneous dimerization, resulting in the formation of an ortho carbon-carbon bond between two tyrosine residues, this strategy may be extended to other appropriate biomolecules. In some embodiments, short peptide tags may be utilized for bioconjugation. These peptide tags may be as short as 5 amino acids long and may be appended to a peptide or protein substrate which allows for their subsequent modification.

In some embodiments, polymerization of low molecular weight monomers may be utilized for bioconjugation. Polymerization may be classified as proceeding via one of two mechanisms, either chain-growth or step-growth. During chain-growth polymerization, monomers are added at the "active" end of a growing polymer chain, resulting in the formation of high molecular weight materials even at low conversions. During step-growth polymerizations short oligomer chains couple to form polymeric species, requiring high conversions in order to reach high molecular weights. Both techniques can be used to form biomolecule-polymer conjugates. The polymerization of acrylate and methacrylate monomers has proven particularly fruitful. For example, acrylate and methacrylate modified peptides and glycans can be readily polymerized. Similarly, availability of the synthetic oligonucleotide phosphoramidite building block "Acrydite", free-radical polymerization remains a common method through which to form DNA and RNA functionalized biomaterials. By undertaking polymerization in the presence of a comonomer, the density of biomolecule presentation can be easily tuned, allowing potential difficulties from steric hindrance to be overcome. Initiation of polymerization can be triggered by a number of means, including heat, UV and visible light, redox reactions, and electrochemistry. Acrylate modified proteins can also undergo polymerization to produce functional materials, while retaining biological activity. In some embodiments, living radical polymerizations (LRPs) may be utilized for bioconjugation. For example, commonly used LRPs for the formation of bioconjugates include atom-transfer radical polymerization (ATRP), reversible addition-fragmentation chain transfer (RAFT) polymerization, and nitroxide-mediated polymerization (NMP).

In some embodiments, photoconjugation may be utilized for bioconjugation. In some embodiments, polymerization is initiated by the production of a radical species, which then propagates through bond formation to create an active polymer chain. The initiation step can be induced via a number of stimuli, with thermal decomposition, redox activation, and electrochemical ionization of an initiating species being common. Alternatively, many initiators can be activated via light-induced photolytic bond breakage (type I) or photoactivated abstraction of protons from a co-initiator (type II). Photoinitiation offers the benefits of being applicable across a wide temperature range, using narrow and tunable activation wavelengths dependent on the initiator used, rapidly generating radicals, and the ability to control polymerization by removing the light source. Importantly, the tolerance of polymerizations to oxygen is greatly enhanced, enabling polymerization in the presence of cells and tissues. The incorporation of acrylate-functionalized peptides and proteins during photopolymerization may be used as a method for producing biomaterial conjugates. Alternatively, the photoinitiated attachment of polypeptides to pendant vinyl groups on preformed materials has also been widely reported and more recently used for 3D patterning via two-photon excitation. A wide range of photoinitiators may be used in photoconjugation conjugations. For example but not limited to, Eosin Y, 2,2-dimethoxy-2-phenyl-acetophenone, Igracure D2959, lithium phenyl-2,4,6-trimethylbenzoylphosphinate, and riboflavin may be used as photoinitiators. Photoinitiators generally absorb light to initiate the photoreaction processes. In some embodiments, photoconjugation may utilize a photo thiol-ene reaction. Thiols can also react with alkenes via a free-radical mechanism. A thiol radical first reacts with an alkene to generate a carbon-centered radical, which can then abstract a proton from another thiol and thus propagate the reaction. Photo thiol-ene reactions may be accelerated by electron-rich alkenes, which generate unstable carbon-radical intermediates able to rapidly abstract thiol-hydrogens. Exceptions to this rule are norbornene derivatives, in which reactivity is driven instead by the release of ring strain upon thiol addition. This leads to a general trend in reactivity of norbornene>vinyl ether>propenyl>allyl ether>acrylate>maleimide. Norbornenes and allyloxycarbonyls (alloc groups) have been particularly widely used for peptide/protein-biomaterial functionalization, due to the almost negligible contribution of chain transfer and their ease of introduction during peptide synthesis, respectively. For example, an alloc group, which can be used as an orthogonal lysine protecting group during solid-phase peptide synthesis, is an efficient photo thiol-ene reactive handle. In other examples, norbornene photo thiol-ene reactions may be used for the tethering and spatial patterning of bioactive peptides and growth factor proteins. In addition to alloc and norbornene reactive groups, other alkenes have also been used for biomaterial functionalization. For example, codon reassignment has been used to site-specifically incorporate allyl-cysteine residues into proteins, which can subsequently undergo conjugation through the use of photo thiol-ene reactions. Alternatively, acrylates can undergo mixed-mode photopolymerizations in the presence of cysteine capped peptides, while allyl disulfide structures have recently been shown to undergo reversible and controlled exchange of conjugated thiols.

In some embodiments, aryl azide or halogenate aryl azides of a biomolecule or solid support may be utilized for bioconjugation.

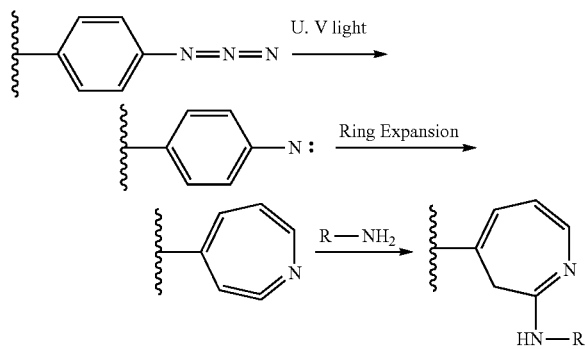

In some embodiments, photoreactive group benzophenone may be utilized for bioconjugation.

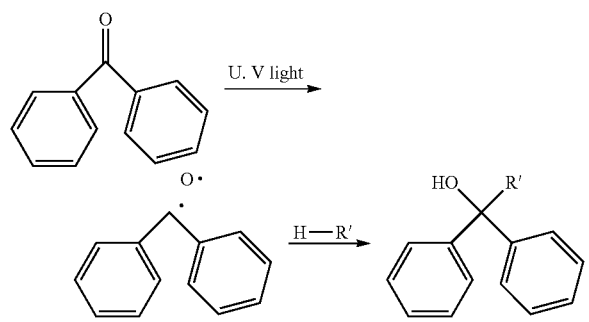

In some embodiments, photoreactive group anthraquinone may be utilized for bioconjugation.

In some embodiments, photo thiol-yne reactions may be utilized for bioconjugation. Most examples of photo thiol-yne reactions have exploited simple propargyl-ether or -amine reactive handles.

In some embodiments, photocaging and activation of reactive functionalities may be utilized for bioconjugation. Generally, a transient reactive species is formed whether it be an acrylate or thiol derived radical. In some embodiments, photocaging may be used to mask or protect a functional group until it is desirable for it to be exposed. In some embodiments, the most widely utilized cages are based around o-nitrobenzyl and coumarin chromophores. For example, nitrobenzyl-capped cysteine residues may be decaged by irradiation with 325 nm UV light, the released thiol may then react with maleimide-functionalized peptides via Michael addition, to generate a patterned hydrogel able to guide cell migration. In some embodiments, 6-bromohydroxycoumarins may be used for thiol-caging. In some embodiments, photoaffinitiy agents may be utilized for bioconjugation where a highly reactive intermediate upon irradiation, which then reacts rapidly with the nearest accessible functional group with high spatial precision. In some embodiments, commonly used are phenylazides, benzophenones, and phenyl-diazirines. In some embodiments, photocaged cycloadditions may be used. For example, the UV irradiation of tetrazoles has been shown to generate a reactive nitrile-imine intermediate which can undergo rapid cycloaddition with electron-deficient alkenes such as acrylates or acrylamides. In some embodiments, the nitrile-imine side-reactivity with thiols may be utilized for site-specifically conjugate cysteine containing proteins to tetrazole functionalized surfaces.

In some embodiments, noncovalent interactions may be utilized for bioconjugation. In some embodiments, noncovalent binding plays a vital role in cells, controlling biomolecular interfaces and influencing protein-protein interactions, DNA-DNA complexation, DNA-protein interfaces, protein localization, and more. In some embodiments, noncovalent sequences which display a binding affinity for the biomolecule of interest, allow for postfabrication modification or for native biomolecules to be simply sequestered from the surroundings within biological samples. Commonly used binding sequences are short peptides between 7 and 20 amino acids in length, derived from a variety of sources, including known protein binding domains present in vivo or determined through techniques such as phage display. In some embodiments, short oligonucleotides referred to as aptamers can also be used to bind a variety of protein substrates, including the cytokines vascular endothelial growth factor (VEGF) and platelet derived growth factor (PDGF), as well as cell surface proteins such as epidermal growth factor receptor (EGFR). In some embodiments, binding sequences can also be introduced into a biomaterial with affinity for native biopolymers, such as heparin. In some embodiments, by first inducing biopolymer binding, the adsorption of an added or endogenous growth factor or signaling protein to a biomaterial scaffold can then be controlled. In some embodiments, binding affinity at the amino acid level can also be exploited to enable peptide and protein conjugation to certain biomaterial substrates. For example, the binding of unnatural catechol-based amino acids can be used to induce binding to metal oxide containing bioglasses and metallic implants, enabling the bioactivity of these important technologies to be enhanced.

In some embodiments, self-assembling peptides may be utilized for bioconjugation. For example, native peptides and proteins adopt a series of secondary structures, including β-sheets and α-helices, which can both stabilize individual sequences and control interprotein aggregation. In some embodiments, self-assembling peptides have been used extensively to assemble hydrogels and fibrous materials. In many of these structures, biological epitopes or functional groups can be appended to some or all of the peptide building blocks during peptide synthesis, to add the desired bioactivity into the system. Peptide-ligands ranging from simple adhesion motifs, to laminin derived epitopes, and growth factor mimetics have all been displayed on the surface of self-assembled fibrils. Alternatively, glycopeptides can be assembled in order to recruit extracellular signaling proteins and growth factors, mimic glycosylation patterns within hyaluronic acid, or investigate optimal sulfonation ratios in glycosaminoglycan scaffolds. In some embodiments, self-assembling domains can also be added to full-length proteins, leading to the incorporation of pendant functionality during hydrogel formation. In some embodiments, the propensity of peptides to form secondary structures has also been exploited within nonself-assembling scaffolds. This may be achieved by mixing a self-assembling peptide into a covalent hydrogel, composed of either a noninteracting polymer such as interpenetrating networks of PEG or systems where additional charge interactions further stabilize the final construct, for example between positively charged peptides and negatively charged alginate gels. As an alternative, pendant helical groups can be attached to a covalent material and used to drive the noncovalent attachment of bioactive groups such as growth factors via self-assembly into coiled-coil triple helices.

In some embodiments, host-guest chemistry may be utilized for bioconjugation. For example, the adhesive properties of a β-cyclodextrin modified alginate scaffold may be controlled in situ through the addition of a guest naphthyl-functionalized RGDS peptide and by subsequently introducing a non-cell adhesive adamantane-RGES peptide with a higher host binding constant, dynamic modulation of fibroblast cell attachment was enabled. Host-guest interactions between cyclodextrin and naphthyl- or adamantane-functionalized peptides allow alginate functionalization, this may be applied to other appropriate biomolecules.

In some embodiments, biotin-(strept)avidin may be utilized for bioconjugation. For example, avidin and streptavidin are homotetrameric proteins that can simultaneously bind up to four molecules of their small molecule binding partner biotin. The small size of biotin (with a mass of just 244 Da) and the ease with which it can be functionalized via its free carboxylic acid has led to biotin-(strept)avidin binding finding widespread use as a means to undertake biomaterial conjugation. Streptavidin-protein fusions can be produced recombinantly and bound to suitably functionalized surfaces to achieve conjugation. In some embodiments, biomolecule biotinylation is undertaken, and this construct is then bound to a (strept)avidin functionalized surface. In some embodiments, this can either be achieved by a direct route, via chemical preconjugation of the material with (strept)avidin, or by exploiting the tetrameric binding of (strept)avidin to mediate indirect modification or cross-linking of biotin-functionalized scaffolds.

In some embodiments, nucleic acids may be utilized for bioconjugation. In some embodiments, in an analogous fashion to self-assembling peptides, nucleic acids (e.g., SNAPs) can also form assembled materials themselves, to generate tunable platforms for the display of biomolecules. In some embodiments, protein-nucleic acid conjugates (e.g., DNA-tagged peptides) can be conjugated to a suitably functionalized solid support or other material. In some configurations the nucleic acid moiety of the protein-nucleic acid conjugate attaches to the solid support or other material. Alternatively or additionally, the protein moiety of the protein-nucleic acid conjugate can attach to the solid support or other material.

Generally, incorporating reactive handles may be utilized for bioconjugation. For example, introducing uniquely reactive motifs into biomolecule substrates provides a chemical "tag" which allows single-site selectivity or specificity to be achieved. In some embodiments, short peptides and oligonucleotides can be produced via solid phase synthesis (SPS). The versatility of organic synthesis allows difficulties in reactive handle incorporation to be overcome, with a wide range of suitably functionalized amino acids and oligonucleotides available as described herein. In some embodiments, an alternative approach is to introduce unnatural amino acids (UAAs) bearing the desired reactive handles. This may be achieved via the modification of lysine residues with amine-reactive derivatives. In some embodiments, the use of auxotrophic bacterial strains, which are unable to biosynthesize a particular amino acid and thus require uptake from the growth media, by starving the bacteria of the native amino acid and supplementing it with a structurally related unnatural analogue, the bacterial cells may incorporate the UAA during translation. This technique may be used to install azide- and alkyne-based mimics of methionine, leading to the introduction of reactive handles for undertaking CuAAC and SPAAC reactions. Analogous strategies can be used for the incorporation of unnatural monosaccharides, enabling the remodeling of complex glycans. In some embodiments, the use of codon reassignment using orthogonal tRNA and tRNA synthetase pairs that selectively recognize and charge an UAA during translation. In some embodiments, this may be achieved by reassigning the amber stop-codon, UAG, by incorporating a tRNACUA/tRNA synthetase pair from an alternative kingdom into the host cell. This pair may be able to install the desired UAA, while being effectively invisible to the endogenous cell machinery. As a result, site-directed mutagenesis can be used to introduce a single TAG codon at the desired position of the coding DNA, leading to the singular introduction of the UAA with high specificity and selectivity.

In some embodiments, one or more functional groups may release a reporter when reacted with another functional group, or with a SNAP or biological entity, chemical, or physical entity. Having a reporter released when the SNAP and biological, chemical, or physical entity are conjugated may allow tracking of the reaction. In some embodiments, it may be possible to monitor the degree of completion of a SNAP-biological/chemical entity conjugation reaction by monitoring the concentration of free reporter. In some embodiments, the reporter may fluoresce once released by the conjugation reaction.

In some embodiments, the biological, chemical, or physical entity may be functionalized with a linker. In some embodiments, functionalizing the biological, chemical, or physical entity with a linker may decrease steric hindrance. A linker may comprise a rigid or semi-rigid moiety which can hold the biological, chemical, or physical entity away from the SNAP. In some embodiments, the linker may be a long, moderate or short linker. In some embodiments, the linker may comprise one or more component selected from PEG, DNA, short carboxyl, carbon chain, peptoid, spacer, and/or glycer, among other examples.

In some embodiments, the SNAPs, seeds, and/or biological, chemical, or physical entities may be functionalized using single pot proteomics methods. Single pot proteomics methods may result in very high efficiency of functionalization. In some embodiments, single pot proteomics methods may be useful to functionalize biological, chemical, or physical entities with very low levels of loss of the entities.

In some embodiments, a SNAP is a polymer which may be grown from a seed. For example if the seed is a DNA oligonucleotide then the SNAP may be a DNA molecule that is produced by extension of the oligonucleotide (e.g., via polymerase catalyzed addition of one or more nucleotides) or ligation to the oligonucleotide (e.g., via ligase catalyzed addition of one or more nucleic acids). In some embodiments, the SNAP may be a DNA molecule with regions of internal complementarity such that the molecule may self-hybridize. For example, the SNAP may be a DNA cluster, formed by self-hybridization within the molecule. In some embodiments, the SNAP may be formed from DNA, RNA, L-DNA, L-RNA, LNA, PNA, or a mixture of two or more different types of nucleic acid. In some embodiments, the SNAP may have a repeating structure, such as a repeating sequence of nucleotides or a concatemer of template copies (e.g., produced by rolling circle amplification of a circular template). In some embodiments, the SNAP may lack a repeating sequence of longer than about 25, 50, 100, 500 or 1000 nucleotides. For example, the SNAP may comprise a random sequence of nucleotides.

In some embodiments, a SNAP may be formed by rolling circle amplification. A plasmid, or other circular nucleic acid molecule, may be provided as a template, together with a primer that binds to the circular nucleic acid molecule, wherein said primer comprises a functional group on or near the 5' end. Performing a polymerase chain reaction (PCR) with a sufficiently long extension step, or merely a polymerase extension reaction, may allow the functionalized primer to bind the circular nucleic acid molecule and produce a single stranded nucleic acid product. The length of the single stranded nucleic acid product may be influenced by altering the extension time, the polymerase enzyme used, or the reaction conditions. In some embodiments, the circular nucleic acid template contains regions of internal complementarity, such that the single stranded nucleic acid product may contain regions which may self-hybridize. In some embodiments, the circular nucleic acid template is a double stranded DNA (dsDNA) molecule. In some embodiments, the single stranded nucleic acid product is a single stranded DNA (ssDNA) molecule. In some embodiments, the polymerase used is a DNA polymerase. In some embodiments, a plurality of SNAPs may be attached or bound together to produce a larger SNAP. In some embodiments, two SNAPs may be attached or bound together to produce a larger SNAP. In some embodiments, three or more SNAPs may be attached or bound together to produce a larger SNAP.

In some embodiments, a SNAP may be formed by nucleic acid origami, or DNA origami. DNA origami generally refers to the nanoscale folding of DNA to create non-arbitrary two- and three-dimensional shapes at the nanoscale. The specificity of the interactions between complementary base pairs can make DNA a useful construction material. In some embodiments, the interactions between different regions may be controlled through design of the base sequences. DNA origami may be used to create scaffolds that hold other molecules in place or to create structures all on its own. Nucleic acid origami can be made and used, for example to attach analytes to a solid support.

SNAPs as described herein can include those created via nucleic acid origami. Optionally, nucleic acid origami can refer to DNA origami, RNA origami, origami of a combination of DNA and RNA molecules, or origami of nucleic acid analogs of DNA or RNA, such as a silicon-based nucleic acid, among other examples. Nucleic acid origami can result in a nucleic acid molecule which has an engineered shape. The engineered shape can be a shape which has been partially or fully planned. The planning of the shape can comprise planning or engineering what sections of nucleic acid bind, where a segment of nucleic acid can fold, where a segment of nucleic acid can be single stranded, where a segment of nucleic acid can be double stranded, where a segment of nucleic acid can be bound to a segment of nucleic acid of the same strand, or where a segment of nucleic acid can be bound to a segment of nucleic acid on another strand. In some embodiments, non-nucleic acid molecules, such as protein, can be used to encourage nucleic acid into the engineered shape. See, for example, U.S. Pat. No. 7,598,363 or 7,842,793, each of which is incorporated herein by reference.

Generally, nucleic acid origami can comprise at least one long nucleic acid strand and one or more short nucleic acid strands. The long strand, which can be called a 'scaffold', can be linear (i.e., having a 3' end and/or 5' end) or circular (i.e., lacking ends). The short strands can be referred to as 'staples' due to their role in maintaining tertiary and quaternary folding of the scaffold and overall origami shape. In some embodiments, the long and short nucleic acid strands are single stranded, although they can have segments which can be double stranded. One of the short strands can comprise at least a first segment which can be complementary to a first segment of the long strand, as well as a second segment which can be complementary to a second segment of the long strand. When the short and long strands are incubated under conditions that can allow hybridization of nucleotides, the shorter oligonucleotide can hybridize with the longer oligonucleotide. This hybridization can give shape to the nucleic acid molecule. For example, if the two segments on the first strand are separated, then these two segments can be brought together during hybridization to create a shape. In some embodiments, a short strand can bind to at least 2, 3, 4, 5, or 6 segments which can bind to at least 2, 3, 4, 5, or 6 complementary segments of the long nucleic acid strand.

In some embodiments, a short strand can have one or more segments which can be non-complementary to the long strand. In such a case, the segment which is not complementary to the long strand can be at least about 1, 2, 3, 4, 5, 10, 15, or 20 nucleotides long.

This process can be performed with at least about 1, 2, 3, 4, 5, 6, 7, 8, 9, 10, 15, 20, 30, 40, 50, 60, 70, 80, 90, 100, 150, 200, 250, 300, or more short nucleic acid strands. These short nucleic acid strands can each bind to one or more different segments of the long nucleic acid strand. Each short nucleic acid strand which hybridizes to the long nucleic acid strand can lead to a fold in the long nucleic acid strand. In some embodiments, the number of short strands can be correlated with the complexity of the engineered shape. For example, an engineered shape with many folds can utilize more short nucleic acid strands than an engineered shape with few folds. An engineered shape can have at least about 1, 2, 3, 4, 5, 6, 7, 8, 9, 10, 15, 20, 30, 40, 50, 60, 70, 80, 90, 100, 150, 200, 250, 300, or more folds.

In some embodiments, more than one long strand can be incorporated into the nucleic acid origami structure. This can be done for example to increase the complexity of the engineered shape, to ease the designing or planning of the engineered shape, to avoid the creating of a shape which is more thermodynamically stable than the desired engineered shape, to make the creation of the engineered shape easier, or to manage costs of creating the engineered shape.

Incorporation of more than one long strand can be accomplished by designing the 2 or more long strands such that each strand has at least one segment that can be complimentary to a segment of the other strand, or by designing the 2 or more long strands such that each has at least one segment which can be complementary to a region of a short nucleic acid strand, such that both long strands have segments complementary to the short nucleic acid strand.

Short nucleic acid strands can have complementarity to one long nucleic acid strand or more than one long nucleic acid strand. In some embodiments, a short nucleic acid strand can also have complementarity to one or more short nucleic acid strands.

The terms "long" and "short" herein are meant to be relative terms. A long strand can be longer than a short strand. In some embodiments, a long strand can be at least about 30, 40, 50, 100, 150, 200, 250, 300, 400, 500, 600, 700, 800, 900, 1000, or more nucleotides long. A short strand can be shorter than a long strand. In some embodiments, a short strand can be at least about 6, 7, 8, 9, 10, 15, 20, 25, 30, 35, 40, 45, 50, 60, 70, 80, 90, 100, or more nucleotides long. Alternatively or additionally, a short strand can be at most about 500, 100, 50, 40, 30, 20, 10 or fewer nucleotides long.

An engineered shape can be designed for a specific purpose. For example, an engineered shape can be designed to support a load, encapsulate a molecule, bind a molecule, connect two or more molecules, fit into a well or cavity, bind a protuberance, or other purpose. An engineered shape can be any shape, such as oblong, rectangular, round, circular, spherical, flat, textured, smooth, symmetrical, asymmetrical, conical, or irregular. An engineered shape can be a cube, pyramid, box, cage, ladder, or tree.

An engineered shape or SNAP formed via nucleic acid origami as described above can be assembled. Assembly can refer to the process by which the nucleic acid strands hybridize to each other to create the engineered shape.

An engineered shape or SNAP can be spontaneously self-assembling. Self-assembly can occur when long and short oligonucleotides having regions which can be complimentary are incubated together. During spontaneous self-assembly, the nucleotides can hybridize and the engineered shape can be created during incubation without the help of a helper molecule or catalyst. Such self-assembling can occur under specific conditions or a range of specific conditions. Conditions which can be considered when incubating DNA strands for self-assembly can be salt concentration, temperature, and time.

Sometimes, assembly can utilize or require a catalyst. In such cases, the catalyst can speed up assembly or ensure the assembly results in a particular desired engineered shape. A catalyst can comprise RNA, DNA, or protein components.

The salt concentration during assembly can be less than 1 M, less than 0.5M, less than 0.25 M, less than 0.1M, less than 0.05 M, less than 0.01 M, less than 0.005 M, or less than 0.001 M.

The temperature during assembly can be at least room temperature. In some embodiments, the temperature during assembly can be at least about 50, 60, 70, 80, 85, 90, or 95° C. In some embodiments, the temperature during assembly can vary. For instance, the temperature can be increased to at least about 20, 30, 40, 50, 60, 70, 80, 85, 90, or 95° C. This increase can ensure the nucleic acid strands do not comprise a secondary structure prior to assembly. Once the temperature is increased as described, it can be decreased, for example to about 20, 30, 40, 50, 60, 70, or 80° C. This decrease in temperature can allow the nucleic acids to hybridize. In some embodiments, the decrease in temperature can occur over about 0.5, 1, 2, 3, 4, 5, 10, 15, 20, 25, 30, 45, or 60 minutes.

Assembly can be performed stepwise. In such cases, a subset of the nucleic acid molecules can be incubated together first. After these molecules are allowed to hybridize, one or more additional nucleic acid molecules can be added and allowed to hybridize. In some embodiments, two or more engineered shapes which have been assembled can be incubated together for assembly into a larger engineered shape.

In some embodiments, assembly can comprise fractal assembly. Fractal assembly can create a SNAP which can be an array of engineered shapes. Assembly can occur in stages, which can simplify the design process or ensure correct assembly. Such an array can be assembled in at least 1, 2, 3, 4, 5, 10, 15, 20, 30, 40, 50, 60, 70, 80, 90, 100, 200, 300, 400, 500, 1000, or more stages. In some embodiments, the number of stages used can correlate with a reduction of spurious interactions. This can be due to a reduction in the total number of possible reactions at any given time.

SNAPs can be assembled into an array which can be at least 3×3, at least 5×5, at least 10×10, at least 50×50, at least 100×100, or at least 1000×1000 (engineered shapes×engineered shapes).

Each hybridization reaction can take about 10, 20, 30, 40, 50, or 60 seconds. In some embodiments, each hybridization reaction can take about 1, 2, 3, 4, 5, 10, 15, 20, 30, 40, 50, or 60 minutes. In some embodiments, a hybridization reaction can take more than 1 hour.

Nucleic acid origami may be used to preferentially influence how the SNAP will "land" on the solid support. For example, nucleic acid origami may be used to construct a SNAP with a landing surface that can preferentially contact the solid support, A SNAP such as one made via nucleic acid origami can be designed to comprise a region that can create steric or electrostatic interactions with the support to influence the orientation of the SNAP on the support. For example, the region can comprise nucleotides having modifications e.g., to the backbone of the nucleic acid which can promote interaction between the SNAP and the solid support. In further examples, the region can comprise protuberances or cavities which can "fit" to cavities or protuberances on the solid support. In some embodiments, the support surface can comprise chemical structuring (e.g., nanoparticles or oligonucleotides), click reagents, or other rationally designed materials that can influence the position and orientation of SNAP structures, including SNAPs synthesized via nucleic acid origami.

Nucleic acid origami can be used to construct a SNAP with a linker which can attach a biological, chemical, or physical entity, wherein said linker is positioned relative to the landing surface such that the biological, chemical, or physical entity can be distal or approximately distal to the solid support. The linker may also comprise a region of dsDNA to force a rigid outpost from the SNAP. In some embodiments, protein origami may also be used.

A surface can have properties such that a SNAP can bind to the surface in such a way that it can flop or lean. The SNAP can flop or lean to the left, to the right, to the front, to the back, or to any combination of sides thereof. The SNAP can flop or lean once and remain in place, or it can flop freely between sides over time. In some embodiments, the SNAP can preferentially flop in one direction over one or more other directions. In some embodiments, the SNAP can preferentially avoid flopping in a particular direction.

In some embodiments, for example, filamentous or stranded molecules, such as nanoparticles or oligonucleotide strands, can be attached to a surface. A SNAP, which can comprise an engineered shape, can comprise one or more moieties which can bind to a filamentous or stranded molecule, such as a dangling single stranded oligonucleotide or nanoparticle. Upon contacting the surface with such SNAPs, the one or more moieties can interact with one or more of the filamentous or stranded molecules. In some embodiments, the moieties can bind tightly to the filamentous or stranded molecules. The SNAPs can be removable or non-removable in such cases.

Computational modeling or simulation tools may be employed to design and optimize oligonucleotide or protein sequences to create particular SNAP structures.

In some embodiments, a SNAP may be, or may include, a nucleic acid plasmid, such as a DNA plasmid. Plasmids may exist in a compact form referred to as supercoiled DNA. The radii of a supercoiled plasmid may be determined by the plasmid size—i.e., a plasmid with a longer backbone may form a larger supercoiled entity. In some embodiments, a SNAP may comprise a plasmid with a backbone of between 5 kb and 150 kb. In some embodiments, a SNAP may comprise a plasmid with a backbone of between 5 kb and 100 kb. In some embodiments, a SNAP may comprise a plasmid with a backbone of between 5 kb and 90 kb. In some embodiments, a SNAP may comprise a plasmid with a backbone of between 25 kb and 50 kb. In some embodiments, a SNAP may comprise a plasmid with a backbone of at least about 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 105 kb, 110 kb, 115 kb, 120 kb, 125 kb, 130 kb, 135 kb, 140 kb, 145 kb, or 150 kb. In some embodiments, SNAPs may be imaged using an imaging platform, such as Nanocyte or Leica In some embodiments, a SNAP may have a branched structure. For example the SNAP may be a dendrimer. Some examples of dendrimers may be found in Newkome, George R., and Carol D. Shreiner. "Poly (amidoamine), polypropylenimine, and related dendrimers and dendrons possessing different 1->2 branching motifs: an overview of the divergent procedures." Polymer 49.1 (2008): 1-173. A dendrimer used with the methods of this disclosure may be a G1, G2, G3, G4, G5, G6, G7, G8, G9, G10, G11, G12, G13, G14, or G15 dendrimer. In some embodiments, the dendrimer may be higher than a G15 dendrimer, for example dendrimer between G15 and G30.

In some embodiments, the SNAP may include one or more proteins. For example the SNAP may include a protein fibril. The SNAP may be comprised of proteins known to form into fibrils, such as, for example, the tau protein, or portions of the tau protein. A 31-residue portion of tau which assembles into fibrils is described by, for example, Stöhr, Jan, et al. "A 31-residue peptide induces aggregation of tau's microtubule-binding region in cells." Nature chemistry 9.9 (2017): 874, which is incorporated herein by reference. In some embodiments, the SNAP may comprise tetratricopeptide repeats. Examples of tetratricopeptide repeats may be found in Blatch, Gregory L., and Michael Lassle. "The tetratricopeptide repeat: a structural motif mediating protein-protein interactions." Bioessays 21.11 (1999): 932-939. Other examples of proteins which may assemble may be found in Speltz, Elizabeth B., Aparna Nathan, and Lynne Regan. "Design of protein-peptide interaction modules for assembling supramolecular structures in vivo and in vitro." ACS chemical biology 10.9 (2015): 2108-2115.

In some embodiments, the SNAP may be made, used, or observed as a single-molecule. In some embodiments, the SNAP may not be made, used, or observed as a single-molecule. For example, the SNAP may be a member of a plurality of SNAPs that are made, used, or observed as an ensemble. In some embodiments, the SNAP may be assembled from several molecules which bind non-covalently. For example the SNAP may be formed from two or more nucleic acid molecules which hybridize together. In another example the SNAP may be formed from two or more protein molecules which assemble together via non-covalent bonds.

In some embodiments, the SNAPs are between about 50 nm and about 100 um in diameter.

The SNAPs are generally polymeric molecules. These may be grown through a controlled polymerization reaction, a stepwise polymerization reaction, or a step by step synthesis method. The growth of the SNAPs may be controlled by the amount of monomers available, the length of time the reaction is allowed to proceed, or the number of synthesis steps performed.

Each SNAP may have a diameter of at least about 10 nanometers (nm), 50 nm, 75 nm, 100 nm, 150 nm, 200 nm, 300 nm, 400 nm, 500 nm, 600 nm, 700 nm, 800 nm, 900 nm, 1000 nm, 1500 nm, 2000 nm, 3000 nm, 4000 nm, 5000 nm, 6000 nm, 7000 nm, 8000 nm, 9000 nm, 10 µm, 20 µm, 30 µm, 40 µm, 50 µm, 75 µm, 100 µm, 200 µm, 300 µm, 400 µm, 500 µm, or more. In some embodiments, the SNAP may have a diameter between about 100 nm and 500 nm, between about 200 nm and about 400 nm, between about 500 nm and about 10 µm, or between about 1000 nm and about 10 µm.

SNAPs may be attached to a solid support (e.g., a site in an array) using crosslinkers, conjugation chemistries or binding components. In some embodiments, the SNAPs may be covalently attached to the solid support using a click chemistry. Generally, the term "click chemistry" is used to describe reactions that are high yielding, wide in scope, create only byproducts that can be removed without chromatography, are stereospecific, simple to perform, and can be conducted in easily removable or benign solvents, as described by, for example, (McKay, C., & Finn M. G. (2014) Click Chemistry in Complex Mixtures Bioorthogonal Bioconjugation vol 21, Issue 9, pp 1075-1101; M. G. Meldal, M., & Tornøe, C. W. (2008). Cu-Catalyzed Azide-Alkyne Cycloaddition. Chemical Reviews, 108(8), 2952-3015; Lutz, J., & Zarafshani, Z. (2008), which is incorporated herein by reference. Efficient construction of therapeutics, bioconjugates, biomaterials and bioactive surfaces using azide-alkyne "click" chemistry. Advanced Drug Delivery Reviews, 60(9), 958-970, which is incorporated herein by reference).

In some embodiments, the click chemistry reaction may be a CuAAC, SPAAC, SPANC, or as described elsewhere herein. In some embodiments, the click chemistry reaction may need a copper source such as, for example, $CuSO_4$, Cu(0), $CuBr(Ph_3P)_3$, CuBr, $CuBr/Cu(OAc)_2$, $CuBr_2$, [Cu (CH3CN)4]PF6, PS—NMe2:CuI, silica:CuI, (EtO)3P:CuI, CuCl/Pd2(dba)3, CuBF4, CuCl, CuCl2, Cu(AcO)2, Cu(2), TTA:CuSO4, Cu(1) zeolite (USY), Cu(CH3CN)4OTf, CuOTf, Cu(2):bis-batho, or a combination thereof. In some embodiments, a copper source is not needed for the click chemistry reaction to proceed. In some embodiments, the reducing agent of the click chemistry reaction may be, for example, NaAsc, air, ICl, oxygen, $N_2$, HAsc, TCEP, dithiothreitol (DTT), $PPh_3$, mercaptoethanol, tris(2-carboxyethyl)phosphine (TCEP), TCEPT-hydrochloric acid a combination thereof, or no reducing agent. In some embodiments, the solvent of the click chemistry reaction may be, for example, THF, pyridine, DMSO, DMF, toluene, NMP, acetonitrile, water, tBuOH, iBuOH, EtOH, MeOH, dioxane, dichloromethane, HEPES, NaCl buffer, acetone, PBS, SFM, Tris buffer, borate buffer, PB, TFH, AcOEt, PIPES, urea, acetone, Tris, saline, $AllOCO_2Me$, TMS-$N_3$, urea solution, bicarbonate buffer, a combination thereof, or no solution. In some embodiments, the base of the click chemistry reaction may be, for example, DIPEA, Lut Na2CO3, $iPr_2NH$, DBU, $Et_3N$, $Et_3N$ HCl, $Et_3NH+$-OAc, $K_2CO_3$, TBAF, $CuSO_4$, PS—$NMe_2$, piperidine, a desired pH, or a combination thereof. In some embodiments, the ligand of the click chemistry reaction may be, for example, TBTA, proline, BMAH, Lut, chiral Lig's, pyridine, His, Batho, TTA, Bim, Phen, Bipy, PMDETA, dNbipy, TRMEDA, or a combination thereof. In some embodiments, the temperature of the click chemistry reaction may be, for example, 0-5° C., 5-15° C., 15-25° C., 20-25° C., 25-35° C., 35-45° C., 45-55° C., 55-65° C., 65-75° C., 75-85° C., 85-95° C., or greater. In some embodiments, the temperature of the click chemistry reaction may be less than 0° C. In some reactions, the click chemistry reaction may be covered by aluminum foil. In some embodiments, the click chemistry reaction may include an acid, for example, trifluoroacetic acid, trichloroacetic acid, or tribromoacetic acid.

In some embodiments, a crosslinker may be used for conjugation. In some embodiments, the crosslinker may be a zero-length crosslinker, homobifunctional crosslinker, heterobifunctional crosslinker, or a trifunctional cross linker. Crosslinkers may be incorporated into a biomolecule preformed or in-situ.

In some embodiments, zero-length crosslinkers mediate the conjugation for bioconjugation by forming a bond containing no additional atoms. Thus, one atom of a molecule is covalently attached to an atom of a second molecule with no intervening linker or spacer. In such conjugation schemes, the final complex is bound together by virtue of chemical components that add foreign structures to the substances being crosslinked. Carbodiimides may be used to mediate the formation of amide linkages between carboxylates and amines or phosphoramidate linkages between phosphates and amines and are popular type of zero-length crosslinker that may be used, being efficient in forming conjugates between two protein molecules, between a peptide and a protein, between an oligonucleotide and a protein, between a biomolecule and a surface or particle, or any combination of these with small molecules. In some embodiments, EDC (or EDAC; 1-ethyl-3-(3-dimethylaminopropyl) carbodiimide hydrochloride) may be used for conjugating biomolecules containing carboxylates and amines. In some embodiments, CMC, or 1-cyclohexyl-3-(2-morpholinoethyl) carbodiimide (usually synthesized as the metho p-toluene sulfonate salt), is a water soluble reagent used to form amide bonds between one molecule containing a carboxylate and a second molecule containing an amine that may be used as a crosslinker for bioconjugation. In some embodiments, DIC, or diisopropyl carbodiimide may be used for bioconjugation as a zero-length crosslinker. In some embodiments, DCC (dicyclohexyl carbodiimide) may be used for bioconjugation as a zero-length crosslinker. In some embodiments, Woodward's reagent K is N-ethyl-3-phenylisoxazolium-3'-sulfonate, a zero-length crosslinking agent able to cause the condensation of carboxylates and amines to form amide bonds. In some embodiments, CDI, or N,N'-carbonyl diimidazole may be used for bioconjugation as a zero-length crosslinker. In some embodiments, Schiff base formation and reductive amination may be used for bioconjugation as a zero-length cross linker.

In some embodiments, homobifuctional crosslinkers mediate the conjugation for bioconjugation. In some embodiments, homofunctional NHS esters may be used for bioconjugation. For example, Lomant's reagent [(dithiobis (succinimidylpropionate), or DSP]) is a homobifunctional NHS ester crosslinking agent containing an eight-atom spacer 12 Å in length. The sulfo-NHS version of DSP, dithiobis(sulfosuccin-imidylpropionate) or DTSSP, is a water soluble analog of Lomant's reagent that can be added directly to aqueous reactions without prior organic solvent dissolution. In some embodiments, disuccinimidyl suberate (DSS), an amine-reactive, homobifunctional, NHS ester, crosslinking reagent produces an eight-atom bridge (11.4 Å) between conjugated biomolecules. In some embodiments, disuccinimidyl tartarate (DST), a homobifunctional NHS ester crosslinking reagent that contains a central diol that is susceptible to cleavage with sodium periodate may be used forms amide linkages with α-amines and F-amines of proteins or other amine-containing molecules. In some embodiments, BSOCOES [bis[2-(succinimidyloxycarbonyloxy) ethyl] sulfone], a water-insoluble, homobifunctional NHS ester crosslinking reagent that contains a central sulfone group, where the two NHS ester ends are reactive with amine groups in proteins and other molecules to form stable amide linkages. In some embodiments, ethylene glycolbis (succinimidylsuccinate) (EGS), a homobifunctional crosslinking agent that contains NHS ester groups on both ends. The two NHS esters are amine reactive, forming stable amide bonds between cross-linked molecules within a pH range of about 7 to 9. In some embodiments, disuccinimidyl glutarate (DSG), a water-insoluble, homobifunctional crosslinker containing amine-reactive NHS esters at both ends, may be used for biconjugation. In some embodiments, N,N'-Disuccinimidyl carbonate (DSC), the smallest homobifunctional NHS ester crosslinking reagent available may be used. In some embodiments, Dimethyl adipimidate (DMA), Dimethyl pimelimidate (DMP), Dimethyl suberimidate (DMS), dimethyl 3,3'-dithiobispropionimidate (DTBP), 1,4-di-[3'-(2'-pyridyldithio)propionamido] butane, bismaleimidohexane, 1,5-difluoro-2,4-dinitrobenzene or 1,3-difluoro-4,6-dinitrobenzene, DFDNPS (4,4'-difluoro-3,3'-dinitrophenylsulfone), Bis-[β-(4-azidosalicylamido)ethyl] disulfide (BASED), formaldehyde, Glutaraldehyde, 1,4-butanediol diglycidyl ether, adipic dihydrazide, carbohydrazide, 3,3'-dimethylbenzidine, p-diaminodiphenyl, or haloacetyl derivatives may be used as homobifunctional crosslinkers.

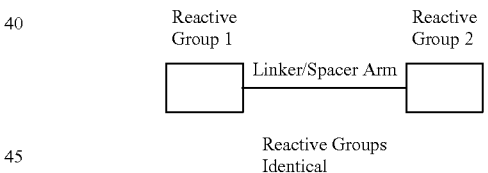

In some embodiments, heterobifunctional crosslinkers mediate bioconjugation. Heterobifunctional reagents can be used to crosslink proteins, nucleic acids, solid supports and other molecules or materials, for example, in a two- or three-step process. In some embodiments, one protein is modified with a heterobifunctional compound using the crosslinker's most reactive or most labile end. The modified protein may then be purified from excess reagent by gel filtration or rapid dialysis. In some embodiments, heterobifunctionals contain at least one reactive group that displays extended stability in aqueous environments, therefore allowing purification of an activated intermediate before adding the second molecule to be conjugated. For instance, an N-hydroxysuccinimide (NHS ester-maleimide hetero-bi-functional can be used to react with the amine groups of one protein through its NHS ester end (the most labile functionality), while preserving the activity of its maleimide functionality. Since the maleimide group has greater stability in aqueous solution than the NHS ester group, a maleimide-activated intermediate may be created. After a purification step, the maleimide end of the crosslinker can then be used to conjugate to a sulfhydryl-containing molecule. Heterobifunctional crosslinking reagents may also be used to site-direct a conjugation reaction toward particular parts of target molecules. In some embodiments, amines may be coupled on one molecule while sulfhydryls or carbohydrates are targeted on another molecule. In some embodiments, heterobifunctional reagents containing one photo-reactive end may be used to insert nonselectively into target molecules by UV irradiation. Another component of heterobifunctional reagents is the cross-bridge or spacer that ties the two reactive ends together. Crosslinkers may be selected based not only on their reactivities, but also on the length and type of cross-bridge they possess. Some heterobifunctional families differ solely in the length of their spacer. The nature of the cross-bridge may also govern the overall hydrophilicity of the reagent. For instance, polyethylene glycol (PEG)-based cross-bridges create hydrophilic reagents that provide water solubility to the entire heterobifunctional compound. In some embodiments, a number of heterobifunctionals contain cleavable groups within their cross-bridges, lending greater flexibility to the experimental design. A few crosslinkers contain peculiar cross-bridge constituents that actually affect the reactivity of their functional groups. For instance, a maleimide group that has an aromatic ring immediately next to it is less stable to ring opening and loss of activity than a maleimide that has an aliphatic ring adjacent to it. In addition, conjugates destined for use in vivo may have different properties depending on the type of spacer on the associated crosslinker. Some spacers may be immunogenic and cause specific antibody production to occur against them. In other instances, the half-life of a conjugate in vivo may be altered by the choice of cross-bridge, especially when using cleavable reagents. In some embodiments, the heterobifunctional crosslinker may be N-succinimidyl 3-(2-pyridyldithio)propionate (SPDP), standard SPDP, LC-SPDP, sulfo-LC-SPDP, succinimidyloxycarbonyl-α-methyl-α-(2-pyri-dyldithio) toluene, succinimidyl-4-(N-maleimidomethyl)cyclo-hexane-1-carboxylate, sulfosuccinimidyl-4-(N-maleimidomethyl) cyclohexane-1-carboxylate, m-maleimidobenzoyl-N-hydroxysuccinimide ester, m-maleimidobenzoyl-N-hydroxysulfo-succinimide ester, N-succinimidyl(4-iodoacetyl)aminobenzoate, sulfosuccinimidyl(4-iodoacetyl)amino-benzoate, succinimidyl-4-(p-maleimidophenyl)butyrate, N-(γ-maleimidobutyryloxy)succinimide ester, succinimidyl-3-(bromoacetamide) propionate, succinimidyl iodoacetate, 4-(4-N-maleimidophenyl)butyric acid hydrazide, 4-(N-maleimidomethyl)cyclohexane-1-carboxyl-hydrazide, 3-(2-pyridyldithio)propionyl hydrazide, N-hydroxysuccinimidyl-4-azidosalicylic acid, sulfosuccinimidyl-2-(p-azidosalicylamido) ethyl-1,3'-dithiopropionate, N-hydroxysulfosuccinimidyl-4-azido-benzoate, N-succinimidyl-6-(4'-azido-2'-nitrophenylamino)hexanoate, sulfosuccinimidyl-6-(4'-azido-2'-nitrophenylamino)hexanoate, N-5-Azido-2-nitrobenzoyloxysuccinimide, Sulfosuccinimidyl-2-(m-azido-o-nitrobenzamido)-ethyl-1,3'-dithiopropionate, N-succinimidyl-(4-azidophenyl)1,3'-dithiopropionate, sulfosuccinimidyl 4-(p-azidophenyl) butyrate, Sulfosuccinimidyl 2-(7-azido-4-methylcoumarin-3-acetamide)ethyl-1,3'-dithiopropionate, sulfosuccinimidyl 7-azido-4-methylcoumain-3-acetate, p-Nitrophenyl diazopyruvate, p-nitrophenyl-2-diazo-3,3,3-trifluoropropionate, 1-(p-azidosalicylamido)-4-(iodoacidamido)butane, N-[4-(p-azidosalicylamido)butyl]-3'-(2'-pyridyldithio) propionamide, Benzophenone-4-maleimide, p-azidobenzoyl hydrazide, 4-(p-azidosalicylamido)butylamine, or p-azidophenyl glyoxal.

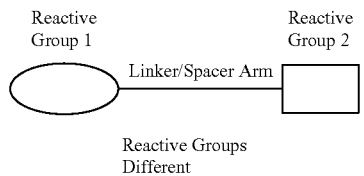

Reactive Groups Different

Other examples of crosslinkers, but not limited to, may be NHS-PEG$_4$-Azide, NHS-phosphine, N-γ-maleimidobutyryl-oxysulfosuccinimide ester, m-maleimidobenzoyl-N-hydroxysuccinimide ester, sulfosuccinimidyl (4-iodoacetyl)aminobenzoate, succinimidyl 3-(2-pyridyldithio)propionate), sulfosuccinimidyl (4-iodoacetyl)aminobenzoate, m-maleimidobenzoyl-N-hydroxysuccinimide ester, 1-Ethyl-3-[3-dimethylaminopropyl]carbodiimide hydrochloride, dimethyl pimelimidate, sulfosuccinimidyl 6-(3'-(2-pyridyldithio)propionamido)hexanoate, 6-(3'-[2-pyridyldithio]-propionamido)hexanoate, tris-(succinimidyl)aminotriacetate, Sulfo-NHS-LC-Diazirine, bismaleimidohexane, 1,4-bismaleimidobutane, sulfosuccinimidyl 4-(N-maleimidophenyl)butyrate, Sulfo-SBED Biotin Label Transfer Reagent, succinimidyl 6-(3(2-pyridyldithio)propionamido)hexanoate, succinimidyl 3-(2-pyridyldithio)propionate, sulfosuccinimidyl 6-(3'-(2-pyridyldithio)propionamido)hexanoate, L-Photo-Leucine, L-Photo-Methionine, sulfosuccinimidyl 4-(N-maleimidomethyl)cyclohexane-1-carboxylate, Pierce BS(PEG)5, sulfosuccinimidyl 2-((4,4'-azipentanamido)ethyl)-1,3'-dithiopropionate, Sulfo-NHS—SS-Diazirine, Pierce SM(PEG)n, NHS-dPEG-Mal, N-hydroxysulfosuccinimide, sulfosuccinimidyl 4-(N-maleimidomethyl)cyclohexane-1-carboxylate, Sulfosuccinimidyl-4-(N-maleimidomethyl)cyclohexane-1-carboxylate, 1-Ethyl-3-(3-Dimethylaminopropyl)carbodiimide Hydrochloride, N-α-maleimidoacet-oxysuccinimide ester, Sulfo-NHS-LC-Biotin, bis(sulfosuccinimidyl)suberate, trans-4-(maleimidylmethyl)cyclohexane-1-Carboxylate, bismaleimidohexane, 1,8-bismaleimido-diethyleneglycol, N-β-maleimidopropionic acid hydrazide, N-succinimidyl 3-(2-pyridyldithio)-propionate, sulfosuccinimidyl 4-(N-maleimidomethyl)cyclohexane-1-carboxylate, 3-(2-pyridyldithio)propionyl hydrazide, 4-(4-N-maleimidophenyl)butyric acid hydrazide, 3,3'-dithiobis(sulfosuccinimidyl propionate, bis(sulfosuccinimidyl) 2,2,4,4-glutarate-d4, or Succinimidyl-4-(N-maleimidomethyl)cyclohexane-1-carboxylate.

In some embodiments, the alkyne derivative attached to the solid support or SNAP may be, for example, dibenzocyclooctyne-amine, dibenzocyclooctyne-acid, dibenzocyclooctyne-N-hydroxysuccinimidyl ester, dibenzocyclooctyne-N-hydroxysuccinimidyl ester, dibenzocyclooctyne-sulfo-N-hydroxysuccinimidyl ester, ibenzocyclooctyne-sulfo-N-hydroxysuccinimidyl ester, Dibenzocyclooctyne-S—S—N-hydroxysuccinimidyl ester, dibenzocyclooctyne-PEG4-N-hydroxysuccinimidyl ester, dibenzocyclooctyne-PEG4-acid, dibenzocyclooctyne-maleimide, sulfo-dibenzocyclooctyne-biotin conjugate, (1R,8S,9s)-Bicyclo[6.1.0]non-4-yn-9-ylmethyl N-succinimidyl carbonate, (1R,8S,9s)-Bicyclo6.1.0non-4-yn-9-ylmethanol, APN-BCN, (1R,8S,9s)-Bicyclo6.1.0non-4-yn-9-ylmethanol, ethyl (1R,8S,9s)-bicyclo6.1.0non-4-ene-9-carboxylate, Alkyne-PEG5-acid, (R)-3-Amino-5-hexynoic acid hydrochloride, (S)-3-Amino-5-hexynoic acid hydrochloride, (R)-3-(Boc-amino)-5-hexynoic acid, (S)-3-(Boc-amino)-5-hexynoic acid, N-Boc-4-pentyne-1-amine, 4-pentyne-1-amine, Boc-propargyl-Gly-OH, 3-Ethynylaniline, 4-Ethynylaniline, PC biotin-alkyne, Propargyl chloroformate, Propargyl-N-hydroxysuccinimidyl ester, N—Z-4-pentyne-1-amine, 1-Azido-2-(2-(2-ethoxyethoxy)ethoxy)ethane, 0-(2-Azidoethyl)heptaethylene glycol, Click-iT® DIBO-Alexa Fluor® 488, Click-iT® DIBO-Alexa Fluor® 555, Click-iT® DIBO-Alexa Fluor® 594, Click-iT® DIBO-Alexa Fluor® 647, Click-iT® DIBO TAMRA, Click-iT® DIBO-biotin, Click-iT® DIBO-amine, Click-iT® DIBO-maleimide, Click-iT® DIBO-succinimidyl ester, Alexa Fluor® 488 alkyne, Alexa Fluor® 555 alkyne, triethylammonium salt, Alexa Fluor® 594 carboxamido-(5-(and 6-)propargyl), bis(triethylammonium salt, 3-propargyloxypropanoic acid, succinimidyl ester, biotin alkyne, tetraacetyl fucose alkyne, Oregon Green® 488 alkyne*6-isomer*, iodoacetamide alkyne, or 5-carboxytetramethylrhodamine propargylamide.

In some embodiments, the azide derivative attached to a solid support, SNAP, or biomolecule may be, for example, (S)-5-Azido-2-(Fmoc-amino)pentanoic acid, (S)-(–)-2-Azido-6-(Boc-amino)hexanoic acid (dicyclohexylammonium), (S)-2-Azido-3-(4-tert-butoxyphenyl)propionic acid cyclohexylammonium salt, L-Azidohomoalanine hydrochloride, (S)-2 Azido-3-(3-indolyl)propionic acid cyclohexylammonium salt, (S)-2-Azido-3-methylbutyric acid cyclohexylammonium salt, (S)-2-Azido-3-phenylpropionic acid (dicyclohexylammonium) salt, Boc-3-azido-Ala-OH (dicyclohexylammonium) salt, N-Boc-4-azido-L-homoalanine (dicyclohexylammonium) salt, N-Boc-6-azido-L-norleucine (dicyclohexylammonium) salt, Boc-4-azido-Phe-OH, (S)-(–)-4-tert-Butyl hydrogen 2-azidosuccinate (dicyclohexylammonium) salt, N2-[(1,1-Dimethylethoxy)carbonyl]-N6-[(2-propynyloxy)carbonyl]-L-lysine, Fmoc-β-azido-Ala-OH, 2-Acetamido-2-deoxy-β-D-glucopyranosyl azide, 2-Acetamido-2-deoxy-β-D-glucopyranosyl azide 3,4,6-triacetate, 2-Acetamido-3,4,6-tri-O-benzyl-2-deoxy-β-D-glucopyranosyl azide, N-Azidoacetylgalactosamine-tetraacylated, N-Azidoacetylglucosamine, N-Azidoacetylglucosamine-tetraacylated, 6-Azido-6-deoxy-1,2:3,4-di-O-isopropylidene-α-D-galactopyranose, 1-Azido-1-deoxy-β-D-galactopyranoside, 1-Azido-1-deoxy-β-D-galactopyranoside tetraacetate, 6-Azido-6-deoxy-D-galactose, 1-Azido-1-deoxy-β-D-glucopyranoside, 2-Azido-2-deoxy-D-glucose, 6-Azido-6-deoxy-D-glucose, 1-Azido-1-deoxy-β-D-lactopyranoside, 3-Azido-2,3-dideoxy-1-O-(tert-butyldimethylsilyl)-3-D-arabino-hexopyranose, 2-Azido-D-galactose tetraacetate, 1,2-Di-O-acetyl-3-azido-3-deoxy-5-β-(p-toluoyl)-D-ribofuranose, α-D-Mannopyranosyl azide tetraacetate, 2,3,4,6-Tetra-O-acetyl-1-azido-1-deoxy-α-D-galactopyranosyl cyanide, 2,3,4-Tri-O-acetyl-β-D-xylopyranosyl azide, 3'-Azido-3'-deoxythymidine, γ-(2-Azidoethyl)-ATP sodium salt solution, γ-[(6-Azidohexyl)-imido]-ATP sodium salt, (2'S)-2'-Deoxy-2'-fluoro-5-ethynyluridine, 5-Ethynyl-2'-deoxycytidine, N6-Propargyl-ATP sodium salt, 4-Acetamidobenzenesulfonyl azide, (E)-N-(2-Aminoethyl)-4-{2-[4-(3-azidopropoxy)phenyl]diazenyl}benzamide hydrochloride, Azidoacetic acid NHS ester, 1-Azidoadamantane, 4-Azidoaniline hydrochloride, (4S)-4-[(1R)-2-Azido-1-(benzyloxy)ethyl]-2,2-dimethyl-1,3-dioxolane, NHS-PEG$_4$-azide, [3aS-(3aα,4α,5β,7aα)]-5-Azido-7-bromo-3a,4,5,7α-tetrahydro-2,2-dimethyl-1,3-benzodioxol-4-ol, 3'-Azido-3'-2-azido-1-methylquinolinium tetrafluoroborate, 5-Azidopentanoic acid, 4-Azidophenacyl bromide, 4-Azidophenyl isothiocyanate, 3-(4-Azidophenyl) propionic acid, 3-Azido-1-propanamine, 3-Azido-1-propanol, Azo biotin-azide, Biotin picolyl azide, tert-Butyl 2-(4-{[4-(3-azidopropoxy)phenyl]azo}benzamido) ethylcarbamate, 4-Carboxybenzenesulfonazide, 7-(Diethylamino)coumarin-3-carbonyl azide, Ethidium bromide monoazide, Ethyl azidoacetate, 4-Methoxybenzyloxycarbonyl azide, aryl azides, diazierines, or O-(2-Aminoethyl)-O'-(2-azidoethyl)heptaethylene glycol, bromoacetomido-PEG$_3$-azide, iodoacetamide-azide, Alexa Fluor® 488 azide, Alexa Fluor® 488 5-carboxamido-(6-azidohexanyl), bis(triethylammonium salt), Alexa Fluor® 555 azide triethylammonium salt, Alexa Fluor® 594 carboxamido-(6-azidohexanyl), bis(triethylammonium salt), Alexa Fluor® 647 azide triethylammonium salt, 3-(azido-tetra(ethyleneoxy))propionic acid succinimidyl ester, biotin azide, L-azidohomoalanine, L-homopropargylglycine, Click-iT® farnesyl alcohol azide, 15-azidopentadecanoic acid, 12-azidododecanoic acid, tetraacetylated N-azidoacetylgalactosamine, tetraacetylated N-azidoacetyl-D-mannosamine, tetraacetylated N-azidoacetylglucosamine, iodoacetamide azide, or tetramethylrhodamine 5-carboxamido-(6-azidohexanyl).

In some embodiments, SNAPs may be covalently attached to a solid support using an inherent chemistry of the SNAP. In some embodiments, the solid support may be covered with functional groups that may be reactive to the SNAP. These functional groups, for example, may be hydroxyl, carbonyl, carboxyl, amino, amides, azides, alkynes, alkenes, phosphates, sulfhydryl, thiols, isothiocyanates, isocyanates, acyl azides, NHS esters, silane, sulfonyl chlorides, aldehydes, esters, glyoxals, epoxides, oxiranes, alkanethiols, carbonates, aryl halides, imidoesters, carbodiimides, anhydrides, fluorophenyl esters, amines, thymines or a combination thereof. In some embodiments, the SNAP may have a functional group that may react with a functional group on the solid support to form a covalent bond. For example, a DNA SNAP may be attached to a solid support by reacting one or more thymines in the DNA with amines on the solid support. For example, the —NH$_2$ at the N-terminus of a polypeptide chain or —COOH at the C-terminus of a polypeptide chain may react with an appropriate functional group and be attached to the solid support through a covalent bond. In some embodiments, for example, the functional group of a SNAP may be hydroxyl, carbonyl, carboxyl, amino, amides, azides, alkynes, silane, alkenes, phosphates, sulfhydryl, thiols, isothiocyanates, isocyanates, acyl azides, NHS esters, sulfonyl chlorides, aldehydes, esters, glyoxals, epoxides, oxiranes, alkanethiols, carbonates, aryl halides, imidoesters, carbodiimides, anhydrides, fluorophenyl esters, amines, thymines or a combination thereof. Other bioconjugation processes, reactions, and functional groups are described elsewhere within that may be used to attach a SNAP to a solid support. Such a reaction may be spontaneous, or may be induced by application of heat or ultraviolet radiation.

In some embodiments, silane chemistry may be employed for bioconjugation. In some embodiments, functional silane compounds containing an organofunctional or organo-reactive arm can be used to conjugate biomolecules to inorganic substrates. The appropriate selection of the functional or reactive group for a particular application can allow the attachment of proteins, oligonucleotides, whole cells, organelles, or even tissue sections to substrates. The organosilanes used for these applications may include functional or reactive groups such as hydroxyl, amino, aldehyde, epoxy, carboxylate, thiol, and even alkyl groups to bind molecules through hydrophobic interactions. In some embodiments, 3-Aminopropyltriethoxysilane (APTES) and 3-Aminopropyltrimethoxysilane are used to create a functional group on an inorganic surface or particle. In some embodiments, once deposited on a substrate, the alkoxy groups form a covalent polymer coating with the primary amine groups sticking off the surface and available for subsequent conjugation. Carboxyl- or aldehyde-containing ligands may be directly coupled to the aminopropyl groups using a carbodiimide reaction or reductive amination. In some embodiments, alternatively, surfaces initially derivatized with an aminopropylsilane compound can be modified further with spacer arms or crosslinkers to create reactive groups for coupling affinity ligands or biomolecules. For instance, the amine groups may be derivatized with an NHS-PEGn-azide compound for use in click chemistry or Staudinger ligation reactions for linking proteins or other biomolecules. In some embodiments, APTES-modified surfaces may be further derivatized with amine-reactive crosslinkers to create additional surface characteristics and reactivity. Modification with NHS-PEG4-azide forms a hydrophilic PEG spacer terminating in an azido group that can be used in a click chemistry or Staudinger ligation reaction to couple other molecules.

In some embodiments, other crosslinking agents that contain an amine-reactive group on one end also may be used to modify and activate the APTES-modified substrate. Surfaces may be designed to contain, for instance, reactive hydrazine or aminooxy groups for conjugation with carbonyl-containing molecules, such as aldehydes formed through periodate oxidation of carbohydrates or natively present at the reducing end of sugars and glycans. In other instances, crosslinking reagents may contain an amine-reactive group on one end to attach to the APTES-modified substrate and the other end can be a moiety that can intercalate DNA bases (for example, NHS esters of psoralen or other intercalating agents). Once SNAPs are immobilized by the intercalating interaction, they can be covalently crosslinked by thymidine adducts by exposure to UV light.

In some embodiments, the amine groups on ATPS surfaces may be acylated using glutaric anhydride to create carboxylate functionalities, which were then activated with NHS/DCC to form the NHS ester. This derivative may be used to couple amine-containing proteins and other molecules via amide bond formation. In a second activation strategy, the aminopropyl groups on the surface were activated with 1,4-phenylenediisothiocyanate (PDITC) to create terminal isothiocyanate groups for coupling amines. Both methods resulted in the successful coupling of amine-dendrimers to silica surfaces for use in arrays. In some embodiments, amine surfaces prepared using an aminosilane compound can be modified to contain carboxylate groups using the following protocol involving the reaction with an anhydride, such as succinic anhydride or glutaric anhydride. After modification, the carboxylates then can be used to couple amine-containing molecules using a carbodiimide reaction with EDC plus sulfo-NHS. In some embodiments, modification of an APTES surface with glutaric anhydride creates terminal carboxylates for coupling of amine-containing ligands which may be used for bioconjugation.

In some embodiments, aminosilane surfaces also may be activated by use of a bifunctional crosslinker to contain reactive groups for subsequent coupling to biomolecules. In one such reaction, N,N'-disuccinimidyl carbonate (DSC) was used to react with the amines on a slide surface and create terminal NHS-carbonate groups, which then may be coupled to amine-containing molecules, which may be used for bioconjugation. In some embodiments, APTES-modified surfaces can be activated with DSC to form amine-reactive succinimidyl carbonates for coupling proteins or other amine-containing molecules.

In some embodiments, silane coupling agents containing carboxylate groups may be used to functionalize a surface with carboxylic acids for subsequent conjugation with amine-containing molecules. For example, carboxyethylsilanetriol contains an acetate organo group on a silanetriol inorganic reactive end. The silanetriol component is reactive immediately with inorganic —OH substrates without prior hydrolysis of alkoxy groups, as in the case with most other silanization reagents. In some embodiments, carboxyethylsilanetriol has been used to add carboxylate groups to fluorescent silica nanoparticles to couple antibodies for multiplexed bacteria monitoring. This reagent can be used in similar fashion to add carboxylate functionality to many inorganic or metallic nano-materials, which also may create negative charge repulsion to maintain particle dispersion in aqueous solutions. In some embodiments, covalent coupling to the carboxylated surface then can be done by activation of the carboxylic acid groups with a carbodiimide to facilitate direct reaction with amine-containing molecules or to form intermediate NHS esters, which may be used for bioconjugation. In some embodiments, carboxylethylsilanetriol can be used to modify an inorganic substrate to containing carboxylate groups for coupling amine-containing ligands.

In some embodiments, silane modification agents such as glycidoxy compounds may be utilized for bioconjugation to a surface substrate. Glycidoxy compounds contain reactive epoxy groups. Surfaces covalently coated with these silane coupling agents can be used to conjugate thiol-, amine-, or hydroxyl-containing ligands, depending on the pH of the reaction. In some embodiments, 3-glycidoxy-propyltrimethoxysilane (GOPTS) or 3-glycidoxypro-pyltriethoxysilane can be used to link inorganic silica or other metallic surfaces containing —OH groups with biological molecules containing any three of these major functional groups. In some embodiments, epoxy-containing silane coupling agents form reactive surfaces that can be used to couple amine-, thiol-, or hydroxyl-containing ligands which may be used for bioconjugation.

In some embodiments, the reaction of the epoxide with a thiol group yields a thioether linkage, whereas reaction with a hydroxyl gives an ether and reaction with an amine results in a secondary amine bond. The relative reactivity of an epoxy group is thiol>amine>hydroxyl, and this is reflected by the optimal pH range for each reaction. In this case, the lower the reactivity of the functional group the higher the pH required to drive the reaction efficiently.

In some embodiments, isocyanates groups may be utilized for bioconjugation to a surface support. Isocyanate groups are extremely reactive toward nucleophiles and may hydrolyze rapidly in aqueous solution which are especially useful for covalent coupling to hydroxyl groups under nonaqueous conditions, which is appropriate for conjugation to many carbohydrate ligands. Silanization can be accomplished in dry organic solvent to form reactive surfaces while preserving the activity of the isocyanates. Isocyanatopropyltriethoxysilane (ICPTES) contains an isocyanate group at the end of a short propyl spacer, which is connected to the triethoxysilane group useful for attachment to inorganic substrates. In some embodiments, the isocyanate-containing silane coupling agent can be used to couple hydroxyl-containing molecules to inorganic surfaces which may be used for bioconjugation.

In some embodiments, ICPTES may be used to create novel chitosan-siloxane hybrid polymers by coupling the isocyanate groups to the functional groups of the carbohydrate and forming a silica polymer using the triethoxysilane backbone. In some embodiments, ICPTES and APTES have been used in combination to create organically modified silica xerogels through carboxylic acid solvolysis that formed hybrid materials with luminescent properties.

In some embodiments, nanoparticles or microparticles may be utilized as a solid support for bioconjugation. In some embodiments, particle types and compositions of almost limitless shape and size, including spherical, amorphous, or aggregate particles, as well as elaborate geometric shapes like rods, tubes, cubes, triangles, and cones. In addition, new symmetrical organic constructs have emerged in the nanometer range that include fullerenes (e.g., Buckyballs), carbon nanotubes, and dendrimers, which are highly defined synthetic structures used as bioconjugation scaffolds. The chemical composition of particles may be just as varied as their shape. Particles can comprise of polymers or copolymers, inorganic constructs, metals, semiconductors, superparamagnetic composites, biodegradable constructs, synthetic dendrimers, and dendrons. Polymeric particles can be constructed from a number of different monomers or copolymer combinations. Some examples include polystyrene (traditional "latex" particles), poly(styrene/divinylbenzene) copolymers, poly(styrene/acrylate) copolymers, polymethylmethacrylate (PMMA), poly (hydroxyethyl methacrylate) (pHEMA), poly (vinyltoluene), poly(styrene/butadiene) copolymers, and poly(styrene/vinyltoluene) copolymers. In some embodiments, by mixing into the polymerization reaction combinations of functional monomers, one can create reactive or functional groups on the particle surface for subsequent coupling to affinity ligands. One example of this is a poly(styrene/acrylate) copolymer particle, which creates carboxylate groups within the polymer structure, the number of which is dependent on the ratio of monomers used in the polymerization process. In some embodiments, inorganic particles are used extensively in various bioapplications. For example, gold nanoparticles may be used for detection labels for immunohistochemical (IHC) staining and lateral flow diagnostic testing. In some embodiments, the use of particles in bioapplications like bioconjugation involves the attachment of affinity capture ligands to their surface, by either passive adsorption or covalent coupling. The coupling of an affinity ligand to such particles creates the ability to bind selectively biological targets in complex sample mixtures. The affinity particle complexes can thus be used to separate and isolate proteins or other biomolecules or to specifically detect the presence of these targets in cells, tissue sections, lysates, or other complex biological samples. In some embodiments, the reactions used for coupling affinity ligands to nanoparticles or microparticles are basically the same as those used for bioconjugation of molecules described herein.

In some embodiments, particle type used for bioapplications (e.g., bioconjugation) is the polymeric microsphere or nano-sphere, which comprises a spherical, nonporous, "hard" particle made up of long, entwined linear or cross-linked polymers. In some embodiments, creation of these particles involves an emulsion polymerization process that uses vinyl monomers, sometimes in the presence of divinyl crosslinking monomers. In some embodiments, larger microparticles may be built from successive polymerization steps through growth of much smaller nanoparticle seeds. In some embodiments, polymeric particles comprise of polystyrene or copolymers of styrene, like styrene/divinylbenzene, styrene/butadiene, sty-rene/acrylate, or styrene/vinyltoluene. Other examples of polymer supports include polymethylmethacrylate (PMMA), polyvinyltoluene, poly(hydroxyethyl meth-acrylate) (pHEMA), and the copolymer poly(ethylene glycol dimethacrylate 2-hydroxyethylmetacrylate) [poly(EGDMA/HEMA)].

In some embodiments, one method of attaching biomolecules to hydrophobic polymeric particles is the use of passive adsorption. In some embodiments, protein adsorption onto hydrophobic particles takes place through strong interactions of nonpolar or aromatic amino acid residues with the surface polymer chains on the particles with concomitant exclusion of water molecules. Since proteins usually contain hydrophobic core structures with predominately hydrophilic surfaces, their interaction with hydrophobic particles must involve significant conformational changes to create large-scale hydrophobic contacts.

In some embodiments, particle types contain functional groups that are built into the polymer backbone and displayed on their surface. The quantity of these groups can vary widely depending on the type and ratios of monomers used in the polymerization process or the degree of secondary surface modifications that have been performed. In some embodiments, functionalized particles can be used to couple covalently biomolecules through the appropriate reaction conditions.

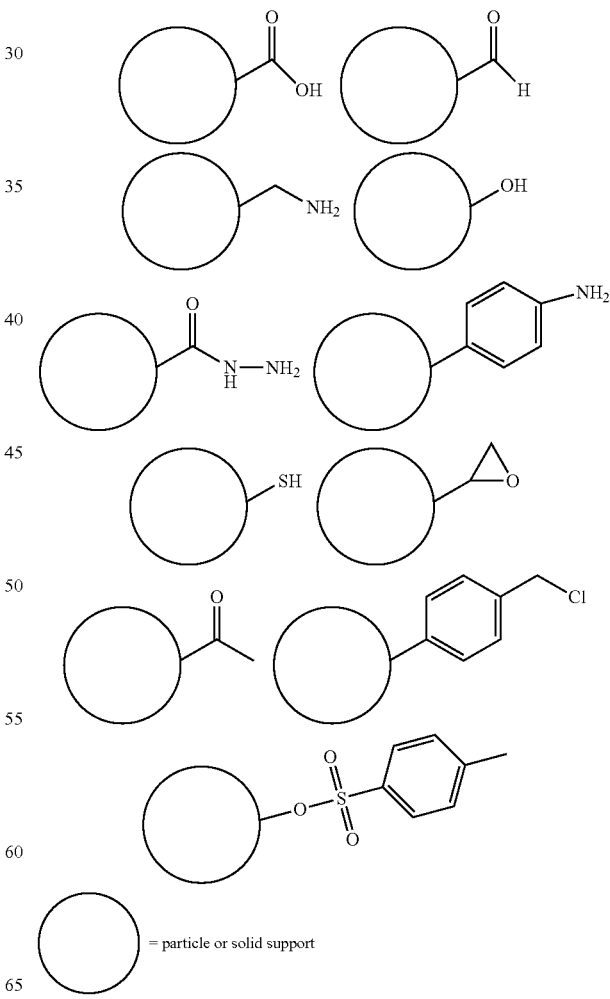

Common Functional Groups or Reactive Groups or Particles for Bioconjugation

In some embodiments, a particle may couple with a crosslinker for bioconjugation.

In some embodiments, the rate of attachment of SNAPs s to the solid support, or the efficacy or strength of attachment, may be altered by altering the sequence of a nucleic acid strand in the SNAP. For example, in the case of a SNAP attached to a solid support by a reaction involving one or more thymines the attachment may be varied by varying the number of thymines in the nucleic acid sequence. In some embodiments, increasing the number of thymines may facilitate the attachment of the SNAP to the solid support.

In some embodiments, the solid support is a part of a flow cell. In some embodiments, SNAPs may be attached to a solid support in a flow cell. In some embodiments, the SNAPs may be directly attached (e.g., conjugated or bound) to a solid support in a flow cell. In some embodiments, the SNAPs may be adsorbed to a solid support in a flow cell. Attaching the SNAPs in the flow cell may allow visualization of the SNAPs as they attach to the solid support. The attachment of the SNAPs may be optimized by monitoring the number of attached SNAPs compared to the number of attachment sites during the attachment process. For example, the number or location of occupied sites can be detected, and/or the number or location of vacant sites can be detected. This detection can be carried out to monitor SNAP loading during the attachment process and/or after loading has occurred. In some embodiments, the attachment of the SNAPs may be optimized by monitoring the area of the solid support covered by the SNAPs and the area of the solid support that is unoccupied by the SNAPs during the attachment process.

In some embodiments, SNAPs may be attached (e.g., conjugated or bound) directly in a flow cell. In some embodiments, the SNAPs may be attached to a surface within the flow cell. In some embodiments, the SNAPs may be attached to a surface within the flow cell before being attached to biological, chemical, or physical entities. In some embodiments, a biological, chemical, or physical entity may be flowed into a flow cell and then attached to a SNAP that is already attached to the solid support. In some embodiments, a biological, chemical, or physical entity may be attached to a SNAP before the SNAP is introduced into a flow cell and attached to a solid support in a flow cell. In some embodiments, a biological, chemical, or physical entity and a SNAP may be introduced into a flow cell and attached to each other within the flow cell, before the SNAP is attached to a solid support within the flow cell.

In some embodiments, the biological, chemical, or physical entities may be attached to the SNAPs prior to attaching the SNAPs to a solid support. After performing such a reaction the products may be purified to separate out attached SNAP-biological/chemical entity moieties from unattached SNAPs and biological/chemical entities.

The use of SNAPs for attaching biological, chemical, or physical entities to a solid support is optional. For example, in some configurations a biological, chemical, or physical entity can be attached to a solid support absent any SNAPs or absent other nucleic acids. A biological, chemical, or physical entity can be crosslinked, bound or otherwise attached to a solid support (e.g., at a site in an array) using reagents and techniques set forth herein including, but not limited to reagents and techniques exemplified in the context of attaching a SNAP to a solid support.

The methods of this disclosure may be used to spatially separate biological, chemical, or physical entities. In some embodiments, methods of this disclosure may be used to spatially separate proteins, small molecules, DNAs, RNAs, glycoproteins, metabolites, carbohydrates, enzymes, or antibodies. In some embodiments, methods of this disclosure may be used to spatially separate complexes, such as protein complexes comprising two or more proteins, protein nucleic acid complexes, or other complexes. In some embodiments, the methods may be used to spatially separate cells, organelles, viral particles or viroids. In some embodiments, the methods may be used to separate bacterial cells, microbial cells, mammalian cells or other cells.

In some embodiments, this disclosure provides a composition comprising a nucleic acid SNAP attached to a protein, a nucleic acid SNAP attached to a small molecule, a nucleic acid SNAP attached to a protein complex, a nucleic acid SNAP attached to a protein nucleic acid SNAP, a nucleic acid SNAP attached to a carbohydrate, a nucleic acid SNAP attached to a viral particle or a nucleic acid SNAP attached to a cell.

In some embodiments, this disclosure provides a composition comprising a dendrimer attached to a protein, a dendrimer attached to a small molecule, a dendrimer attached to a protein complex, a dendrimer attached to a protein dendrimer, a dendrimer attached to a carbohydrate, a dendrimer attached to a viral particle or a dendrimer attached to a cell.

In some embodiments, the biological, chemical, or physical entities may be eluted from the solid support either by cleaving a photo-cleavable bond, or by chemically or enzymatically digesting the SNAP.

In some embodiments, the biological, chemical, or physical entities may attach to the solid support directly, while the SNAPs occlude other biological, chemical, or physical entities from attaching in the immediate vicinity. In some embodiments, the biological, chemical, or physical entities may attach directly to an attachment site, for example, within a microwell or nanowell. Optionally, the size of the SNAPs may be selected to prevent more than one SNAP from occupying the microwell, nanowell or other site. In such cases, the SNAP may be removed, either by cleaving a photo-cleavable bond, or by chemically or enzymatically digesting the SNAP. Optionally, a biological, chemical, or physical entity is retained at a site from which a SNAP has been removed.

In some embodiments, SNAPs of this disclosure may be used as nanoparticles. For example, SNAPs of this disclosure may be used as nanoparticles for detection or visualization. In some embodiments, a nucleic acid SNAP may be formed which incorporates modified nucleotides which comprise fluorescent moieties. Any fluorescently labeled nucleotide may be used in a SNAP of this disclosure. Examples of fluorescently labeled nucleotides include, but are not limited to, Alexa Fluor™ 555-aha-dCTP, Alexa Fluor™ 555-aha-dUTP, 1 mM in TE buffer, Alexa Fluor™ 647 ATP (Adenosine 5'-Triphosphate, Alexa Fluor™ 647 2'-(or -3')-O—(N-(2-Aminoethyl) Urethane), Hexa(Triethylammonium) Salt), Alexa Fluor™ 647-aha-dCTP, Alexa Fluor™ 647-aha-dUTP, 1 mM in TE buffer, BODIPY™ FL ATP (Adenosine 5'-Triphosphate, BODIPY™ FL 2'-(or -3')-O—(N-(2-Aminoethyl)Urethane), Trisodium Salt), 5 mM in buffer, BODIPY™ FL ATP-7-S, Thioester (Adenosine 5'-O-(3-Thiotriphosphate), BODIPY™ FL Thioester, Sodium Salt), BODIPY™ FL GDP (Guanosine 5'-Diphosphate, BODIPY™ FL 2'-(or -3')-O—(N-(2-Aminoethyl) Urethane), Bis (Triethylammonium) Salt), ChromaTide™ Alexa Fluor™ 488-5-UTP, ChromaTide™ Alexa Fluor™ 488-5-dUTP, ChromaTide™ Alexa Fluor™ 546-14-UTP, Chroma- Tide™ Alexa Fluor™ 546-14-dUTP, ChromaTide™ Alexa Fluor™ 568-5-dUTP, ChromaTide™ Alexa Fluor™ 594-5-dUTP, ChromaTide™ Fluorescein-12-dUTP, ChromaTide™ Texas Red™-12-dUTP, Fluorescein-12-dUTP Solution (1 mM), Fluorescein-aha-dUTP—1 mM in TE Buffer, Guanosine 5'-O-(3-Thiotriphosphate), BODIPY™ FL Thioester, Sodium Salt (BODIPY™ FL GTP-γ-S, Thioester), Guanosine 5'-Triphosphate, BODIPY™ FL 2'-(or -3')-O—(N-(2-Aminoethyl) Urethane), Trisodium Salt (BODIPY™ FL GTP), Guanosine 5'-Triphosphate, BODIPY™ TR 2'-(or -3')-O—(N-(2-Aminoethyl) Urethane), Trisodium Salt (BODIPY™ TR GTP), MANT-ADP (2'-(or -3')-O—(N-Methylanthraniloyl) Adenosine 5'-Diphosphate, Disodium Salt), MANT-ATP (2'-(or -3')-O—(N-Methylanthraniloyl) Adenosine 5'-Triphosphate, Trisodium Salt), MANT-GDP (2'-(or -3')-O—(N-Methylanthraniloyl) Guanosine 5'-Diphosphate, Disodium Salt), MANT-GMPPNP (2'-(or -3')-O—(N-Methylanthraniloyl)-β:γ-Imidoguanosine 5'-Triphosphate, and Trisodium Salt), MANT-GTP (2'-(or -3')-O—(N-Methylanthraniloyl) Guanosine 5'-Triphosphate, Trisodium Salt).

In some embodiments, a SNAP of this disclosure may be designed such that affinity agents may be attached onto the surface of the SNAP. A SNAP with attached affinity agent may be used as a detection reagent. In some embodiments, a SNAP with attached affinity agents is also labeled with fluorescent moieties to form a fluorescent detection reagent. In some embodiments, a SNAP with attached affinity agents and fluorescent moieties may provide a high degree of signal amplification. The amount of affinity agents on the SNAP may be titrated to achieve a desired degree of binding or avidity. In some embodiments, differently sized SNAPs may be attached to different affinity agents. In some embodiments, differently colored SNAPs may be attached to different affinity agents. In some embodiments, a library of different affinity agents may be attached to fluorescently labeled SNAPs such that a first affinity agent is attached to a SNAP which is a different size and/or color from a SNAP each other affinity agent is attached to.

A system of the present disclosure can optionally be configured for optical detection. For example, the system can be configured for luminescence detection. Analytes or other entities can be detected, and optionally distinguished from each other, based on measurable characteristics such as the wavelength of radiation that excites a luminophore, the wavelength of radiation emitted by a luminophore, the intensity of radiation emitted by a luminophore (e.g., at particular detection wavelength(s)), luminescence lifetime (e.g., the time that a luminophore remains in an excited state) or luminescence polarity. The luminophore can be an intrinsic moiety of an analyte or other entity to be detected, or the luminophore can be an exogenous moiety that has been synthetically added to an analyte or other entity. Other optical characteristics that can be detected, and optionally used to distinguish analytes or other entities, include, for example, absorbance of radiation (e.g., at particular detection wavelength(s)), resonance Raman, radiation scattering or the like.

A system of the present disclosure can use a light sensing device that is appropriate for detecting a characteristic. Particularly useful components of a light sensing device can include, but are not limited to, optical sub-systems or components used in nucleic acid sequencing systems. Examples of useful sub systems and components thereof are set forth in US Pat. App. Pub. No. 2010/0111768 A1 or U.S. Pat. No. 7,329,860; 8,951,781 or 9,193,996, each of which is incorporated herein by reference. Other useful light sensing devices and components thereof are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference. Light sensing devices and components that can be used to detect luminophores based on luminescence lifetime are described, for example, in U.S. Pat. Nos. 9,678,012; 9,921,157; 10,605,730; 10,712,274; 10,775,305; or 10,895,534 each of which is incorporated herein by reference.

In assays with luminescent (e.g., fluorescent) detection, one or more entities (often very large arrays of them) may be immobilized on a surface, and this surface may be scanned with a microscope to detect any luminescent (e.g., fluorescent) signal from the immobilized objects. The microscope itself may comprise a digital camera or other luminescence detector configured to record, store, and analyze the data collected during the scan. A luminescence detector of the present disclosure can be configured for epiluminescent detection, total internal reflection (TTR) detection, waveguide assisted excitation (e.g., zero mode waveguides) or the like. Particular configurations of the methods and apparatus set forth herein can detect optical properties other than luminescence. For example, bright field imaging, light scattering, light absorption, or resonance Raman can be useful.

A light sensing device may be based upon any suitable technology, and may be, for example, a charged coupled device (CCD) sensor that generates pixilated image data based upon photons impacting locations in the device. A variety of other light sensing devices may also be used including, but not limited to, a detector array configured for time delay integration (TDI) operation, a complementary metal oxide semiconductor (CMOS) detector, an avalanche photodiode (APD) detector, a Geiger-mode photon counter, a photomultiplier tube (PMT), charge injection device (CID) sensors, JOT image sensor (Quanta), or any other suitable detector. TDI mode detection can be coupled with line scanning, for example, as described in U.S. Pat. No. 7,329,860, which is incorporated herein by reference. Other useful imaging devices include those that are configured for single-pixel detection, for example, by aligning each pixel with a site or feature of a solid support that is to be detected and/or by using a masking pattern to prevent individual pixels from acquiring signals derived from outside a limited field of view. Super-resolution systems that transcend the theoretical diffraction limit for resolving objects observed at particular wavelengths can also be used.

A particularly useful imaging device can be configured for compressive sampling to achieve single pixel imaging. A feature of this configuration is a regular grid of mirrors in the imaging path which can direct light from certain grid locations away from a photodiode and others toward the photodiode. The photodiode then measures the combined signal from all grid locations which are "active" (directing light toward the diode). The signal can be measured with various combinations of active/inactive grid locations and then the image is reconstructed mathematically (e.g., by solving a linear system of equations with a sparsity constraint). The device can be configured to have a single photodiode acquiring signal from a plurality of mirrors. Compressive sampling can be carried out as set forth, for example, in Duarte et al. *IEEE Signal Processing Magazine*, March 2008 pp. 83-91, which is incorporated herein by reference.

A luminescence detector can include any of a variety of excitation sources including, but not limited to, lasers, light emitting diodes (LEDs), lamps or the like. An instrument of the present disclosure can have a single detection channel, for example, when analytes need not be distinguished based on differences in excitation wavelength, emission wavelength or other optical characteristic. Alternatively, an instrument can include a plurality of detection channels, each configured to distinguish one analyte from another based on excitation wavelength, emission wavelength or other optical characteristic that is differentiated by the detection channels. Accordingly, an instrument can include one or more luminescence detectors and one or more excitation sources. Optionally, some or all of the optical components can be separable from a flow cell or other vessel that is detected in a method set forth herein. In some configurations, the flow cell or other vessel need not include any optical components. In alternative configurations, one or more optical component, such as a lens or fiber optic, can be integrated with a flow cell or other vessel. Thus, the optical component that is proximal to the sample can be provided by the detection apparatus, or alternatively, by the vessel that houses the sample.

An optical detection system can further include an autofocus system. An autofocus system can include (a) a detector that is configured to distinguish a characteristic signal from a subject that is correlated with its distance from the objective of the detector, (b) a converter that is responsive to the characteristic distinguished by the detector, and (c) an actuator that is configured to alter the distance between the subject and objective based on an action or instruction from the converter. Exemplary characteristic signals that can be used for focusing an array substrate or other solid support include, but are not limited to, the size or shape of a site reflected or transmitted from a surface, the distance or relative orientation between two or more sites reflected or transmitted from a surface, or the location of a site on a surface. Autofocus can be deployed before, during or after acquiring analytical signals from an array or other solid support. In particular embodiments, analytical signals can be used in a focus method. For example, sites in an array can be imaged and the sites can be treated as regions of interest that are evaluated for size, sharpness or other characteristic that is correlated with degree of focus. In some configurations an autofocus system can send information to a processor that is indicative of the quality of focus at a particular time during a detection process. The resulting quality metric can be integrated into a pixel classifier or can be used in combination with an algorithm that performs image analysis using a pixel classifier. A focus quality metric that is obtained from an autofocus system is an optional input to a pixel classifier or to an image analysis method set forth herein. A focus quality metric can be derived from theoretical or empirical characterization of one or more components of an optical detection system and can be used independently or in combination with a quality metric derived from an autofocus system.

A detection apparatus that is used in a method or apparatus set forth herein need not be configured for optical detection. For example, the detector can be an electronic detector used for detection of protons or pyrophosphate (see, for example, US Pat. App. Pub. Nos. 2009/0026082 A1; 2009/0127589 A1; 2010/0137143 A1; or 2010/0282617 A1, each of which is incorporated herein by reference in its entirety, or the Ion Torrent™ systems commercially available from ThermoFisher, Waltham, Mass.). A field effect transistor (FET) can be used to detect analytes or other entities, for example, based on proximity of a field disrupting moiety to the FET. Exemplary sensors and methods for attaching molecules to sensors are set forth in US Pat. App. Pub. Nos. 2017/0240962 A1; 2018/0051316 A1; 2018/0112265 A1; 2018/0155773 A1 or 2018/0305727 A1; or U.S. Pat. Nos. 9,164,053; 9,829,456; 10,036,064, each of which is incorporated herein by reference.

In some embodiments, pixels of a light sensing device can be advantageously used to image one or more objects (e.g., sites of an array, analytes in an array or other entities in an array). In comparison, for example, due to resolution limits, a camera used in a microscope may be expected to use at least four pixels per object. In some embodiments, each pixel may have a detection area of, for example, at most about 100 $nm^2$, 500 $nm^2$, 1 $\mu m^2$, 1.5 $\mu m^2$, 2 $\mu m^2$, 3 $\mu m^2$, 4 $\mu m^2$, 5 $\mu m^2$, 8 $\mu m^2$, or 10 $\mu m^2$. The light sensing array may have a size of at least about 100 kilopixels, 200 kilopixels, 400 kilopixels, 600 kilopixels, 800 kilopixels, 1 megapixels, 2 megapixels, 3 megapixels, 4 megapixels, 6 megapixels, 8 megapixels, 10 megapixels, 50 megapixels, 100 megapixels, 500 megapixels, 1 gigapixel, or 10 gigapixels.

The dimensions of an individual pixel or group of pixels in a light sensing device may match the dimensions of a site that is to be detected on a solid support. For example, a pixel may have an area of 1.4 $\mu m \times 1.4$ $\mu m$ (e.g., www.onsemi.com/pub/Collateral/MT9F002-D.PDF, 14 megapixels, 6.6×4.6 $mm^2$). In comparison, the sites (e.g., landing sites) in an array may be about 0.3 $\mu m$ in diameter with a pitch of 1.625 $\mu m$. The density of sites in the array can be increased, for example, by reducing the pitch to 0.975 $\mu m$ or 0.650 $\mu m$. The size of the pixel may also be reduced. In principle, this design may be extended to much larger sensor arrays, including those set forth herein.

A light sensing device may acquire image or pixel information at an imaging rate of, for example, at least about 0.1, 0.5, 1, 2, 3, 4, 5, 10, 20, 30, 40, 50, 100, 200, 300, 400, 500, 1000, 2000, 2500, 5000, 7500, 10000, or 20000 frames per second (fps). A light sensing device may perform signal amplification, such as by using one or two amplifiers for each pixel. The signal amplification may be performed by components of the light sensing devices without using a separate amplification circuit, or by using a separate amplification circuit, or by a combination thereof. The array of light sensing devices may comprise for example, sCMOS sensors having one or two readout circuits per column of pixels.

In some configurations, one or more components of a detection apparatus can be integrated with a flow cell, chip or other vessel that contains analytes or other entities to be detected. Optionally, methods and systems of the present disclosure may comprise one or more device features selected from: (i) a surface coating (e.g., $ZrO_2$, silane, or thiols) to promote adhesion of specific biological, chemical, or physical entities; (ii) a surface coating (e.g., phosphate or phosphonate, PEG-silane, or PEG-thiols) to prevent non-specific binding of specific biological, chemical, or physical entities; (iii) a differential surface coating (e.g., a patterned surface coating) to promote binding of a first type of biological, chemical, or physical entities in some locations and to prevent non-specific binding in other locations; (iv) a single-layer surface coating; (v) a multiple-layer surface coating; (vi) a surface coating deposited by atomic layer deposition (ALD), molecular layer deposition (MLD), chemical layer deposition (CVD), physical layer deposition (PLD) (e.g., evaporation), spin coating, dipping, or a combination thereof; (vii) a surface coating patterned by lithography and/or etching processes; (viii) a surface coating with one or more optical properties (e.g., bandpass filters, polarization filters, anti-reflection, fluorescent, reflective coatings); (ix) a compartment of each pixel with nanowell-like structures to prevent cross-talk (nanowells with opaque walls) and/or increase fluorescent light collection (nanowells with photo-sensitive walls); and (x) a combination thereof. These and other surface coatings can occur on the surface of a flow cell that is separable from a detector, or on the surface of a flow cell that is integrated with a detector (e.g., a light sensing device).

In some embodiments, a coating used on sites of an array, or between them, comprises one or more dielectrics, one or more plastics, one or more types of glass, one or more nitrides, one or more metals (e.g., gold), one or more metal oxides (e.g., $ZrO_2$), and/or one or more metal nitrides (e.g., TiN) in layer thicknesses varying from a few angstroms to several nanometers. A total number of coating layers of at least 1, 2, 3, 4, 5, 6, 7, 8, 9, 10, 12, 14, 16, 18, 20, 30, 40, 50, or 100 coating layers may be used.

In some embodiments, a surface chemistry is used on the immobilization sites, or between them, which may include silanes (e.g., (3-Aminopropyl)triethoxysilane, APTES), phosphates or phosphonates (e.g., (Aminomethyl)phosphonic acid, free phosphate) and thiols (e.g., Thiol-PEG-Amine, mPEG-Thiol), in thicknesses ranging from a few angstroms to a few nanometers.

In some embodiments, one or more pixels of a light sensing device may be surrounded by a filter, shade or barrier (e.g., forming a light pipe from the pixels(s) to an array site) to prevent crosstalk between pixels and/or to increase light collection. To prevent crosstalk, a shade or barrier may comprise at least one layer that is opaque to light (e.g., in a wavelength range at which the biological, chemical, or physical entities to be detected are emitting); an example of such a layer is a metal (e.g., Al or Ti). The layer that is opaque to light may comprise, for example, a dye. Since bandpass filter transmission is a function of angle of incidence, at large angles of incidence, the bandpass filter may have low transmission at the dye's emission wavelengths, thereby reducing crosstalk between adjacent pixels. For example, a fluorescein or Alexa 488 emission filter may be used in a dry environment, a water environment, or an oil environment. Optionally, transmission measurements may be generated using Semrock's "MyLight" software.

The passing band for a filter may comprise a bandwidth of, for example, at most about 10 nm, 20 nm, 30 nm, 40 nm, 50 nm, 100 nm, or 150 nm. In some embodiments, the filters comprise multi-band filters. The passing band for the filter may comprise a band center value of, for example, about 200 nm, 220 nm, 240 nm, 260 nm, 280 nm, 300 nm, 320 nm, 340 nm, 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, 900 nm, 920 nm, 940 nm, 960 nm, 980 nm, or 1,000 nm.

The excitation light (e.g., electromagnetic radiation sufficient to excite the array of biological, chemical, or physical entities to produce an emission signal) may have an incidence angle of about 90 degrees, 80 degrees, 70 degrees, 60 degrees, 50 degrees, 40 degrees, 30 degrees, 20 degrees, or 10 degrees from a surface (e.g., sidewall) of the array of biological, chemical, or physical entities. To increase light collection, the region around a pixel (e.g., microwell or nanowell walls) may contain one or more layers of material to convert photons to electrons (e.g., a silicon p-n junction) and one or more layers of material to collect the generated electrons (e.g., a metal such as Al or Ti).

The present disclosure further provides assays for detecting one or more analytes. Exemplary assays are set forth below in the context of detecting proteins. Methods and systems set forth herein can be adapted for use with other analytes such as nucleic acids, polysaccharides, metabolites, vitamins, hormones, enzyme co-factors or other entities.

A protein can be detected using one or more affinity agents having known, or measurable, binding affinity for the protein. The affinity agent and the protein can be bound to form a complex and then the complex can be detected. The complex can be detected directly, for example, due to a label that is present on the affinity agent or protein. In some configurations the complex need not be directly detected, for example, in formats where the complex is formed and the affinity agent, protein, or a tag or label component that was present in the complex is then detected.

A protein can be detected using one or more reagents that produce a detectable signal when interacting with the protein. For example, the reagent can add a detectable moiety to the protein, such as a luminophore or other label. In another example, the reagent, upon interacting with the protein, can be modified to produce a detectable signal or to produce a product that is subsequently detected.

In some detection assays, a protein can be modified in a multicycle assay and modified products from each cycle can be detected. For example, each cycle can include steps of labeling and removing N-terminal amino acids of a protein in a step-wise manner, and detecting released N-terminal labels. An example of this configuration is an Edman-type sequencing reaction in which a phenyl isothiocyanate reacts with an N-terminal amino group under mildly alkaline conditions, for example, about pH 8, to form an isolable, relatively stable cyclical phenylthiocarbamoyl Edman complex derivative. The phenyl isothiocyante may be substituted or unsubstituted with one or more functional groups, linker groups, or linker groups containing functional groups. An Edman-type sequencing reaction can include variations to reagents and conditions that yield a detectable removal of amino acids from a protein terminus, thereby facilitating determination of the amino acid sequence for a protein or portion thereof. For example, the phenyl group may also be replaced with at least one aromatic, heteroaromatic or aliphatic group which may participate in an Edman-type sequencing reaction, non-limiting examples including: pyridine, pyrimidine, pyrazine, pyridazoline, fused aromatic groups such as naphthalene and quinoline), methyl or other alkyl groups or alkyl group derivatives (e.g., alkenyl, alkynyl, cyclo-alkyl). Under certain conditions, for example, acidic conditions of about pH 2, derivatized terminal amino acids may be cleaved, for example, as a thiazolinone derivative. The thiazolinone amino acid derivative under acidic conditions may form a more stable phenylthiohydantoin (PTH) or similar amino acid derivative which can be detected. This procedure can be repeated iteratively for residual protein to identify the subsequent N-terminal amino acids and so forth. Many variations of the Edman degradation have been described and may be used including, for example, a one-step removal of an N-terminal amino acid using alkaline conditions (Chang, J. Y., *FEBS LETTS.*, 1978, 91(1), 63-68), which is incorporated by reference herein in its entirety.

Affinity agents described herein may be used in combination with Edman-type sequencing reactions. For example, an array including a plurality of proteins may be characterized by analyzing signals from first and second affinity agents that bind to different protein sites on the array. Further characterization may be performed by employing one or more Edman-type sequencing cycles for proteins on the array including the proteins that bound to the affinity reagents. The Edman-type cycles can be performed to sequentially remove N-terminal residues from the proteins on the array. After a known number of Edman-type cycles, an epitope that was recognized by the first affinity agent may be removed from a first protein while an epitope that was recognized by the second affinity agent may be retained in a second protein. The array may be contacted again with the first and second affinity agents and the results compared to the binding step that was carried out prior to the Edman-type cycles. Loss of binding signal from the array site for the first protein may indicate that the epitope for the first affinity reagent was located near the N-terminus of the protein, and that the epitope was located within a length of amino acid sequence that correlates with the number of Edman-type cycles performed between the binding steps. Conversely, repeated observation of binding signal from the array site for the second protein may indicate that the epitope for the second affinity reagent is located at a location other than within a length of amino acid sequence that correlates with the number of Edman-type cycles performed between the binding steps.

Proteins can be detected based on their enzymatic or other biological activity. For example, a protein can be contacted with a reactant that is converted to a detectable product by an enzymatic activity of the protein. In other assay formats, a first protein having a known enzymatic function can be contacted with a second protein to determine if the second protein changes the enzymatic function of the first protein. As such, the first protein serves as a reporter molecule for detection of the second protein. Exemplary changes that can be observed include, but are not limited to, activation of the enzymatic function, inhibition of the enzymatic function, degradation of the first protein or competition for a reactant or cofactor used by the first protein.

Proteins can be detected based on their binding interactions with other molecules such as proteins (e.g., with or without post translational modifications), nucleic acids, nucleotides, metabolites, small molecules that participate in biological signal transduction pathways, biological receptors or the like. For example, a protein that participates in a signal transduction pathway can be identified by detecting binding of the protein with a second protein that is known to be its binding partner in the pathway. Optionally, a target protein can be attached to a SNAP and then contacted with an affinity agent, that is known to have affinity for the protein. The target protein can be identified based on observed binding by the affinity agent molecule or lack of binding by the affinity agent molecule. The affinity agent molecule can optionally be labeled using labels.

In some configurations of the protein detection methods set forth herein, the proteins can be detected on a solid support. For example, proteins can be attached to a support, the support can be contacted with affinity agents in solution, the affinity agents can interact with the proteins, thereby producing a detectable signal, and then the signal can be detected to determine the presence of the proteins. In multiplexed versions of this approach, different proteins can be attached to different sites in an array, and the probing and detection steps can occur in parallel. In another example, affinity agents can be attached to a solid support, the support can be contacted with proteins in solution, the proteins can interact with the affinity agents, thereby producing a detectable signal, and then the signal can be detected to determine the presence of the proteins. This approach can also be multiplexed by attaching different affinity agents to different sites of an array. Proteins can be attached to a solid support via conjugation to (or binding to) SNAPs or via direct conjugation to (or binding to) the solid support. For example, a plurality of proteins can be conjugated (or bound) to a plurality of SNAPs, such that each protein-attached SNAP forms at a site in the array.

Suitable protein detection methods, such as enzyme linked immunosorbent assay (ELISA), can be used to detect one or more protein in a sample by exploiting high specificity binding of antibodies, aptamers or other binding agents to the protein(s) and detecting the binding event, which can ignore all other proteins in the sample. ELISA methods can be carried out by detecting immobilized binding agents and/or proteins in multiwell plates, detecting immobilized binding agents and/or proteins on arrays, or detecting immobilized binding agents and/or proteins on particles in microfluidic devices. Exemplary plate-based methods include, for example, the MULTI-ARRAY technology commercialized by MesoScale Diagnostics (Rockville, Maryland) or Simple Plex technology commercialized by Protein Simple (San Jose, CA). Exemplary, array-based methods include, but are not limited to those utilizing Simoa® Planar Array Technology or Simoa® Bead Technology, commercialized by Quanterix (Billerica, MA). Further exemplary array-based methods are set forth in U.S. Pat. Nos. 9,678,068; 9,395,359; 8,415,171; 8,236,574; or 8,222,047, each of which is incorporated herein by reference. Exemplary microfluidic detection methods include those commercialized by Luminex (Austin, Texas) under the trade name xMAP® technology or used on platforms identified as MAGPIX®, LUMINEX® 100/200 or FEXMAP 3D®. These assays can be readily modified for use with a system or method set forth herein.

Other detection methods that can be used herein, and that are particularly useful at low plex scale include procedures that employ SOMAmer reagents (e.g., aptamers) and SOMAscan assays commercialized by Soma Logic (Boulder, CO). In one configuration, a sample is contacted with aptamers that are capable of binding proteins due to specificity for the amino acid sequence of the proteins. The resulting aptamer-protein complexes can be separated from other sample components, for example, by attaching the complexes to beads, SNAPs or SNAP complexes that are removed from the sample. The aptamers can then be isolated and, because the aptamers are nucleic acids, the aptamers can be detected using any of a variety of methods for detecting nucleic acids, including for example, hybridization to nucleic acid arrays, PCR-based detection, or nucleic acid sequencing. Exemplary methods and compositions for use in an aptamer-based or other detection method set forth herein are set forth in U.S. Pat. No. 8,404,830; 8,975,388; 9,163,056; 9,938,314; 10,239,908; 10,316,321 or 10,221,207. Further examples are set forth in U.S. Pat. No. 7,855,054; 7,964,356; 8,975,026; 8,945,830; 9,404,919; 9,926,566; 10,221,421; 10,316,321 or 10,392,621. The above patents are incorporated herein by reference.

Proteins can also be detected based on proximity of two or more affinity agents. For example, two affinity agents can each include a receptor component and a nucleic acid component. When the affinity agents bind in proximity to each other, for example, due to ligands for the respective receptors being on a single protein, or due to the ligands being present on two proteins that associate with each other, the nucleic acids can interact to cause a modification that is indicative of the proximity. For example, one of the nucleic acids can be extended using the other nucleic acid as a template, one of the nucleic acids can form a template that positions the other nucleic acid for ligation to another nucleic acid, or the like. This type of assay can be multiplexed by utilizing a plurality of tag sequences in the nucleic acid components and identifying the tags in the modified nucleic acids. If the tags are originally assigned to known affinity agents or proteins, then the sequence of modified nucleotide components can be determined to identify which affinity agents and proteins bound to each other. Exemplary methods are commercialized by Olink Proteomics AB (Uppsala Sweden) or set forth in U.S. Pat. No. 7,306,904; 7,351,528; 8,013,134; 8,268,554 or 9,777,315, each of which is incorporated herein by reference.

A method of detecting a protein, can include steps of (i) contacting a first set of binding reagents with a protein, and (ii) detecting binding of the protein to a binding reagent in the first set of binding reagents. The method can optionally include one or more of the further steps of (iii) removing the first set of binding reagents, (iv) binding a second set of binding reagents to the protein, wherein binding reagents in the second set are different from binding reagents in the first set, and (v) detecting binding of the protein to a binding reagent in the second set of binding reagents. The method can optionally be carried out for a plurality of proteins located at sites in an array.

High specificity affinity agents can be useful in a number of protein detection methods. Alternatively, detection can be based on multiple low specificity detection cycles that are performed on a sample such that the individual cycles may detect multiple proteins while not necessarily distinguishing one of the detected proteins from another in any one of the cycles. However, using compositions and methods set forth herein, results from multiple cycles can be combined to achieve high-confidence quantification, identification or characterizations of a plurality of individual proteins in the sample. For example, different protein species can be resolvable, one from another, via attachment to uniquely identifiable sites in an array of sites. A series of affinity agents can be contacted with the array and each site can be examined with regard to whether or not it binds to one or more affinity agents in the series. As such, each site is encoded by a series of binding events and non-binding events. The affinity agents can be previously characterized with regard to the probability that a given affinity agent will bind to one or more epitopes suspected of being present in proteins on the array. Moreover, the characterization of the affinity agents can extend to the probability that a given affinity agent will bind to one or more proteins known to be, or suspected of being, present on the array. This can be the case, for example, when the arrayed proteins are derived from an organism for which the sequences of proteins in all or part of the proteome is known. Each site in the array can be decoded in view of (a) the series of binding events and/or non-binding events, (b) the identity of the affinity agent(s) used in each cycle and (c) the known binding characteristics of the affinity agents. Accordingly, even if the individual cycles yield ambiguous results with regard to distinguishing the identity of a subset of proteins that produce detectable signal, characterizing the signals across multiple cycles can allow individual proteins to be individually and unambiguously identified. The resulting set of identified proteins can be larger than the number of proteins that produce signal from any of the individual cycles. As set forth in further detail below, the use of promiscuous affinity agents can further increase the yield of proteins identified per affinity agent used. For example, as few as several hundred affinity reagents can provide unambiguous identification of thousands of proteins in the human proteome (or other proteome of comparable complexity). See U.S. Pat. No. 10,473,654, which is incorporated herein by reference. Decoding methods and algorithms are set forth in further detail below.

Affinity agents used in some configurations of the multi-cycle detection methods set forth herein, may have a broad range of binding affinity with respect to a population of proteins. For example, an affinity agent may be considered to be a 'promiscuous' affinity agent due to its affinity for a single epitope that is present in a plurality of different proteins in a sample, or due to its affinity for a plurality of different epitopes that are present in one or more proteins in the sample.

A promiscuous affinity agent may be characterized such that it has an identified, determined, or assessed probability-based binding profile. An affinity agent may be characterized as capable of binding to a first protein (or protein epitope) with a first apparent binding probability and capable of binding to a second protein (or protein epitope) with a second apparent binding probability. The first apparent binding probability can be the same as, greater than or less than the second apparent binding probability. The apparent probability for a given affinity reagent to bind with a particular protein (or protein epitope) can be, for example, at least about 0.001, 0.01, 0.1, 0.25, 0.5, 0.75, 0.9, 0.99, 0.999, or higher (on a scale of 0 to 1). Alternatively or additionally, the apparent probability for a given affinity reagent to bind with a particular protein (or protein epitope) can be, for example, at most about 0.999, 0.99, 0.9, 0.75, 0.5, 0.25, 0.1, 0.01, 0.001, or lower. Probabilistic affinity agent binding profiles may be determined or identified by in vitro measurements or in silico predictions.

Protein identification methods that are based on multiple detection cycles may further incorporate computational decoding approaches that are optimized for promiscuous affinity agents. A computation decoding algorithm can be trained to recognize binding events (and, optionally, to recognize non-binding events) using in vitro measurements and/or in silico predictions. For example, a computation decoding algorithm can be trained using binding measurements carried out in vitro using known affinity agents and known protein targets. Alternatively or additionally, a computational decoding algorithm can be trained using predicted affinity of one or more binding agents for one or more protein epitopes. Optionally, binding events can be weighted differently than non-binding events when used by an algorithm to identify a protein. Alternatively or additionally, binding events observed for one or more affinity agents can be weighted differently than binding events observed for one or more other affinity agents. Binding events and/or affinity agents that are more trusted, for example due to being more consistent, can be weighted more heavily than less trusted events or agents. A computational decoding algorithm, once trained, can be used to build a probability model at each site of an array. Decoding algorithms and methods for training the algorithms are set forth in further detail below. Probability models for each site can be used to assign a degree of confidence to a series of binding events and/or non-binding events at each site and to assign a degree of confidence to the identification of the protein at each site. A protein may be considered identified or characterized if the degree of confidence for a prediction based upon overlaid or combined affinity agent interaction data exceeds a threshold degree of confidence. The threshold degree of confidence for a protein characterization prediction may depend upon the nature of the characterization. The threshold degree of confidence may fall in a range from about 50% to about 99.999%, such as about 50%, 60%, 70%, 80%, 90%, 95%, 99%, 99.99%, or 99.999%. In some cases, the threshold degree of confidence may be outside this range. In some cases, the computational decoding approaches may incorporate machine learning or training algorithms to update or refine the determined or identified probabilistic interaction profile for the affinity agents or proteins with increased information or in ever widening contexts.

Protein characterization by the measurement of affinity agent interactions may be more difficult when the measurements are prone to a degree of systematic or random error or uncertainty. For example, measurement accuracy of affinity agent interactions with proteins (or protein epitopes) may be affected by numerous factors such as system detection limits or sensitivity, non-specific interactions between epitopes and affinity agents (false positives), or stochastic, time-dependent reversal of an interaction (false negatives).

Protein characterization measurements may contain a degree of uncertainty. High-confidence characterization may be achieved by utilizing multiple detection cycles in combination with a probabilistic decoding approach. The overlaying or combining of binary protein interaction data (e.g., affinity agent A1, which interacts with epitope X, was not observed to interact with unknown protein P, therefore, protein P does not contain epitope X) may lead to improper protein characterization due to the inclusion or exclusion of possible candidate states due to measurement error. By contrast, overlaying or combining probabilistic protein interaction data may permit an algorithm to converge to a high-confidence prediction of protein identity without needing to exclude any candidate states. For example, if affinity agents A1 to A6 are known to interact with a known protein P1 with interaction probabilities, and measurable interactions of affinity agents A2, A5 and A6 are observed against an unknown protein P, it may be concluded that protein P is likely not protein P1 (2 of 3 likely interactions were not observed; 2 of 3 unlikely interactions were observed). Moreover, a probability-based characterization may be assigned a degree of confidence such that a prediction for each observed protein may be made when the degree of confidence rises above a threshold degree of confidence. For example, in the above observation of protein P, the six described observations may not provide a high enough degree of confidence to eliminate protein P1 as a possible identity, but similar trends over 20 or more affinity agents may provide sufficient degree of confidence to eliminate P1 as a possible identity. Accordingly, protein P1 can be subjected to binding reactions with a series of promiscuous affinity agents, and although the observation from each binding reaction taken individually may be ambiguous with regard to identifying the protein, decoding the observations from the series of binding reactions may identify protein P1 with an acceptable level of confidence.

Particularly useful methods and algorithms that can be used for detection methods employing multiple detection cycles and/or promiscuous binding agents are set forth, for example, in U.S. Pat. No. 10,473,654; or PCT Publication No. WO 2019/236749 A2; or US Pat. App. Pub. Nos. 2020/0082914 A1 or 2020/0090785 A1, each of which is incorporated herein by reference.

Methods of detecting proteins or other analytes can employ nucleic acid tags. For example, a method of detecting a protein, can include steps of (i) binding a first binding reagent to a sample protein at a site of an array, wherein the binding reagent comprises a nucleic acid tag, and wherein a primer nucleic acid is present at the site; (ii) extending the primer nucleic acid, thereby producing an extended primer having a copy of the tag; and (iii) detecting the tag of the extended primer. The extending of the primer can be carried out, for example, by polymerase based extension of the primer, using the nucleic acid tag as a template. Alternatively, the extending of the primer can be carried out, for example, by ligase or chemical based ligation of the primer to the nucleic acid tag or to a nucleic acid that is hybridized to the nucleic acid tag. The nucleic acid tag can be detected via hybridization to a nucleic acid probe (e.g., in a microarray), amplification-based detection (e.g., PCR-based detection, or rolling circle amplification-based detection) or nucleic acid sequencing (e.g., cyclical reversible terminator methods, nanopore methods, or single-molecule, real time detection methods). Exemplary methods that can be used for detecting proteins using nucleic acid tags are set forth in US Pat. App. Pub. No. 2019/0145982 A1; 2020/0348308 A1; or 2020/0348307 A1, each of which is incorporated herein by reference.

A method of detecting a protein, can include steps of (i) exposing a terminal amino acid on the protein; (ii) detecting a change in signal from the protein; and (iii) identifying the type of amino acid that was removed based on the change detected in step (ii). The terminal amino acid can be exposed, for example, by removal of one or more amino acids from the amino terminus or carboxyl terminus of the protein. Steps (i) through (iii) can be repeated to produce a series of signal changes that is indicative of the sequence for the protein. The signal change can optionally be detected at one or more sites on an array.

In a first configuration of the above method, one or more types of amino acids in the protein can be attached to a label that uniquely identifies the type of amino acid. In this configuration, the change in signal that identifies the amino acid can be loss of signal from the respective label. Exemplary compositions and techniques that can be used to remove amino acids from a protein and detect signal changes are set forth in Swaminathan et al., Nature Biotech. 36:1076-1082 (2018); or U.S. Pat. No. 9,625,469 or 10,545,153, each of which is incorporated herein by reference.

In a second configuration of the above method, the terminal amino acid of the protein can be recognized by a binding reagent that is specific for the terminal amino acid or specific for a label moiety that is present on the terminal amino acid. The binding reagent can be detected on an array, for example, due to a label on the binding reagent. Exemplary binding reagents and detection methods are set forth in US Pat. App. Pub. No. 2019/0145982 A1; 2020/0348308 A1; or 2020/0348307 A1, each of which is incorporated herein by reference.

A method of detecting a protein can include steps of (i) exposing a terminal amino acid on a protein at a site of an array; (ii) binding a binding reagent to the terminal amino acid, where the binding reagent comprises a nucleic acid tag, and where a primer nucleic acid is present at the site; (iii) extending the primer nucleic acid, thereby producing an extended primer having a copy of the tag; and (iv) detecting the tag of the extended primer. The terminal amino acid can be exposed, for example, by removal of one or more amino acids from the amino terminus or carboxyl terminus of the protein. Steps (i) through (iv) can be repeated to produce a series of tags that is indicative of the sequence for the protein. The extending of the primer can be carried out, for example, by polymerase-based extension of the primer, using the nucleic acid tag as a template. Alternatively, the extending of the primer can be carried out, for example, by ligase- or chemical-based ligation of the primer to a nucleic acid that is hybridized to the nucleic acid tag. The nucleic acid tag can be detected via hybridization to nucleic acid probes (e.g., in a microarray), amplification-based detections (e.g., PCR-based detection, or rolling circle amplification-based detection) or nucleic acid sequencing (e.g., cyclical reversible terminator methods, nanopore methods, or single-molecule, real time detection methods). Exemplary methods that can be used for detecting proteins using nucleic acid tags are set forth in US Pat. App. Pub. No. 2019/0145982 A1; 2020/0348308 A1; or 2020/0348307 A1, each of which is incorporated herein by reference. A protein, primer nucleic acid or template nucleic acid copied by extension of the primer can be attached to a SNAP or SNAP complex.

A method of detecting a protein can include determining a detected property such as amino acid sequence, presence of a known epitope, protein size (e.g., mass or number of amino acids), protein isoelectric point, protein hydrophobicity, protein hydrodynamic radius, protein pKa, the presence of a post-translational modification, the absence of a post-translational modification, protein charge, the presence of a non-natural amino acid or cofactor, the conformation of secondary, tertiary, or quaternary structure, the absence of particular secondary, tertiary, or quaternary structures, presence of a bound molecule, or absence of a bound molecule. A bound non-protein molecule may comprise a chelated ion, a bound metal cluster, a bound cofactor (e.g., a porphyrin), a bound ligand, a bound substrate, or a bound biomolecule (e.g., polysaccharide, nucleic acid, protein, etc.).

A protein or other molecular analyte can be detected at single-molecule resolution in a method or assay set forth herein. A protein detection assay that is based on multiple low specificity detection cycles may be configured to permit protein detection or characterization at a single-molecule resolution level. Proteins to be detected in a method set forth herein may be provided on a solid support containing unique, detectably resolvable characterization sites. For example, the proteins can be attached to the sites via attachment to SNAPs. Such characterization sites may be spaced, arrayed, or otherwise ordered to allow individual sites to be distinguished one from another, for example, when detecting their interactions with affinity agents. A solid support may comprise a sufficient number of unique, optically resolvable characterization sites to accommodate a plurality, majority, or all proteins from a sample, such as at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, or more than $1\times10^{12}$ sites.

Decoding Approaches

Methods and systems of the present disclosure may perform decoding approaches for accurate and efficient identification of biological, chemical, and/or physical entities, such as proteins. Such decoding approaches can significantly reduce or eliminate errors in identifying proteins in a sample. Such decoding approaches may achieve accurate and efficient identification of candidate entities such as proteins within a sample of unknown proteins. The protein identification may be based on calculations using information of empirical measurements of the unknown proteins in the sample. For example, empirical measurements may include binding information of affinity agents (e.g., affinity probes) which are configured to selectively bind to one or more candidate proteins, protein length, protein hydrophobicity, and/or protein isoelectric point. The protein identification may be optimized to be computable within a minimal memory footprint. The protein identification may comprise estimation of a confidence level that each of one or more candidate proteins is present in the sample.

A decoding approach of the present disclosure may comprise identifying a protein within a sample of unknown proteins. Embodiments and configurations of the decoding approach can be applied to any of a variety of biological chemical or physical entities, but for sake of illustration may be exemplified herein with regard to proteins. Configurations and embodiments exemplified for proteins can be applied to other entities. The decoding approach may be applied independently to each unknown protein in a sample, to generate a collection of proteins identified in the sample. For example, the decoding approach may be applied independently to individual sites of an array. Protein quantities may be calculated by counting the number of identifications for each candidate protein. Taking as an example an array of proteins, the number of sites in the array that are identified as having a particular candidate protein can be counted and the count can be used to determine the quantity for the candidate protein on the array and/or in the sample from which the protein was obtained. In some configurations, the quantity of a particular protein in a sample or on an array can be determined relative to the amount of one or more other protein in the sample or on the array. For example, a protein of interest can be quantified on an array relative to a quantitation standard. The quantitation standard can be spiked into a sample as an exogenous protein (i.e., not present in the genome from which the protein sample is derived). In other cases, the standard can be an endogenous protein that is known or expected to be present at stable or predictable levels in the genome from which the sample proteins are derived. Alternatively, the quantity of a particular protein in a sample or on an array can be determined in non-relative terms.

Quantitation standards can also be used to calibrate a method or apparatus set forth herein. For example, multiple known proteins can be spiked into an analytical sample, or a plurality of known proteins can be provided in a calibration sample. The known proteins can be delivered at a known quantity (e.g., total quantity, concentration etc.). The known proteins can be detected and analyzed using a method or apparatus set forth herein.

A method for identifying a protein or other entity may comprise receiving, by a computer, information of a plurality of empirical measurements of an unknown protein or entity in a sample. The empirical measurements may include (i) binding measurements of each of one or more affinity agents to one or more of the unknown proteins or entities in the sample, (ii) length of one or more of the unknown proteins or entities; (iii) hydrophobicity of one or more of the unknown proteins or entities; and/or (iv) isoelectric point of one or more of the unknown proteins or entities. The empirical measurements can optionally include a series of signals obtained from performing an amino acid sequencing technique, such as Edman-type degradation, for one or more unknown proteins. In some embodiments, a plurality of affinity agents can be serially contacted with one or more proteins, such that different affinity agents are separately contacted with the one or more proteins. In some embodiments, a plurality of affinity agents may comprise a pool of different affinity agents. Accordingly, a plurality of different affinity agents can be contacted with one of more proteins as a pool of affinity agents, such that the one or more proteins is/are in simultaneous contact with the plurality of affinity agents.

For example, a plurality of affinity agents (whether configured separately or as a pool) may comprise at least 2, 3, 4, 5, 6, 7, 8, 9, 10, 25, 50, 75, 100, 250, 500 or more types of affinity agents, each type of affinity agent differing from the other types with respect to the epitope(s) recognized. Alternatively or additionally, a plurality of affinity agents may comprise at most 500, 250, 100, 75, 50, 25, 10, 9, 8, 7, 6, 5, 4, 3, or 2 types of affinity agents, each type of affinity agent differing from the other types with respect to the epitope(s) recognized. In some embodiments, a pool of affinity agents may comprise 2 types of affinity agents that combined make up a majority of the composition of the affinity agents in the pool of affinity agents. In some embodiments, a pool of affinity agents may comprise 3 types of affinity agents that combined make up a majority of the composition of the affinity agents in the pool of affinity agents. In some embodiments, a pool of affinity agents may comprise 4 types of affinity agents that combined make up a majority of the composition of the affinity agents in the pool of affinity agents. In some embodiments, a pool of affinity agents may comprise 5 types of affinity agents that combined make up a majority of the composition of the affinity agents in the pool of affinity agents. In some embodiments, a pool of affinity agents may comprise more than 5 types of affinity agents that combined make up a majority of the composition of the affinity agents in the pool of affinity agents. Different types of affinity agents in a pool can be uniquely labeled such that the different types can be distinguished from each other. In some configurations, at least two, and up to all, of the different types of affinity agents in a pool may be indistinguishably labeled. Each of the affinity agents in a plurality of affinity agents may be configured to selectively bind to one or more candidate epitopes or proteins among a plurality of candidate epitopes or proteins. The affinity agents may be k-mer affinity agents. In some embodiments, each k-mer affinity agent is configured to selectively bind to one or more candidate proteins or peptides among a plurality of candidate proteins or peptides. The information of empirical measurements may comprise binding measurements of one or more affinity agents that are believed to have bound to an unknown protein or peptide.

At least a portion of the information of empirical measurements of an unknown protein may be compared, by a computer, against a database comprising information for a plurality of proteins, such as amino acid sequences. Each of the proteins may correspond to a candidate protein among the plurality of candidate proteins. The plurality of candidate proteins may comprise at least 10, 20, 30, 40, 50, 60, 70, 80, 90, 100, 200, 300, 400, 500, 600, 800, 1000, or more different candidate proteins. In some embodiments, the database may comprise information other than amino acid sequences. Particularly useful information includes, but is not limited to, binding characteristics for binding of a probe (e.g., affinity agent) to a protein. For example, the database may comprise a binding probability of each of a plurality of probes to each of a plurality of candidate proteins. In another example, the database may comprise an equilibrium binding characteristic (e.g., association constant, $K_a$ or dissociation constant, $K_d$), association rate constant (e.g., $k_{on}$) or dissociation rate constant (e.g., $k_{off}$) of each of a plurality of probes to each of a plurality of candidate proteins. In some embodiments, the binding probabilities or other binding characteristics are derived empirically. In some embodiments, the binding probabilities or other binding characteristics are derived based on the sequence information and epitope-level (e.g., trimer-level in the case of probes that recognize epitopes that are peptide trimers) binding probabilities or other epitope-level binding characteristics for each probe. Similar binding characteristics can be used for binding of affinity agents and other entities besides proteins.

For each of one or more candidate proteins or other entities in a plurality of candidate proteins or entities, a probability that an empirical measurement on the candidate protein or entity would generate an observed measurement outcome may be calculated or generated, by the computer. The term "measurement outcome," as used herein, refers to the information observed on performing a measurement. For example, the measurement outcome of an affinity agent binding experiment may be a positive or negative outcome, such as either binding or non-binding, respectively, of the reagent to a candidate protein. As another example, the measurement outcome of an experiment measuring the length of a protein may be an integer value, such as 417 amino acids. Additionally, or alternatively, for each of one or more candidate proteins in a plurality of candidate proteins, a likelihood or probability that an empirical measurement on the candidate protein would not generate an observed measurement outcome, may be calculated or generated, by the computer. Additionally, or alternatively, a likelihood or probability that an empirical measurement on the candidate protein would generate an unobserved measurement outcome, may be calculated or generated by the computer. Additionally, or alternatively, a likelihood or probability that a series of empirical measurements on the candidate protein would generate an outcome set may be calculated or generated, by the computer.

"Outcome set," as used herein, refers to a plurality of independent measurement outcomes for a protein or other entity. For example, a series of empirical affinity agent binding measurements may be performed on an unknown protein or other entity. When the binding measurement of each individual affinity agent comprises a measurement outcome, the set of all measurement outcomes is an outcome set. In some cases, the outcome set may be a subset of all observed outcomes. In some cases, the outcome set may consist of measurement outcomes that were not empirically observed. Additionally or alternatively, for each of one or more candidate proteins in a plurality of candidate proteins, a probability that the unknown protein is the candidate protein, may be calculated or generated, by the computer. The calculation or generation may be performed iteratively or non-iteratively. The probabilities may be generated based on comparison of the empirical measurement outcomes of the unknown proteins against a database comprising information for candidate proteins such as the amino acid sequences for the candidate proteins. Thus, the input to an algorithm of the present disclosure may comprise a database of information for candidate proteins (e.g., amino acid sequences for the candidates) and a set of empirical measurements (e.g., probes that are believed to have bound to an unknown protein, length of the unknown protein, hydrophobicity of the unknown protein, and/or isoelectric point of the unknown protein) for the unknown protein or peptide. In some cases, the input to an algorithm may comprise parameters relevant to estimating the probability of any of the affinity agents generating any binding measurement for any of the candidate proteins (e.g., trimer-level binding probabilities for each affinity agent). The output of the algorithm may comprise (i) a probability that a measurement outcome or outcome set is observed given a hypothesized candidate protein identity, (ii) the most probable identity, selected from the set of candidate proteins, for the unknown protein and the probability of that identification being correct given a measurement outcome or outcome set, and/or (iii) a group of high-probability candidate protein identities and an associated probability that the unknown protein is one of the proteins in the group. The probability that the measurement outcome is observed given that a candidate protein is the protein being measured may be expressed as:

$$P(\text{measurement outcome}|\text{protein}).$$

In some embodiments, P(measurement outcome|protein) is calculated completely in silico. In some embodiments, P(measurement outcome|protein) is calculated based on, or derived from, features of the amino acid sequence of the protein. In some embodiments, P(measurement outcome|protein) is calculated independent of knowledge of the amino acid sequence of the protein. For example, P(measurement outcome|protein) may be determined empirically by acquiring the measurement in replicate experiments on an isolate of the protein candidate, and calculating the P(measurement outcome|protein) from the frequency: (number of measurements with outcome/total number of measurements). In some embodiments, P(measurement outcome|protein) is derived from a database of past measurements on the protein. In some embodiments P(measurement outcome|protein) is calculated by generating a set of confident protein identifications from a collection of unknown proteins with the results of the measurement censored, and then calculating the frequency of the measurement outcome among the set of unknown proteins that were confidently identified as the candidate protein. In some embodiments, a collection of unknown proteins may be identified using a seed value of P(measurement outcome|protein), and the seed value refined based on the frequency of the measurement outcome among unknown proteins confidently matched to the candidate protein. In some embodiments, this process is repeated, with new identifications generated based on updated measurement outcome probabilities, and then new measurement outcome probabilities generated from the updated set of confident identifications.

The probability that the measurement outcome is not observed given that a candidate protein is the protein being measured, may be expressed as:

$$P(\text{not measurement outcome}|\text{protein}) = 1 - P(\text{measurement outcome}|\text{protein}).$$

The probability that a measurement outcome set consisting of N individual measurement outcomes is observed given that a candidate protein is the protein being measured, may be expressed as a product of the probabilities for each individual measurement outcome:

$$P(\text{outcome } set|\text{protein}) = P(\text{measurement outcome 1}|\text{protein}) * P(\text{measurement outcome 2}|\text{protein}) * \ldots * P(\text{measurement outcome } N|\text{protein}).$$

In some embodiments, each of the candidate proteins in the database is assumed to be equally likely to be found in a given sample. However, in cases where the protein database is extremely large, a non-uniform prior distribution may be appropriate. In some embodiments, the candidate proteins in the database may have a non-uniform prior probability for being present in the sample. For example, certain proteins may be more likely to be present in the sample than others, based on characteristics of the proteins or of the sample, such as the type of sample, the location of the subject from which the sample was obtained, a species of the subject from which the sample was obtained, etc. For example, if the candidate protein database has 1 million possible protein sequences, in some circumstances, it may be difficult to confidently determine that a particular protein being assayed is one given protein among the 1 million candidate proteins. However, if prior information was known or assumed, for example, that 900,000 of the 1 million candidate protein sequences were highly unlikely to occur, then that information may be used to build a representative prior probability that effectively narrows the search space down to 100,000 possible candidate protein sequences, unless the evidence for one of the 900,000 other possible proteins is overwhelming. In the context of de novo sequencing, there may be many millions of possible protein sequences in the candidate database. However, a Markov model may be trained on existing protein sequence databases and used to compute a prior probability that "down-weights" the probabilities of protein sequences that do not appear similar to any protein sequence that has been previously observed.

The probability of an unknown protein being a candidate protein (protein$_i$), may be calculated based on the probability of the outcome set for each possible candidate protein.

In some embodiments, the measurement outcome set comprises binding of affinity agents to proteins or other entities. In some embodiments, the measurement outcome set comprises non-specific binding of affinity agents to proteins or other entities. In some embodiments, a "strict" decoding approach is performed, wherein, for a given set of unknown proteins, only a subset of the candidate proteins is considered, for which the highest probability binding outcome sequence matches the observed measurement outcome set.

In some embodiments, a protein in a sample is truncated or degraded. In some embodiments, the protein in the sample does not contain the C-terminus of the original protein. In some embodiments, the protein in the sample does not contain the N-terminus of the original protein. In some embodiments, the protein in the sample does not contain the N-terminus and does not contain the C-terminus of the original protein. Truncation or degradation of one or more proteins can occur prior to attaching the one or more proteins to an array. In some configurations of the methods set forth herein, truncation or degradation can occur for one or more proteins after attachment of the protein(s) to an array. For example, truncation or degradation can result from an Edman-type sequencing process carried out on an array or from a proteolysis step (e.g., using proteases having known recognition sequences) carried out on an array.

In some embodiments, the empirical measurements comprise measurements performed on mixtures of binding agents (e.g., mixtures of antibodies and/or aptamers). In some embodiments, the empirical measurements comprise measurements performed on samples containing proteins, or other entities, from a plurality of species. For example the sample can be an environmental sample, or microbiome sample. In some embodiments, the empirical measurements comprise measurements performed on a sample derived from humans. In some embodiments, the empirical measurements comprise measurements performed on a sample derived from a different species than human. In some embodiments, the empirical measurements comprise measurements performed on samples in the presence of single amino acid variants (SAVs) caused by non-synonymous single nucleotide polymorphisms (SNPs). In some embodiments, the empirical measurements comprise measurements on samples in the presence of genomic structural variation, such as insertions, deletions, translocations, inversions, segmental duplications, or copy number variation (CNV) affecting the sequence of the proteins in the sample.

A decoding approach set forth herein can be applied to one or more unknown proteins or other entities measured in a sample. For example, a decoding approach can be applied to a subset of unknown proteins measured in a sample. In some embodiments, the decoding approach is applied to all unknown proteins measured in a sample. In some embodiments, the decoding approach further comprises generating, for each of the one or more candidate proteins or other entities, a confidence level that the candidate protein or other entity matches the unknown protein or other entity being measured in the sample. The confidence level may comprise a probability value. Alternatively, the confidence level may comprise a probability value with a measure of error or variation. Alternatively, the confidence level may comprise a range of probability values, optionally with a confidence (e.g., at least about 90%, 95%, 96%, 97%, 98%, 99%, 99.9%, 99.99%, 99.999%, 99.99990%, 99.99999%, 99.999999%, 99.9999999%, 99.99999999%, 99.999999999%, 99.99999999999%, 99.99999999999%, 99.999999999999%, 99.9999999999999% confidence, or greater). In some embodiments, the decoding approach further comprises generating a probability that a candidate protein is present in the sample.

In some embodiments, a decoding approach of the present disclosure further comprises generating protein identifications, optionally with associated probabilities, independently for each unknown protein in the sample. Optionally a list of all unique proteins identified in the sample can be generated. In some embodiments, decoding further comprises counting the number of identifications generated for each unique candidate protein to determine the quantity of each candidate protein in the sample. In some embodiments, a collection of protein identifications and associated probabilities may be filtered to only contain identifications of a high score, high confidence, and/or low false identification rate (e.g., a rate of false-positive identification results).

In some embodiments, binding probabilities may be generated for affinity agents to full-length candidate proteins. In some embodiments, binding probabilities may be generated for affinity agents to protein or peptide fragments (e.g., a subsequence of the complete protein or peptide sequence). For example, if unknown proteins were processed and attached (e.g., conjugated or bound) to a substrate in a manner such that peptide fragments having only the first 100 amino acids of each unknown protein were attached, binding probabilities may be generated for each protein candidate such that all binding probabilities for epitope binding beyond the first 100 amino acids are set to zero, or alternatively to a very low probability representing an error rate. A similar approach may be used if peptide fragments having only the first 10, 20, 50, 100, 150, 200, 300, 400, or more amino acids of each protein are attached to a substrate. A similar approach may be used if peptide fragments having only the last 10, 20, 50, 100, 150, 200, 300, 400, or more amino acids are attached to a substrate. Peptide fragments obtained from internal portions of a protein sequence can be similarly treated. For example, proteolyzing a protein with a protease having known recognition sequences can generate one or more fragments of the protein, and binding probabilities may be generated for each protein candidate such that all binding probabilities for binding of epitopes outside of a sequence region predicted for a retained fragment of each candidate protein can be set to zero, or to a very low probability representing an error rate.

In cases where a single protein candidate match cannot be assigned to an unknown protein, a group of potential protein candidate matches may be assigned to the unknown protein. A confidence level may be assigned to an unknown protein being one of any of the protein candidates in the group. The confidence level may comprise a probability value. Alternatively, the confidence level may comprise a probability value with a measure of error or variability. Alternatively, the confidence level may comprise a range of probability values, optionally with a confidence (e.g., about 90%, 95%, 96%, 97%, 98%, 99%, 99.9%, 99.99%, 99.999%, 99.9999%, 99.99999%, 99.9999990%, 99.9999999%, 99.99999999%, 99.999999999%, 99.9999999999%, 99.999999999999%, 99.9999999999999%, 99.99999999999999% confidence, or above). For example, an unknown protein may match strongly with two protein candidates. The two protein candidates may have high sequence similarity to each other (e.g., two protein isoforms, such as proteins with single amino acid variants compared to a canonical sequence). In these cases, no individual protein candidate may be assigned with high confidence, but a high confidence may be ascribed to the unknown protein matching to a single, but unknown, member of the "protein group" comprising the two strongly matching protein candidates. Similar grouping and determination of confidence levels can be performed for other entities besides proteins.

In some embodiments, efforts may be made to detect cases where unknown proteins or other entities are not optically-resolved. For example, on rare occasion, two or more proteins may bind in the same "well," site or other location of a substrate despite efforts to prevent this occurrence. In some cases, proteins attached to a particular site or location may be treated with a non-specific dye and the signal from the dye measured. In cases where two or more proteins are not optically-resolved, the signal resulting from the dye may be higher than locations containing a single protein and may be used to flag locations with multiple bound proteins.

In some embodiments, the plurality of candidate proteins is generated or modified by sequencing or analyzing the DNA or RNA of the human or other organism from which the sample of unknown proteins is obtained or derived.

In some embodiments, a decoding approach further comprises deriving information on post-translational modifications of one or more unknown proteins. The information on post-translational modifications may comprise the presence of a post-translational modification (PTM) without knowledge of the nature of the specific modification or without knowledge of the location of the modification in the structure of the modified protein. The database may be considered to be an exhaustive combinatorial space of PTMs. For example, once a protein candidate sequence has been assigned to an unknown protein, the pattern of affinity agent binding for the assayed protein may be compared to a database containing binding measurements for the affinity agents to the same candidate from previous experiments. For example, a database of binding measurements may be derived from binding to a Nucleic Acid Programmable Protein Array (NAPPA) containing unmodified proteins of known sequence at known locations.

Additionally or alternatively, a database of binding measurements may be derived from previous experiments in which protein candidate sequences were confidently assigned to unknown proteins. Discrepancies in binding measurements between the assayed protein and the database of existing measurements may provide information on the likelihood of post-translation modification. For example, if an affinity agent has a high frequency of binding to the candidate protein in the database, but does not bind the assayed protein, there is a higher likelihood of a post-translational modification being present somewhere on the protein. If the binding epitope is known for the affinity agent for which there is a binding discrepancy, the location of the post translational modification may be localized to at or near the binding epitope of the affinity agent. In some embodiments, information on specific post-translational modifications may be derived by performing repeated affinity agent measurements before and after treatment of the protein-substrate conjugate with an enzyme that specifically adds or removes the particular post translational modification. For example, binding measurements may be acquired for a sequence of affinity agents prior to treatment of the substrate with a phosphatase, and then repeated after treatment with a phosphatase. Affinity agents which bind an unknown protein prior to phosphatase treatment but not after phosphatase treatment (differential binding) may provide evidence of phosphorylation. If the epitope recognized by the differentially binding affinity agent is known, the phosphorylation may be localized as being at or near the binding epitope for the affinity agent.

In some cases, the count of a particular post-translational modification may be determined using binding measurements with an affinity agent against a particular post-translational modification. For example, an antibody that recognizes phosphates, phosphorylated amino acids or other products of phosphorylation events may be used as an affinity agent. The binding of this reagent may indicate the presence of at least one phosphorylation on the unknown protein. In some cases, the number of discrete post-translational modifications of a particular type on an unknown protein may be determined by counting the number of binding events measured for an affinity agent specific to the particular post-translational modification. For example, a phosphorylation specific antibody may be attached to a fluorescent label. In this case, the intensity of the fluorescent signal may be used to determine the number of phosphorylation-specific affinity agents bound to an unknown protein. The number of phosphorylation-specific affinity agents bound to the unknown protein may in turn be used to determine the number of phosphorylated sites on the unknown protein or peptide. In some embodiments, evidence from affinity agent binding experiments may be combined with pre-existing knowledge of amino acid sequence motifs or specific protein locations likely to be post-translationally modified (e.g., from dbPTM, PhosphoSitePlus, or UniProt) to derive more accurate count, identification, or localization of post-translational modification. For example, if the location of a post-translational modification is not exactly determined from affinity measurements alone, a location containing an amino acid sequence motif frequently associated with the post translational modification of interest may be favored.

In some embodiments, the probabilities acquired from a decoding method set forth herein are iteratively generated until a predetermined condition is satisfied. In some embodiments, the predetermined condition comprises generating each of the plurality of probabilities with a confidence of at least 50%, 55%, 60%, 70%, 80%, 90%, 95%, 99%, 99.9%, 99.99%, 99.999%, 99.99990%, 99.99999%, 99.999999%, 99.9999999%, 99.99999999%, 99.999999999%, 99.99999999990%, 99.99999999999%, 99.999999999999%, 99.9999999999999% confidence, or above.

In some embodiments, decoding further comprises generating a report (e.g., a paper or electronic report) identifying one or more unknown proteins or other entities in a sample. The report may further indicate, for each of the candidate proteins or entities, a confidence level for a particular candidate protein or entity being present in the sample. The confidence level may comprise a probability value. Alternatively, the confidence level may comprise a probability value with an error. Alternatively, the confidence level may comprise a range of probability values, optionally with a confidence (e.g., about 90%, 95%, 96%, 97%, 98%, 99%, 99.9%, 99.99%, 99.999%, 99.9999%, 99.99999%, 99.999999%, 99.9999999%, 99.99999999%, 99.999999999%, 99.9999999999%, 99.99999999999%, 99.999999999999%, 99.9999999999999% confidence, or above). A report may further indicate the list of protein candidates (or other entity candidates) identified as being below an expected false identification rate threshold (e.g., a false identification rate below 10%, 9%, 8%, 7%, 6%, 5%, 4%, 3%, 2%, 1%, 0.5%, 0.4%, 0.3%, 0.2%, or 0.1%). The false identification rate may be estimated by first sorting the protein or entity identifications in descending order of confidence. The estimated false identification rate at any point in the sorted list may then be calculated as 1−avg_c_prob, where avg_c_prob is the average candidate probability for all proteins or entities at or before (e.g., higher confidence than) the current point in the list. A list of protein or entity identifications that fall below a desired false identification rate threshold may then be generated by returning all protein or entity identifications before the earliest point in the sorted list where the false identification rate is higher than the threshold. Alternatively, a list of protein or entity identifications that fall below a desired false identification rate threshold may be generated by returning all proteins or entities before, and including, the latest point in the sorted list where the false identification rate is below or equal to the desired threshold.

In some embodiments, a sample used in a method or system set forth herein comprises a biological sample. The biological sample may be obtained from a subject. In some embodiments, the decoding approach further comprises identifying a disease state or a disorder in the subject based at least on the plurality of probabilities. For example, the plurality of probabilities may indicate the presence or absence of a protein or other entity that is correlated with the presence, absence, duration, severity or outcome of a treatment, condition, disease state or disorder.

In some embodiments, a decoding approach further comprises quantifying proteins or other entities by counting the number of identifications attributed to a particular protein or entity candidate. For example, the absolute quantity (e.g., number of protein molecules) of a protein present in a sample can be calculated by counting the number of detected species that have been assigned confident identifications generated from that protein or entity candidate. In some embodiments, the quantity may be a relative quantity, for example, being calculated as a ratio or percentage of the total number of unknown proteins or entities assayed. In some embodiments, the identification counts may be calibrated to remove systematic error from the instrument and detection systems. In some embodiments, the quantity may be calibrated to remove biases in quantity caused by variation in detectability of protein or entity candidates. Detectability of a protein or other entity may be assessed from empirical measurements or computer simulation.

In some embodiments, a protein abundance may be determined using systems and methods of the present disclosure. For example, the protein abundance may comprise a differential protein abundance, a relative protein abundance, an absolute protein abundance, or a combination thereof.

As an example, protein abundance may comprise a differential protein abundance, which is indicative of the degree to which a given protein changes in abundance from a first sample to a second sample. For example, determining a differential protein abundance may comprise determining that a first protein has increased in abundance by 50% in a sample from a diseased tissue or subject as compared to another sample from a control tissue or control subject, while a second protein or peptide has not changed in abundance across the two samples. In this case, the relative amount of the first and second proteins may not be known.

As another example, protein abundance may comprise a relative protein abundance, which is indicative of the degree to which a first protein is present in a sample relative to a second protein or a total amount of proteins. For example, determining a relative protein abundance may comprise determining that a first protein is present in a sample in an amount that is a certain ratio, percentage or multiple relative to the amount of a second protein that is present in the sample (or alternatively, determining that a first protein is present in a sample as a ratio or percentage of the total amount of protein in the sample). For example, determining a relative protein abundance may comprise determining that there is about 2 times, 3 times, 4 times, 5 times, 10 times, or more of a first protein as compared to a second protein in a sample. The quantity of a protein or other entity can be determined relative to a protein or other analyte that is considered an internal standard. The internal standard can be endogenous to the sample from which the quantified protein or entity is derived or it can be exogenous to the sample, for example, having been introduced by a genetic engineering technique. In some embodiments, determining a relative abundance of a protein or other entity comprises calibrating the sensitivity of the assay between various proteins or entities.

As another example, protein abundance may be indicated as an absolute protein abundance, which is indicative of an amount or quantity (e.g., a count of proteins, or an amount of weight of proteins) of each protein in the sample. For example, determining an absolute protein abundance may comprise determining that a given sample contains 5,000 counts of a first protein and 10,000 counts of a second protein. In some embodiments, determining the absolute protein abundance further comprises determining a concentration of each of a set of proteins in the sample, a mass of each of a set of proteins in the sample, or the number of molecules of each of a set of proteins in the sample.

A disease or disorder that is associated with a sample, protein or other entity may be an infectious disease, an immune disorder or disease, a cancer, a genetic disease, a degenerative disease, a lifestyle disease, an injury, a rare disease or an age-related disease. The infectious disease may be caused by bacteria, viruses, fungi and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, multiple sclerosis (MS), cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (copd), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash.

In some embodiments, a decoding approach comprises identifying and quantifying small molecules (e.g., metabolites, vitamins, enzyme cofactors) or glycans instead of, or in addition to, proteins or peptides. For example, affinity agents, such as lectins or antibodies which bind to sugars or combinations of sugars with varying propensity, may be used to identify glycans. The propensity of the affinity agents to bind various sugars or combinations of sugars may be characterized by analyzing binding to a commercially-available glycan array. For example, unknown glycans may be conjugated to a functionalized substrate using hydroxyl-reactive chemistry and binding measurements may be acquired using the glycan-binding affinity agents. The binding measurements of the affinity agents to the unknown glycans on the substrate may be used directly to quantify the number of glycans with a particular sugar or combination of sugars. Alternatively, one or more binding measurements may be compared to predicted binding measurements from a database of candidate glycan structures using the methods described herein to identify the structure of each unknown glycan. In some embodiments, proteins are bound to a substrate and binding measurements with glycan affinity agents are generated to identify glycans attached to the proteins. Further, binding measurements may be made with both glycan and protein affinity agents to identify a protein backbone sequence and conjugated glycan in a single experiment or using a single solid support. As another example, metabolites may be conjugated to a functionalized substrate using chemistry targeted toward coupling groups that may be found in metabolites such as sulfhydryl, carbonyl, amine, or active hydrogen. Binding measurements may be made using affinity agents with different propensities to particular functional groups, structural motifs, or metabolites. The resulting binding measurements may be compared to predicted binding measurements for a database of candidate small molecules, and the methods described herein may be used to identify the metabolite at each location on the substrate.

The present disclosure provides systems and methods for acquiring pixel information from an array of biological, chemical, or physical entities; and detecting components of the array of biological, chemical, or physical entities based at least in part on the acquired pixel information. In some embodiments, the pixel information is represented by image data, which is analyzed to detect components of the array of biological, chemical, or physical entities via computational decoding. The results of such computational decoding may be integrated with other data for various downstream analyses.

In some embodiments, systems and methods of the present disclosure generate or manipulate pixel information acquired by a light sensing device from an array of biological, chemical, or physical entities. The systems and methods are exemplified herein in the context of light sensing devices. Various configurations of the systems and methods can be extended to other detection devices. For example, systems, methods and algorithms set forth herein in the context of classifying the pixel subcomponents of light sensing device can be applied to individual subcomponents of other detectors such as transistors of FET, ISFET or other electronic detectors, or nanopores of a nanopore array.

Processing of pixel information may be performed using one or more instruments and instrument controls. Such instrument controls may include hardware and/or software to acquire data and process the data using one or more algorithms. The instruments may include light-sensing devices such as scientific-grade CMOS cameras, TDI cameras or other imaging devices. The light sensing devices can optionally be coupled with one or more excitation sources, for example, lasers, light emitting diodes (LEDs), arc lamps or other energy sources. The instrument can optionally include sample handling components, such as a stage configured to position an array or other sample with respect to a detection device. In some configurations, a stage and detector (e.g., light sensing device) can be translated relative to each other, for example, to facilitate scanning an area of an array or other sample that is larger than the detector's field of view (e.g., translation in one or both of the X and Y dimensions), or to adjust focus (e.g., translation along the Z dimension during autofocus or manual focus). The translation system can optionally include one or more X-Y translation stages and/or Z translation stage configured to move a sample (e.g., an array) and one or more light sensing devices (e.g., cameras) with respect to each other, thereby acquiring a scanned image of the sample. The instrument can optionally include a fluid handling systems (e.g., a microfluidics system and/or liquid handling robot) to deliver sample fluids into a flow cell and onto a functionalized surface where data acquisition is performed. Optionally, the fluid handling system can be configured to remove samples from a flow cell or functionalized surface. In some embodiments, X-Y stages and/or Z stages are used to transport a sample to and from various portions of a fluid handling system. In some embodiments, the system comprises a plurality of such X-Y stages and/or Z stages, for example, either to achieve increased parallelism of sample handling or to dedicate each stage to a certain physical area of the system. As an example, additional hardware may be used to transfer components of the system, such as flow cells, from one stage to another. The instrument can further include a temperature control system. For example, temperature control can be provided by controlling temperature of an internal chamber that houses an array or other fluidic component. Alternatively or additionally, an array or other fluidic component can be placed into contact with a thermally conductive surface that is temperature controlled, such as the surface of a stage. Exemplary components that can be adapted for use in an instrument set forth herein are described, for example, in WO 04/018497; WO 07/123,744; U.S. Pat. Nos. 10,858,703 7,329,492; 7,211,414; 7,057,026; 7,315,019; 7,405,281, or U.S. Pat. App. Pub. No. 2008/0108082 A1, each of which is incorporated herein by reference in its entirety.

Instrument controls may include commercially available or custom hardware, including software (e.g., drivers) necessary to control and operate the hardware. For example, such drivers may be configured to prepare light sensing devices (e.g., cameras) to acquire a sequence of one or more images, and then trigger the light sensing devices to acquire image data at certain times or time intervals. A set of drivers may be constructed (e.g., conforming to public specifications) to encode the desired functionality of associated hardware such as detection and/or fluidics instruments. For example, liquid handling systems may use microfluidics to transfer reagents onto a surface, and then signals can be acquired from analytes or binding agents with which they interact (e.g., an image acquisition system may acquire image data of the surface of an array using light sensing devices). An exemplary detection system may comprise one or more cameras, one or more lasers, a stage and an actuator to effect relative motion between the stage and optics. In some embodiments, drivers are configured to control a plurality of different hardware components in concert to acquire pixel information of an array of biological, chemical, or physical entities (e.g., using a set of a few hundred affinity binding reagents on proteins of interest in a sample that is immobilized on a surface).

Pixel information (e.g., camera image data) acquired according to a method set forth herein may be in a suitable format for downstream computational processing, such as color (e.g., RGB) or grayscale images, where individual pixels of the pixel information include an intensity of light at one or more wavelengths (e.g., corresponding to differently colored lasers or fluorescence channels). Optionally, the acquired pixel information can include metadata such as wavelength of luminescence emission detected, wavelength of excitation energy used to produce luminescence, pixel position, excitation exposure time, focus metrics, information acquired from an autofocus system, environmental conditions experienced by the light sensing device such as temperature or vibration, timing of detection relative to shifting of electrons in a charge-coupled device (CCD) operating in time delay integration (TDI) mode, relative location of pixels with respect to the motion of a stage (e.g., information received from an encoder), levels of background signals, correction for background signals, corrections for aberrations in the optical train used to transmit radiation to the pixel, or the like. In particular configurations, biological entities, chemical entities, physical entities or other analytes can be located on the surface of a solid support, for example, at sites in an array. At each location where image data is acquired (e.g., a site in the array of biological, chemical, or physical entities), a set of single-channel, dual-channel, or multiple-channel images can be acquired. An image can be acquired at different stages of array processing. For example, an image can be acquired to identify the location of sites in an array prior to delivering a binding agent or other assay reagent to the array. Accordingly, pixel information acquired from a light sensing device that observes the array can include metadata including, for example, characteristics of a fluid in contact with the array, such as temperature, composition, refractive index or viscosity; location of the array or sites in the array derived from a stage encoder or image registration algorithm; cycle number for a multicycle process carried out on the array; or the like. Optionally, an image can be acquired to detect the presence of a given affinity binding reagent (e.g., after introducing the affinity binding reagent into the sample, such as by incubation).

Optionally, a scanning technique (e.g., raster scanning, line scanning or step-and-shoot scanning) is used to image surfaces that are larger than the field of view for the detection optics. One or both of the optics and surface can be moved relative to the other to achieve scanning. For example, light sensing devices can be moved across an experimental surface to capture images at the desired locations, times or time intervals. Images of array subregions can be combined into a larger image before or after any image processing steps set forth herein.

Whether or not a scanning technique is used, a method or system of the present disclosure can be configured to detect one or more species of analyte (e.g., whether the analytes function as probes or targets), for example, in an array of sites that are attached to the analyte(s). In some configurations, two or more different analytes can be simultaneously present in an array (or other format for presenting analytes) and the different analytes can be detected based on characteristics that are distinguishable by the detector being used. For example, acquiring dual-channel or multiple-channel images may advantageously allow, for example, two different labeled affinity agents (i.e., "LOBEs") to be imaged (e.g., each LOBE species being imaged using a different channel of the multiple channels). Multichannel detection of distinguishable LOBEs can provide an advantage of increasing speed and/or efficiency of operation because, in many systems, delivering a mixture of LOBES to an array and imaging the array via multiple channels is faster than serially delivering individual LOBEs to the array and imaging the array in a single channel after each delivery. For configurations in which two or more different LOBEs are in simultaneous contact with a protein sample, the LOBEs can be selected to have a low likelihood of influencing binding of each other to one or more protein suspected of being in the sample. For example, the different LOBEs can bind to different proteins in the sample (e.g., the LOBES do not bind to the same protein) or the different LOBEs can bind to sites in a protein that are spatially separated from each other in the protein.

A method set forth herein can be carried out in a multi-cycle format in which each cycle includes one or more steps, and in which the cycles are repeated, for example, with different conditions used from one cycle to another. For example, each of the cycles can differ with respect to the type of binding agent that is delivered to an array and detected in the array. Upon completing a cycle for a given binding agent (or pool of binding agents), the process may be repeated for a plurality of binding agents or pools (e.g., for a plurality of at least about 2, 3, 4, 5, 6, 7, 8, 9, 10, 20, 30, 40, 50, 100, 250, 500, or more binding agents or pools of binding agents). In some configurations, the process may comprise repeated measurements or image acquisition operations by looping over a set of colors (e.g., repeated measurements using different excitation wavelengths or emission wavelengths), then over a set of locations, then over a set of binding agents. In another exemplary configuration, the process may comprise repeated measurements or image acquisition operations by looping over a set of binding agents, then over a set of locations, then over a set of colors (e.g., excitation or emissions wavelengths). The image(s) obtained from each individual cycle of a multi-cycle process can optionally be registered to a common coordinate system via an image registration process. Image registration methods may be exemplified herein in the context of "SNAP gridding" which can be used to identify the location of sites that are occupied by structured nucleic acid particles (SNAPs) with reference to a common coordinate system. The SNAPs can be detected via a channel that is configured to acquire signals from SNAPs without necessarily detecting analytes attached to the SNAPs. Alternatively, the process may not comprise acquiring images via the SNAP channel, and instead may comprise acquiring images via a LOBE detection channel. A plurality of LOBEs (e.g., N LOBEs) may be processed all together simultaneously, thereby enabling N-channel imaging to be performed, all for N different LOBE channels. SNAP gridding can be performed using images from the SNAP channel and/or LOBE channel. Alternatively or additionally to processing images using SNAP gridding, the image(s) obtained from each individual cycle of a multi-cycle process can optionally be processed using LOBE finding to identify or locate binding events at sites of an array. SNAP gridding and LOBE finding are set forth in further detail below.

When a detection process of the present disclosure comprises repeated measurements or image acquisition operations for a set of locations (e.g., repeated passes over an area of landing sites on a SNAP array), the imaging pattern may change from pass to pass. In some configurations, one pass employs detection via a first detection channel (e.g., to detect a first type of luminescent label) and another pass employs detection via a second detection channel. The imaging pattern can change due to differences in the detection channels such as intensity of signals detected, presence or characteristics of wavelength-dependent optical aberrations, or wavelength-dependent differences in focus. In some cases, changes from pass to pass may be due to the use of affinity agents that bind different sites in an array due to differences in specificity of the binding agents for the different analytes present at the respective sites. A site may produce signal in a first image of an array due to binding of a first affinity agent to an analyte at the site. Upon replacement of the first affinity agent with a second reagent, signal is not expected to be produced at the site if the second affinity agent does not bind the analyte at the site (and if the first reagent is properly removed by the replacement procedure). Thus, images of an array that are acquired after delivery of different binding agents can have a different pattern of signal producing sites (e.g., sites bound to an affinity agent) and non-signal producing sites (e.g., sites not bound to an affinity agent). Imaging patterns acquired from two scans can also differ due to hardware operational variance. For example, in a first pass, the imaging may be performed from the left of the array to the right of the array (e.g., over a given row), whereas for a second pass, the imaging may be performed in reverse, from the right of the array to the left of the array (e.g., over another given row). As another example, in a first pass, the imaging may be performed from the right of the array to the left of the array (e.g., over a given row), whereas for a second pass, the imaging may be performed in reverse, from the left of the array to the right of the array (e.g., over another given row). As another example, in a first pass, the imaging may be performed from the bottom of the array to the top of the array (e.g., over a given column), whereas for a second pass, the imaging may be performed in reverse, from the top of the array to the bottom of the array (e.g., over another given column). As another example, the imaging pattern may comprise a spiral pattern, such as starting from the outside locations and proceeding inward, or starting from the inside locations and proceeding outward.

Individual sites in an array may be in one of multiple different states. For example, a given site may be empty. Alternatively, a site may be occupied by a SNAP or other linker moiety that is capable of mediating attachment of an analyte to the site, but not occupied by an analyte or analyte label. Alternatively, a site may be occupied by a SNAP or other linker and also occupied by an analyte. Optionally, the analyte may have a label or may be devoid of any label. The present disclosure provides methods for determining the state of the individual sites in the array. For illustrative purposes, configurations of the methods are exemplified herein using landing sites as exemplary array sites, proteins as exemplary analytes, SNAPs as exemplary linkers for attaching proteins to landing sites, and LOBEs as exemplary affinity agents. In some embodiments, detecting components of an array (e.g., an array of biological, chemical, or physical entities) is based at least in part on acquired pixel information and includes a SNAP gridding process for determining a plurality of locations corresponding to locations of SNAPs in an array. In some embodiments, detecting components of an array of biological, chemical, or physical entities is based at least in part on acquired pixel information and includes a process of determining whether a LOBE has bound to a biological, chemical, or physical entity present at one or more of the landing sites. This process may be referred to as "LOBE finding". The outputs of SNAP gridding and LOBE finding steps may be combined as part of a pixel information acquisition process. Compositions and methods exemplified herein with respect to LOBEs can utilize any of a variety of binding agents or other probes instead of the LOBEs. Moreover, compositions and methods exemplified herein with respect to SNAPs can utilize any of a variety of regions on a solid support or sites in an array whether SNAPs are present or not.

In some configurations, SNAP gridding may be performed to process an image that is acquired from an array of landing sites, for example, an array including an irregular pattern of sub-arrays where one or more regions of the pattern is interrupted by a sub-region lacking landing sites (e.g., a center knock out, that can optionally function as a fiducial). SNAP gridding can produce a set of pixel coordinates for every landing site (e.g., location on the surface where an affinity binding reagent may have landed and bound to an entity) that exists in an image or portion(s) of an image. The pixel coordinates may correspond to one or more pixels and/or may have a sub-pixel precision. For example, if an image has 2048×2048 pixels, the coordinate space may comprise any continuous value from 0 to 2048 (e.g., a given coordinate may be, for example, (12.25218, 28.28922905)). SNAP gridding may comprise identifying every sub-array (or other region) in an image based on analyzing a regular or periodic pattern of the image, so that a set of landing sites where proteins of interest may be found can be determined. This process may include accounting for noise that may be present in the acquired image data (e.g., by applying a de-noising, filtering, or background subtraction operation to the data).

Optionally, SNAP gridding may comprise preprocessing image data to clean up or correct any artifacts. For example, one or more lens or other optical component used in an optical detection device may introduce some amount of non-linear artifacts into the acquired image data, which may be removed. For example, an operation to correct fish-eye aberrations, focus aberrations or other optical aberrations may be applied to the images to obtain a normal perspective. In another example, preprocessing can be used to correct for non-uniformity of illumination such as correction of radial components, linear components or a superposition of radial and linear components that produce artifacts when detecting luminescence signals. Preprocessing can be used in some systems to correct for characteristics of individual pixels that may affect detection accuracy. In a particular configuration, a parameterized function can be fit to the overall intensity for an individual pixel and then a number of standard deviations for the pixel value above or below that function can be determined. The number of standard deviations can be represented by a standard score (e.g., z score). The parameterized function can be based, for example, on empirical background measurements acquired prior to performing an analytical measurement or while performing an analytical measurement. Alternatively or additionally, a parameterized function can derive from modeled properties of a system or selected component parts.

Optionally, SNAP gridding may comprise processing image data to account for rotational effects in the image (e.g., a de-rotation operation). For example, the surface of a solid support may have sub-arrays in a regular pattern, which facilitates the alignment (e.g., northeast/southwest alignment) of the image acquired from the surface. Therefore, a de-rotation operation may be performed to account for rotational misalignment of the hardware relative to the surface. For example, this de-rotation may be performed by applying a two-dimensional (2-D) transform, such as a Fourier transform (e.g., a discrete Fourier transform or a continuous Fourier transform) or a fast Fourier transform (FFT) (e.g., a discrete FFT or a continuous FFT) to the image data, to obtain an image signal in the frequency domain. The image signals in the frequency domain may be analyzed to identify high-intensity frequency signals at locations where frequencies of landing sites may be expected to be high (e.g., based on a known spacing of the array). By drawing lines from the origin to such locations, a set of angles may be measured, and statistical measures, such as mean or median, may be used to combine the set of angles into a single angle. The image may then be de-rotated using the single angle by software processing of the image data. Further, the results of the 2-dimensional FFT may be used to not only determine the rotation angle within the image, but also the zoom amount. At different levels of zoom, the distance between the landing sites in an image of the chip may vary, which may change the frequency of the signal, which in turn may change the areas where the strongest frequency responses are located. By measuring the distance of these areas from the origin in the FFT result image, the observed spacing of the landing sites may be determined. This information may be used to construct a template, which may be applied by sliding across the entire image to determine the locations where the strongest response is measured. This may advantageously increase the robustness and reliability of measurements, since the application of a template having a degree of mismatch with the spacing observed in the image may produce spurious and/or erroneous results. Optionally, SNAP features in an image can be sharpened by deconvolving with a small, localized kernel which exemplifies an ideal SNAP signal. A point spread function can be used for convolving the features with the kernel.

Optionally, SNAP gridding may comprise locating and identifying sub-arrays based on image data. For example, a template of an optimal image may be created, and specific positions and/or magnification levels may be measured from such a template. These possible templates may then be applied to empirical image data to identify which template produces the strongest match. For example, matches may be evaluated using a statistical measure or metric, such as a correlation (e.g., a Pearson correlation coefficient), to assess the quality of a match with an image. Alternatively, matches may be evaluated using other methods of assessing the match, such as a dot product or any number of distance metrics.

Upon identifying a template for an array image, the locations of the sites may be identified. Alternatively, the image data may be collapsed into two one-dimensional (1-D) sums of pixels in a column, and then the resulting graphs may be used to find sub-arrays. This may be performed using summation algorithms, such as calculating a sum, mean, and/or median. A fast Fourier transform may be applied to the summed-histogram data to identify a regular pattern of high-intensity and low-intensity values, wherein high-intensity values indicate where landing sites in a column align, and low-intensity values lie in between. In some embodiments, the phase of the highest frequency component from the FFT is used to determine an offset of the landing sites from the set of pixels in the image. For example, the grid of landing sites may be determined to be offset by at least about +/−2 pixels, 1.8 pixels, 1.6 pixels, 1.5 pixels, 1.4 pixels, 1.2 pixels, 1.0 pixel, 0.8 pixels, 0.6 pixels, 0.5 pixels, 0.4 pixels, 0.2 pixels, or relative to the first pixel in the image.

In some configurations of the methods or systems set forth herein, the location and spacing of landing sites can be determined in view of the Nyquist limitation. For some images, spacing between landing sites can be calculated using the fast Fourier transform (FFT). Other calculation methods may be preferred, for example, in cases where resolution is affected by or approaches the Nyquist limitation. This may be the case for some systems where the spacing between landing sites is less than 2 pixels. In some embodiments, determining the landing site spacing comprises interpolating and then performing the discrete Fourier transform (DFT) operation.

Further, SNAP gridding may comprise performing one or more de-noising operations. This process may include accounting for noise that may be present in the acquired image data (e.g., by applying a de-noising, filtering, or background subtraction operation to the data).

The SNAP gridding methods set forth herein are particularly useful for registering or otherwise characterizing arrays in which sites are spatially arranged in a repeating, uniform or periodic pattern, such as a rectilinear grid or hexagonal grid. In some embodiments, methods and systems of the present disclosure are applied to "non-gridded" arrays of biological, chemical, or physical entities. Such arrays can be configured as high-density, single-molecule arrays. For example, such an array may have SNAPs present at sites that are not necessarily arranged in a repeating, uniform or periodic grid. In some cases, non-gridded arrays can be registered using a method other than a SNAP gridding method set forth herein. For example, non-gridded arrays can optionally be registered based on comparison and alignment of sites across multiple images of the array, for example, images acquired in the course of a multicycle process set forth herein. Even if SNAP gridding is not used to register images from a non-gridded array, the presence or absence of a label at particular sites can be determined using a LOBE detection algorithm set forth herein. Moreover, a LOBE detection algorithm may be applied to images acquired from a SNAP detection channel to locate the site centers, for example, rather than applying a SNAP gridding approach.

In some embodiments, methods and systems of the present disclosure are applied to arrays of biological, chemical, or physical entities that have a fixed (e.g., periodic) spacing between landing sites, but are not shaped like a square grid. For example, the array may be arranged similar to a square with the corners trimmed in somewhat, for purposes of facilitating image processing to align a sub-array. As another example, one or more landing sites of a grid may be removed (e.g., randomly) from an image to facilitate the localization and/or identification of a sub-array. A particularly useful arrangement is a hexagonal grid of landing sites. A hexagonal arrangement of landing sites can be advantageous in providing a higher density of landing sites in a given area while retaining a pitch (i.e., center-to-center spacing of nearest neighbor landing sites) that allows neighboring landing sites to be resolved. An array grid can further include fiducials that interrupt or intervene an otherwise regular repeating pattern. The fiducials can be used to register multiple images of an array with respect to each other. Alternatively or additionally, the relative shape, relative size or relative orientation of two or more sub-regions of an array can be used as a fiducial for registering multiple images of the array with respect to each other. The sub-regions can occur in a single field of view or in a composite image obtained by knitting together images from multiple fields of view.

In some embodiments, methods and systems of the present disclosure are applied to arrays of biological, chemical, or physical entities using unlabeled SNAPs. Labeled SNAPs can be used instead of, or in addition to, unlabeled SNAPs. For example, a small amount of labeled SNAPs (e.g., about 0.1%, 0.2%, 0.3%, 0.4%, 0.5%, 0.6%, 0.7%, 0.8%, 0.9%, or 1%) may be spiked into a plurality of otherwise unlabeled SNAPs or into a plurality of SNAPs having a label that is detected in a different channel, such as the channel used to detect LOBEs. The labeled SNAPs may be considered as "anchor SNAPs" for image alignment. A label on the anchor SNAPs can be detected in the same channel used to detect LOBEs and/or in a SNAP channel that is different from the LOBE channel. For example, SNAPs may be deposited, and the LOBE channel may be imaged prior to passing any LOBEs over the chip to detect the random pattern of anchor SNAPs at each subarray. Alternatively or additionally, anchor SNAPs can have a label that is detected in a channel other than the channel used to detect LOBEs. A random pattern of anchor SNAPs may be used to uniquely identify each subarray. As another example, a pattern of anchor SNAPs may be used to easily determine the location of one or more subarray. This may be done, for example, as follows: prior to the experiment being run, use bright field imaging and a highly accurate SNAP gridding algorithm to grid every subarray. This may be a time-consuming process, but produces an accurate gridding for each subarray. Next, SNAPs may be deposited, and the anchor SNAPs may be imaged, to determine the relationship between each anchor SNAP pattern and each highly accurate SNAP gridding alignment. In future runs, the SNAP anchor image (which was collected when imaging LOBEs) may be used to localize the subarray. When performing the protein decoding, the anchor SNAPs may be ignored, since they may all be measured as positive light-up events.

LOBE finding, may be performed to determine a set of coordinates where LOBEs are found, e.g., locations in images where affinity agents appear to bind their target proteins. The LOBE detection (e.g., LOBE finding) may comprise performing a thresholding operation to binarize the image data. For example, fixed or adaptive thresholding may be applied to binarize the image data (e.g., such that individual pixels are designated as ON or OFF, indicative of an event being present or absent, respectively). Image data used for locating LOBEs can be based on the raw pixel values for pixels in the image. Alternatively or additionally, image data can be based on a function or algorithmically determined score for the pixels in an image. For example, a standard score (e.g., z score) derived from a parameterized function fitted to the overall intensity for individual pixels can be used. A connected components analysis may be performed, such that pixels in close proximity are clustered together, while disconnected pixels (not in close proximity to other pixels) are placed into separate clusters. The clusters may be analyzed to determine whether or not a given cluster is a LOBE event (e.g., a positive result indicative of a site where a LOBE has bound), a LOBE non-event (e.g., a negative result indicative of a site where a LOBE is not bound), or an indeterminate event (e.g., an indeterminate result that is not indicative of whether or not a LOBE is bound at the site). In some embodiments, the cluster analysis comprises performing a size-based filtering, enrichment, or exclusion of a subset of the clusters based on their size. For example, clusters that are too small (e.g., smaller than a given lower threshold) or too large (e.g., larger than a given higher threshold) may be excluded as non-events, while clusters that fall into a given range (e.g., between a given lower threshold and a given higher threshold) may be included as LOBE events, thereby producing a set of coordinates where LOBE events are found. The LOBE finding may overcome challenges with identifying binding events, especially in cases where the image data has a low signal-to-noise ratio (SNR), such that the signal is just above the background noise level. This approach may be referred to as an "object-first" LOBE detection approach.

Alternatively, LOBE detection (e.g., LOBE finding) may be performed using a "site-first" approach as follows, which may be able to handle some difficult cases more elegantly. In the "site-first" approach, rather than treating SNAP gridding and LOBE detection as being parallel operations, such operations may instead be performed serially, such that the results of the SNAP gridding (e.g., the coordinates for each, and optionally every, landing site) are used to assist with performing LOBE finding. Landing sites are array sites that are capable of attaching (e.g., covalently or non-covalently) to a SNAP or other entity. The methods exemplified herein for landing sites can be carried out using other array sites. The "site-first" approach leverages the fact that since the expected locations of the landing sites in the LOBE channel image may be known apriori (even though they may not be observed on that image), the locations where LOBEs are searched for may be restricted, focused, or confined to a certain range of pixels in proximity to (e.g., centered around) the landing site coordinates, rather than across the entire image. In particular, this approach may advantageously avoid certain false-negative failure modes, such as those arising in cases in which a plurality of LOBEs (e.g., two LOBEs) happen to be located in proximity to each other, and appear during processing as a single larger cluster of pixels. Aberrantly large clusters may be discarded or filtered out based on the application of size thresholds (e.g., because they have a larger size than the maximum upper-limit size threshold for a single site or LOBE). With the "site-first" approach, such large clusters may be split apart into the individual (e.g., two or more) constituent LOBEs because the regions being analyzed may only include a portion (e.g., half) of the large cluster at a time. Image data used for the site first approach can be based on the raw pixel values for pixels in the image and/or a function or algorithmically determined score for the pixels in the image.

A method of the present disclosure can include a step of processing a set of pixels (e.g., a cluster of pixels) using a trained algorithm (e.g., a classifier) in order to classify each of the clusters. The clusters can be classified, for example, as an event of interest, a non-event of interest, or an indeterminate event. Other exemplary classifications include confidence level that an entity has been detected by the pixels, confidence level that a reaction or other process has been detected by the pixels, a count of the number of entities or processes detected by the pixels, or a probability distribution of the number of entities or processes detected by the pixels. The event of interest can be presence of a binding agent bound to an analyte of interest, presence of a signal producing label added to an analyte of interest in an enzymatic or chemical reaction, presence of a signal produced from a reporter molecule in the presence of an analyte of interest, or the like. For ease of illustration, pixel processing may be exemplified below in the context of LOBE events. However, the pixel processing methods can be applied to other events of interest such as events arising from a protein detection assay.

In some embodiments, LOBE detection (e.g., LOBE finding) may comprise processing a set of pixels (e.g., a cluster of pixels) using a trained algorithm (e.g., a classifier) in order to classify each of the clusters as a LOBE event, a LOBE non-event, or an indeterminate event. A classifier may comprise a machine learning algorithm such as a supervised machine learning algorithm, a semi-supervised machine learning algorithm, or an unsupervised machine learning algorithm. A classifier may comprise a classification and regression tree (CART) algorithm. A classifier may comprise, for example, a support vector machine (SVM), a linear regression, a logistic regression, a nonlinear regression, a neural network, a Random Forest, a deep learning algorithm, a naïve Bayes classifier, or a combination thereof. A classifier may comprise an unsupervised machine learning algorithm, e.g., clustering analysis (e.g., k-means clustering, hierarchical clustering, mixture models, DBSCAN, OPTICS algorithm), principal component analysis, independent component analysis, non-negative matrix factorization, singular value decomposition, anomaly detection (e.g., local outlier factor), neural network (e.g., autoencoder, deep belief network, Hebbian learning, generative adversarial network, self-organizing map, convolutional neural network), expectation-maximization algorithm, method of moments, or a combination thereof.

A classifier may be configured to accept a plurality of input variables and to produce one or more output values based on the plurality of input variables. The plurality of input variables may comprise data indicative of a set of clusters of pixels, which may or may not correspond to events of interest such as LOBE binding events. For example, an input variable may comprise a set of one or more pixels corresponding to each of the sets of clusters of pixels. The pixels may be represented by, for example, an intensity value (e.g., selected from among a range of possible intensity values) representative of a detected or measured signal (e.g., an optical detection or measurement) at a given location. The input values may be calculated or extracted based on performing image analysis of the set of clusters of pixels, such as an indication of a size (e.g., diameter or perimeter), shape (e.g., circularity or symmetry), contrast, texture, or other physical attribute or image attribute of a cluster.

Input values for a classifier may comprise features that are extracted from an image using various image processing techniques and algorithms. For example, the features may comprise values derived from a convolution of the image with a kernel encoding the expected shape of one or more regions of interest such as a region where a LOBE event has occurred. As another example, the features may comprise values normalized to a calculated background signal in an image. For example, the background signal may be determined by fitting a distribution to the intensity in the non-patterned region of an array (e.g., where minimal LOBE binding is expected to be measured), and pixel intensities may be normalized to a number of counts above background (e.g., a number of standard deviations above background if a normal distribution is fitted). Such a feature may be useful because it "normalizes" the intensity values against values that may vary with experimental conditions, such as changes in exposure time (e.g., double the exposure time may result in double the intensity counts). As another example, the features may comprise aspects of the data acquisition protocol (e.g., components of the imaging system, an exposure time of the image acquisition, the wavelength at which the image was acquired, etc.). In some embodiments, separate classifiers are trained for each of a plurality of imaging systems.

A classifier may have one or more possible output values, each comprising one of a fixed number of possible values (e.g., a linear classifier, a logistic regression classifier, etc.) indicating a classification of the cluster as an event of interest (e.g., a LOBE event), a non-event of interest (e.g., a LOBE non-event), or an indeterminate event. The classifier may comprise a binary classifier, such that each of the one or more output values comprises one of two values (e.g., {0, 1}, {positive, negative}, or {event, non-event}, {present, absent}) indicating a classification of the cluster as an event of interest (e.g., a LOBE event) or a non-event of interest (e.g., a LOBE non-event). The classifier may be another type of classifier, such that each of the one or more output values comprises one of more than two values (e.g., {0, 1, 2}, {positive, negative, or indeterminate}, or {present, absent, or unknown}) indicating a classification of the cluster as an event of interest (e.g., a LOBE event), a non-event of interest (e.g., a LOBE non-event), or an indeterminate event. The output values may comprise descriptive labels, numerical values, or a combination thereof. Some of the output values may comprise descriptive labels. Such descriptive labels may provide an identification or indication of the cluster, and may comprise, for example, event, non-event, positive, negative, or indeterminate/unknown.

Some of the output values may comprise numerical values, such as binary, integer, or continuous values. Such binary output values may comprise, for example, {0, 1}. Such integer output values may comprise, for example, {0, 1, 2}. Such continuous output values may comprise, for example, a probability value of at least 0 and no more than 1 (e.g., of the classification of the cluster as an event of interest, such as a LOBE event, a non-event of interest, such as a LOBE non-event, or an indeterminate event). Such continuous output values may comprise, for example, an un-normalized probability value of at least 0. Such continuous output values may comprise, for example, an un-normalized probability value of at least 0. Such continuous output values may comprise, for example, an indication of a size (e.g., diameter or perimeter), shape (e.g., circularity), contrast, texture, or other physical attribute or image attribute of a cluster. Some numerical values may be mapped to descriptive labels, for example, by mapping 1 to "positive" and 0 to "negative." Output value need not be a numerical value. For example, the output value can be a binary outcome (e.g., yes/no), a categorical outcome (e.g., LOBE bound, non-specific binding event, no LOBE bound, or apparent sample defect), or a continuous outcome (e.g., size of array site). For discrete outputs, distributions can be determined for the characteristic being measured. Distributions can be modeled according to Poisson, binomial, beta-binomial, discrete Weibull, geometric, hypergeometric, or negative binomial behavior. Categorical data can be modeled, for example, by a categorical distribution (e.g., an assignment of probabilities to each class) or a multinomial distribution. A modeling outcomes can be a mixtures of distributions (e.g., a gaussian mixture which is a distribution composed of two or more gaussians), or a non-parametric distribution such as a normalized histogram, a kernel density estimate derived from a histogram, or a non-parametric discrete distribution converted into a continuous distribution by interpolation.

Some of the output values may be assigned based on one or more cutoff values. For example, a binary classification of clusters may assign an output value of "positive" or 1 if the sample indicates that the cluster has at least a 50% probability of being an actual event, such as a LOBE event. For example, a binary classification of samples may assign an output value of "negative" or 0 if the sample indicates that the cluster has less than a 50% probability of being an actual LOBE event (or equivalently, at least a 50% probability of being a LOBE non-event). In this case, a single cutoff value of 50% is used to classify clusters into one of the two possible binary output values. Examples of single cutoff values may include about 1%, 2%, 5%, 10%, 20%, 30%, 40%, 50%, 60%, 70%, 80%, 90%, 95%, 98%, or 99%.

As another example, a classification of clusters may assign an output value of "positive" or 1 if the cluster has a probability of being an actual event (e.g., a LOBE event) of at least about 50%, 60%, 70%, 80%, 90%, 95%, 98%, or 99%. The classification of clusters may assign an output value of "positive" or 1 if the sample indicates that the subject has a probability of producing an actual event (e.g., a LOBE event) of more than 50%, 60%, 70%, 80%, 90%, 95%, 98%, or 99% or more. The classification of clusters may assign an output value of "negative" or 0 if the cluster has a probability of being an actual event (e.g., a LOBE event) of less than 50%, 40%, 30%, 20%, 10%, 5%, 2%, 1% or less. The classification of clusters may assign an output value of "indeterminate" or 2 if the cluster has not been classified as "positive," "negative," 1, or 0. In this case, a set of two cutoff values can be used to classify clusters into one of the three possible output values (e.g., a first, smaller cutoff value and a second, larger cutoff value). Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify clusters into one of n+1 possible output values, where n is any positive integer.

A classifier may be trained with a plurality of independent training samples. Each of the independent training samples may include pixel information acquired from a single pixel, a cluster of pixels, a group of pixels that acquires signal from a site in an array, a collection of pixels (and/or pixel clusters) that acquires signals from multiple sites in an array, a collection of pixels (and/or pixel clusters) that acquire signals from a region of sites in an array, a collection of pixels (and/or pixel clusters) that acquire signals from a collection of spatially disparate sites in an array, or pixels (and/or pixel clusters) that acquire signals from an entire array. The data can include one or more known output values corresponding to the foregoing. Independent training samples may comprise the data and associated outputs obtained from a plurality of different images, experimental runs, experimental conditions, equipment, etc. Independent training samples may comprise data and associated outputs obtained at a plurality of different time points from the same sample. The data may have been acquired from the sample after treatment with different affinity agents or other differing conditions. Alternatively, independent training samples may comprise data and associated outputs obtained at a plurality of different time points from different samples. The data may have been acquired from the different samples after treatment with different affinity agents or other differing conditions. Independent training samples may be associated with presence of an event of interest such as a LOBE event (e.g., training samples comprising clusters of pixels and associated outputs obtained from imaging a plurality of known LOBE events). Independent training samples may be associated with absence of an event of interest, such as absence of a LOBE event (e.g., training samples comprising clusters of pixels and associated outputs obtained from imaging a plurality of known LOBE non-events).

A classifier may be trained with at least about 2, 100, 500, 1 thousand, 5 thousand, 10 thousand, 20 thousand, 30 thousand, 40 thousand, 50 thousand 100 thousand, 200 thousand, 300 thousand, 400 thousand, 500 thousand, 1 million, 2 million, 3 million, 4 million, 5 million, 10 million, 100 million, 1 billion or more independent training samples. The independent training samples may comprise samples associated with presence of events of interest, such as LOBE events, and/or samples associated with absence of an event of interest, such as LOBE non-events. Alternatively or additionally to the lower limits of the ranges set forth above, a classifier may be trained with no more than about 1 billion, 100 million, 10 million, 1 million, 800 thousand, 500 thousand, 250 thousand, 100 thousand, 50 thousand, 10 thousand, 1 thousand, 500, 250, 100, 50, or 2 independent training samples. The training samples may be associated with presence of an event of interest (e.g., LOBE events) or alternatively, the training samples may be associated with absence of events of interest (e.g., LOBE non-events). In some embodiments, the cluster of pixels being classified is independent of samples used to train the classifier.

A classifier may be trained with a first number of independent training samples associated with presence of one or more events of interest (e.g., LOBE events) and a second number of independent training samples associated with an absence of one or more events of interest (e.g., LOBE non-events). The first number of independent training samples associated with presence of one or more events of interest (e.g., LOBE events) may be no more than the second number of independent training samples associated with an absence of the one or more events of interest (e.g., LOBE events). The first number of independent training samples associated with presence of one or more events of interest (e.g., LOBE events) may be equal to the second number of independent training samples associated with an absence of the one or more events of interest (e.g., LOBE events). The first number of independent training samples associated with presence of one or more events of interest (e.g., LOBE events) may be greater than the second number of independent training samples associated with an absence of the one or more events of interest (e.g., LOBE events).

A classifier may be configured to detect or identify one or more events of interest and/or non-events of interest (e.g., LOBE events and/or LOBE non-events) with an accuracy of at least about 50%, 60%, 70%, 80%, 85%, 90%, 95%, 96%, 97%, 98%, 99%, or more; for at least about 50, 100, 200, 300, or more independent samples. The accuracy of detecting or identifying one or more events of interest (e.g., LOBE events) by the classifier may be calculated as the percentage of independent test samples (e.g., clusters that are LOBE events or LOBE non-events) that are correctly identified or classified as being an event of interest (e.g., a LOBE event) or a non-event of interest (e.g., a LOBE non-event), respectively.

A classifier may be configured to detect or identify one or more events of interest (e.g., LOBE events) with a positive predictive value (PPV) of at least about 5%, 10%, 20%, 30%, 40%, 50%, 60%, 70%, 80%, 90%, 95%, 96%, 97%, 98%, 99%, or more. The PPV of detecting or identifying one or more events of interest (e.g., LOBE events) by the classifier may be calculated as the percentage of clusters identified or classified as events of interest (e.g., LOBE events) that correspond to clusters that truly are events of interest (e.g., LOBE events). A PPV may also be referred to as a precision.

A classifier may be configured to detect or identify one or more non-events of interest (e.g., LOBE non-events) with a negative predictive value (NPV) of at least about 5%, 10%, 20%, 30%, 40%, 50%, 75%, 80%, 90%, 95%, 99%, or more. The NPV of detecting or identifying non-events of interest (e.g., LOBE non-events) by the classifier may be calculated as the percentage of clusters identified or classified as non-events of interest (e.g., not being LOBE events) that correspond to clusters that truly are non-events of interest (e.g., LOBE non-events).

A classifier may be configured to detect or identify events of interest (e.g., LOBE events) with a sensitivity of at least about 5%, 10%, 20%, 30%, 40%, 50%, 60%, 70%, 80%, 90%, 95%, 96%, 97%, 98%, 99%, or more. The sensitivity of detecting or identifying events of interest (e.g., LOBE events) by the classifier may be calculated as the percentage of independent test samples associated with presence of events of interest (e.g., LOBE events) that are correctly identified or classified as events of interest (e.g., LOBE events). A sensitivity may also be referred to as a recall.

A classifier may be configured to detect or identify non-events of interest (e.g., LOBE non-events) with a specificity of at least about 5%, 10%, 20%, 30%, 40%, 50%, 60%, 70%, 80%, 90%, 95%, 96%, 97%, 98%, 99%, or more. The specificity of detecting or identifying the non-events of interest (e.g., LOBE non-events) by the classifier may be calculated as the percentage of independent test samples associated with absence of events of interest (e.g., LOBE non-events) that are correctly identified or classified as not being events of interest (e.g., as being LOBE non-events).

A classifier may be adjusted or tuned to improve the performance, accuracy, PPV, NPV, sensitivity, specificity, or combination thereof, of detecting or identifying one or more events of interest (e.g., LOBE events), or one or more non-events of interest (e.g., LOBE non-events). The classifier may be adjusted or tuned by adjusting parameters of the classifier (e.g., a set of cutoff values used to classify a cluster of pixels as described elsewhere herein, or weights of a neural network). The classifier may be adjusted or tuned continuously during the training process or after the training process has completed. For example, re-training or continuous training can be carried out using data obtained from analytical measurements. For example, assays run on a system used by an end user, such as a researcher or clinician, can provide scientific or clinical output to the end user, and can also transmit training data to a computer that is configured to train the system.

After a classifier is initially trained, a subset of the inputs may be identified (for example, as most influential or most important) to be included for making high-quality classifications. For example, a subset of the set of input variables may be identified as most influential or most important to be included for making high-quality classifications or identifications of one or more events of interest (e.g., LOBE events) and/or non-events of interest (e.g., LOBE non-events). The set of input variables or a subset thereof may be ranked based on metrics indicative of each input variable's influence or importance toward making high-quality classifications or identifications of an event of interest (e.g., LOBE event) or non-event of interest (e.g., LOBE non-event). Such metrics may be used to reduce, in some cases significantly, the number of input variables (e.g., predictor variables) that may be used to train the classifier to a desired performance level (e.g., based on a desired minimum accuracy, PPV, NPV, sensitivity, specificity, or combination thereof). In some configurations, a set of inputs can be divided into a first subset of the inputs that is used to train a machine learning algorithm, a second set of the inputs can be used to validate the machine learning algorithm and a third set of the inputs can be used to test the machine learning algorithm. The inputs can be used, for example, to select underlying models for the machine learning algorithm or to tune hyperparameters within those models.

In some embodiments, a cluster of pixels being classified is independent of samples used to train a classifier. For example, the training datasets used to train a classifier may be distinct from the test datasets to which the classifier is applied. As another example, an expansive collection of training datasets may be used to train a base classifier, and that base classifier may be used as an initial starting point for analysis of any individual dataset. The base classifier may be further refined over time, based on acquisition parameters of the dataset or using an expectation maximization approach prior to application to that dataset.

For example, if training an algorithm with a plurality comprising several dozen or hundreds of input variables in the classifier results in an accuracy of classification of more than 99%, then training the training algorithm instead with a selected subset of no more than about 2, 3, 4, 5, 6, 7, 8, 9, 10, 20, 30, 40, 50, or 100 such most influential or most important input variables among the plurality may result in decreased but still acceptable accuracy of classification (e.g., at least about 70%, 80%, 90%, 95%, 96%, 97%, or 98%).

Optionally, a classifier can be calibrated to account for changes that occur (or that are expected to occur) over the course of use for an imaging system. For example, an analyte, or ensemble of analytes, that is present at a site of an array may demonstrate a loss of signal over the course of a series of detection steps. This may be the case, for example, due to photobleaching by excitation sources used for luminescence detection, or due to chemical degradation after long term exposure, or repeated exposure, to particular solvents, reagents or conditions. Alternatively, signal gain may occur due to accumulation of signal producing contaminants in the observation field of an imaging device. For example, contaminants may accumulate at a site of an array causing an increase in apparent signal produced by the site. As an alternative or addition to employing calibration of a classifier, the subject to be observed by an imaging system can be refreshed, for example, by replacing a degraded analyte, supplementing with additional analyte, or removal of contaminants. By way of more specific example, an array of labeled SNAPs and/or analytes can be imaged multiple times over the course of a method set forth herein and then the labeled SNAPs and/or analytes can be replaced for subsequent imaging steps. A different classifier can be applied to images before and after the refresh as appropriate to the changes or trends known or suspected to occur before and after the refresh.

The pixel information of image data may be stored in a binary format, optionally along with metadata. The metadata may include pertinent information about the measurement conditions for each image, such as the instrument (e.g., identified via serial number) from which data was acquired, the flow cell or other vessel (e.g., identified via bar code) that was detected by the instrument, the identity of one or more reagent lots used during detection, a timestamp (e.g., date or time) when pixel information was acquired, the chip coordinates, the experiment or run (e.g., globally unique identifier (GUID) or universally unique identifier (UUID) number), and other pertinent information such as the software version, under which the image data was acquired. Alternatively to a binary signal, the signal may store two pieces of information per landing site: a binary value indicative of a binding event or non-event, and another binary value indicative of whether the signal is determinate (ON or OFF) or indeterminate (unknown). The intensity value of each pixel may be retained for downstream analyses. Alternatively, the intensity value of each pixel may be discarded and not retained for downstream analyses. In some embodiments, a degree of confidence (10%, etc.) of each class being correct is stored along with the binarized data. The degree of confidence may account for spatial and/or temporal effects and/or variations of confidence as part of experimental flow.

Image analysis may be tuned as needed based on the decoding approaches used, as described elsewhere herein. For example, for a given application, it may be less desirable to have a false positive result of identifying an event of interest (e.g., binding of a LOBE) than a false negative; therefore, the threshold may be tuned or adjusted accordingly. In some embodiments, type 1 (e.g., false positives) and type 2 errors (e.g., false negatives) may not be treated equally, and each may be weighted differently to account for such unequal treatment. In some embodiments, the type 1 and 2 errors may be treated equally, and each may be weighted equally to account for such equal treatment. The threshold can be set at or near the center of a probability range (i.e., a setting of 0.5 in a range of 0 to 1). However the threshold can be a probability cutoff that is lower than 0.5 or higher than 0.5 to reduce the likelihood of false positive results or false negative results.

In some embodiments, event detection (e.g., LOBE finding) may comprise performing an image segmentation (e.g., to solve an image segmentation problem). For example, a goal of an image segmentation problem may be to detect patterns in an image and to "segment" the image into sections corresponding to each pattern. The image segmentation may be performed using various suitable unsupervised clustering approaches and/or various suitable image segmentation algorithms (e.g., using random Markov fields).

In some embodiments, images may be subjected to processing (e.g., using various suitable image processing algorithms) to remove or "censor" image artifacts. For example, image artifacts may comprise substantial areas of pixels with saturated intensity values (e.g., at a 100% intensity value or a 0% intensity value). These may appear in the image as, for example, large bright "bubbles", which may overlap with (e.g., obscure) multiple landing sites. Therefore, image processing algorithms may be applied to detect and remove such artifacts from analysis in event detection (e.g., LOBE detection); this may include "censoring" or excluding the associated landing sites from the downstream decoding analysis. In another example, landing sites for which position cannot be determined confidently can be censored and treated as artifacts. As another example, a trained classifier configured to perform event detection (e.g., LOBE detection) may comprise classes for detection, identification, or classification of artifacts which may be expected to be observed in images.

Upon completion of operations for locating sites or regions of interest in an image (e.g., SNAP gridding) and for detecting events of interest (e.g., LOBE finding), the two output sets may be combined to determine the nearest site (e.g., landing site) where an analyte of interest (e.g., a protein of interest) may be found, given a detected event (e.g., a LOBE event). This approach can be particularly useful in a censored decoding approach in which non-binding events are not considered to be informative. Alternatively, non-binding events can be included in the output sets and used to determine the nearest site for a feature on a substrate (e.g., a feature such as a site in an array). If such a nearest site (e.g., landing site) is in close enough proximity to a region of interest in an image, the event (e.g., LOBE binding) may be considered to have occurred at the site (e.g., the LOBE bound to a protein or peptide at the site) or to not have occurred as the case may be. Conversely, if such a nearest site (e.g., landing site) is not in close enough proximity to a region of interest (e.g., is too far away) in an image, the event (e.g., LOBE binding) may be considered to not have occurred at the site (e.g., a non-specific binding event has occurred for the LOBE). Brighter LOBEs, although generally easier to detect, may produce greater positional uncertainty, for example, due to signal cross-talk with pixels that detect an adjacent LOBE. This can be exacerbated when adjacent LOBEs are both relatively bright, resulting in cross talk with each other to yield apparent overlap or merging of sites in an image.

A simple threshold of distance may be applied to determine whether or not a close proximity condition is satisfied. Alternatively or additionally, probability distributions and/or confidence levels may be analyzed to determine whether or not the close proximity condition is satisfied. The threshold may be set by performing control experiments based on a known input, to acquire image data indicating binding event locations, which allows distance calibration based on the physical layout and setup of the measurement conditions. As another example, the distance threshold for localizing a LOBE to a landing site may take into account quality metrics from a SNAP gridding algorithm (e.g., how confident the gridding algorithm is of the localization at each location), the resolution of the image sensor, and the signal-to-noise (SNR) ratio of features used to localize the landing site and/or LOBE. For example, a bright LOBE may have a higher likelihood of being accurately characterized than a dim LOBE. A distance threshold can optionally be set based on the amount of distortion present in various points or regions in a field of view. For example, distortions can be used as points of reference for determining relative distances between sites or features in the field of view. In another example, distances can be adjusted to account for distortions that may otherwise introduce errors in in distance determinations. A distance threshold can optionally be set based on noise or censored artifacts in an image. A distance threshold can be in the form of a value or a function when used for determining the proximity of sites or features in an image.

For each site (e.g., site attached to a protein or other entity) in a given image, an event of interest (e.g., a binding event) or non-event of interest can be determined. Therefore, a per-image map can be produced, which provides a binary signal of whether an entity (e.g., protein) is present at a given location. However, a binary signal need not necessarily be used. For example, the presence or absence of an entity at a given location can be represented by a value in a continuous range of values, by a probability value, or by categorical data. A suitable decoding algorithm, as described elsewhere herein, may be performed on the per-image binding map to identify entities (e.g., proteins) in a sample and/or quantities of entities in the sample. In some configurations, images from adjacent regions of an array can be stitched together or otherwise registered with respect to each other. The combined image can be mapped, decoded or processed as set forth herein. Conversely, an image can be subdivided into image regions, and the resulting subregions can be mapped, decoded or processed as set forth herein.

In some embodiments, a system of the present disclosure may comprise commercially available or custom hardware configured to perform image processing (e.g., GPU offloads or FPGAs to perform custom operations). Some or all of the instrument control and/or image processing methods set forth herein can be performed remote from the instrument being used. For example, the methods can be performed on a dedicated co-processor, such as CPUs within a computer, GPUs, FPGAs, real-time microcontrollers, separate computer, or cloud instance. In some configurations, one or more of the hardware components that performs all or part of an instrument control and/or image processing method can be a component part that is physically associated with the instrument.

In some embodiments, a decoding algorithm may be selected and performed using one or more computers (e.g., either locally or on the cloud). The one or more computers may be configured to enable horizontal scalability, such that the decoding algorithm can be parallelized by being split up across a plurality of independent processors for independent computational processing. For example, the decoding algorithm may be parallelized based on analyzing each protein site among a plurality of protein sites independently. Therefore, the location on a chip may be treated as a trivial scaling dimension. Optionally, the location on a chip may be treated as a set of scaling dimensions which allow for maximal or complete independence of the data being processed. In some embodiments, data to be processed may be re-dimensionalized (e.g., by slicing and inverting the data before processing it using the decoding algorithm). The re-dimensionalizing of the data may be performed in some cases, for example, when the temporal order of data acquisition does not represent the same dimension as one of the scaling dimensions.

In some embodiments, data from single-molecule binding measurements of arrays may be used to refine a binding model (e.g., an aptamer-protein binding model), thereby providing an improved predictor of an affinity agent binding model. In some embodiments, machine learning algorithms are applied to refine the decoding algorithms, as appropriate. Exemplary decoding algorithms that can be used are set forth herein and in US Pat. App. Pub. Nos. 2020/0082914 A1 or 2020/0286584 A1, each of which is incorporated herein by reference. Moreover, the image analysis algorithms and decoding algorithms set forth herein can be trained together. In particular embodiments, image data derived from image analysis algorithms can be used to train a decoding algorithm, or the image analysis data can be used for identifying a protein or other object using a decoding algorithm. Alternatively or additionally, data derived from a decoding algorithm, such as the identity of a protein or other object, can be used to train an image analysis algorithm or to refine the quality of image data derived from an image analysis algorithm.

In some embodiments, a small number of reagents (e.g., about 10-20) may be used, and then a simplified decoding approach may be used. For example, rather than performing a full decoding approach to decode every protein site in an array, the simplified decoding approach may comprise enumerating a set of all possible combinations of passes, and limiting the decoding to only that set of all possible combinations of passes. Therefore, a small set (e.g., about 256) of possible outcomes is decoded to identify the entity at every site. For example, such a small set of possible outcomes may be decoded using a simplified approach, such as use of a hashing function to a given combination of binding outcomes and a lookup table to decode the entity based on the output of the hashing function. In some embodiments, the simplified decoding algorithm comprises the use of pre-computed or cached values (e.g., whereby most likely outcomes are cached for fast retrieval and lookup). Such a simplified decoding approach may be applied to decoding approaches with up to hundreds of affinity agents (e.g., probes). For example, the manner in which batches of probes affect the final probabilities may be pre-computed, and then probabilistic adjustments may be performed every n iterations, (i.e., n being an integer greater than 1) rather than every 1 iteration. As another example, batches of results may be pre-computed, and iterations may be performed accordingly (e.g., pre-compute a first batch of ten results, calculate the resulting probabilities; then repeat for the second and subsequent batches of ten results).

Computer Systems

Figure 2:
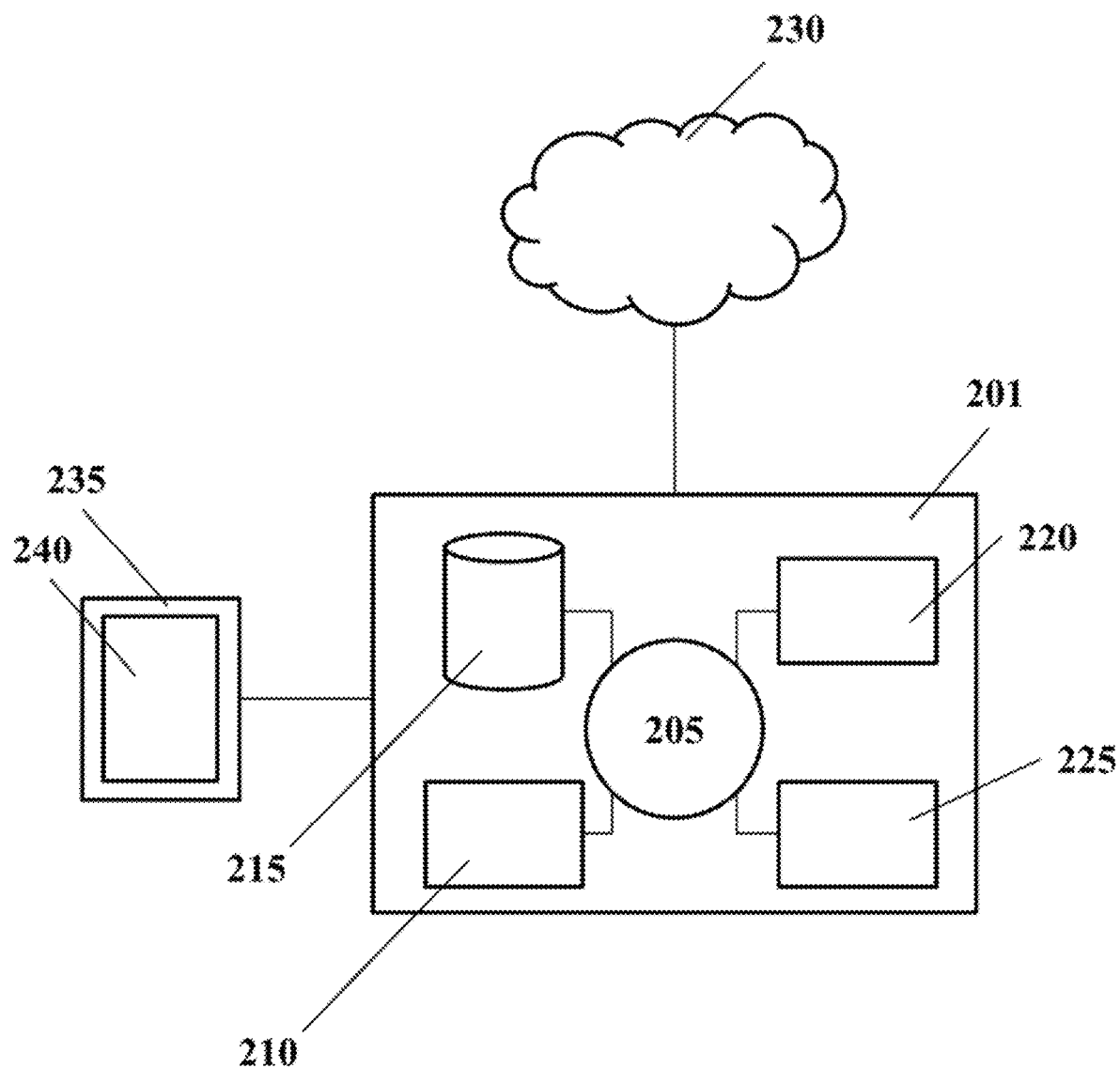
FIG. 2 illustrates a computer system that is programmed or otherwise configured to implement methods provided herein.

The present disclosure provides computer systems that are programmed to implement methods of the disclosure. FIG. 2 shows a computer system 201 that is programmed or otherwise configured to, for example, use one or more light sensing devices, acquiring pixel information from sites in an array, wherein the sites comprise biological, chemical, or physical entities that produce light; process the pixel information to identify a set of regions of interest (ROIs) corresponding to the sites in the array that produce the light; classify the pixel information for the ROIs into a categorical classification from among a plurality of distinct categorical classifications, thereby producing a plurality of pixel classifications; and identify one or more components of the array of biological, chemical, or physical entities based at least in part on the plurality of pixel classifications. The computer system 201 can regulate various aspects of analysis, calculation, and generation of the present disclosure, such as, for example, using one or more light sensing devices, acquiring pixel information from sites in an array, wherein the sites comprise biological, chemical, or physical entities that produce light; processing the pixel information to identify a set of regions of interest (ROIs) corresponding to the sites in the array that produce the light; classifying the pixel information for the ROIs into a categorical classification from among a plurality of distinct categorical classifications, thereby producing a plurality of pixel classifications; and identifying one or more components of the array of biological, chemical, or physical entities based at least in part on the plurality of pixel classifications. The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some embodiments, is a telecommunication and/or data network. The network 230 can include one or more computer servers, which can enable distributed computing, such as cloud computing. For example, one or more computer servers may enable cloud computing over the network 230 ("the cloud") to perform various aspects of analysis, calculation, and generation of the present disclosure, such as, for example, acquiring pixel information of an array of biological, chemical, or physical entities; and detecting components of the array of biological, chemical, or physical entities based at least in part on the acquired pixel information. Such cloud computing may be provided by cloud computing platforms such as, for example, Amazon Web Services (AWS), Microsoft Azure, Google Cloud Platform, and IBM cloud. The network 230, in some embodiments, with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some embodiments, the circuit is an application specific integrated circuit (ASIC).

The storage unit 215 can store files, such as drivers, libraries and saved programs. The storage unit 215 can store user data, e.g., user preferences and user programs. The computer system 201 in some embodiments, can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., a physician, a nurse, a caretaker, a patient, or a subject). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine-executable or machine-readable code can be provided in the form of software. During use, the code can be executed by the processor 205. In some embodiments, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a processor for execution.

The computer system 201 can include or be in communication with an electronic display 235 that comprises a user interface (UI) 240 for providing, for example, video, image, or pixel information of an array of biological, chemical, or physical entities, and detected biological, chemical, or physical entities. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, use one or more light sensing devices, acquiring pixel information from sites in an array, wherein the sites comprise biological, chemical, or physical entities that produce light; process the pixel information to identify a set of regions of interest (ROIs) corresponding to the sites in the array that produce the light; classify the pixel information for the ROIs into a categorical classification from among a plurality of distinct categorical classifications, thereby producing a plurality of pixel classifications; and identify one or more components of the array of biological, chemical, or physical entities based at least in part on the plurality of pixel classifications.

The present disclosure provides a non-transitory information-recording medium that has, encoded thereon, instructions for the execution of one or more steps of the methods set forth herein, for example, when these instructions are executed by an electronic computer in a non-abstract manner. This disclosure further provides a computer processor (i.e., not a human mind) configured to implement, in a non-abstract manner, one or more of the methods set forth herein. All methods, compositions, devices and systems set forth herein will be understood to be implementable in physical, tangible and non-abstract form. The claims are intended to encompass physical, tangible and non-abstract subject matter. Explicit limitation of any claim to physical, tangible and non-abstract subject matter will be understood to limit the claim to cover only non-abstract subject matter, when taken as a whole. As used herein, the term "non-abstract" is the converse of "abstract" as that term has been interpreted by controlling precedent of the U.S. Supreme Court and the Federal Circuit as of the priority date of this application.

Example I

SNAP Gridding

This example describes a method for SNAP gridding. The method is particularly useful for registering sites in narrow-aperture images. An advantage of this method is that it does not require use of template images that are acquired at a magnification level that differs from the image of interest. Accordingly, the methods described in this example do not require magnification adjustment between a template image and image of interest.

Figure 3:
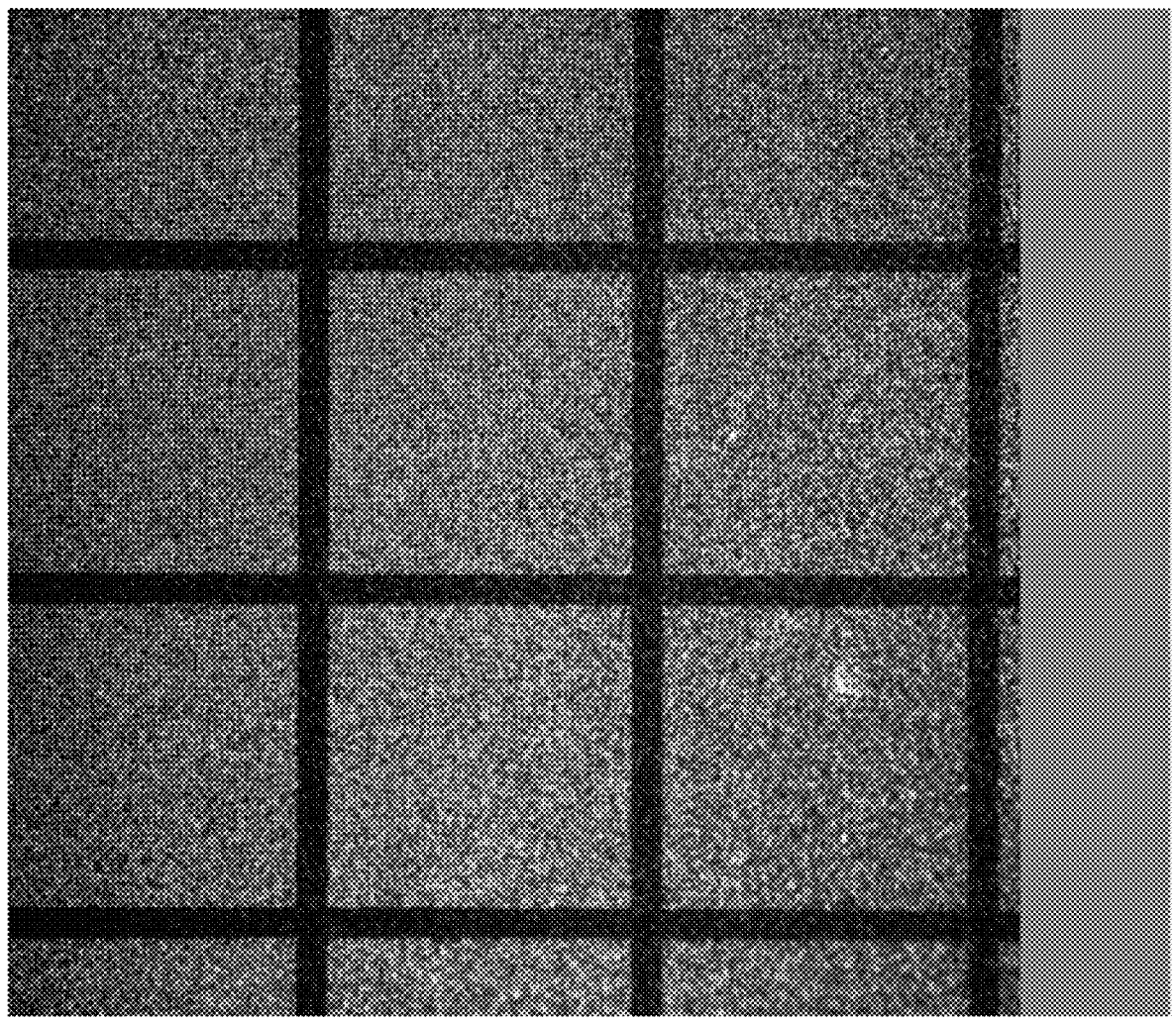
FIG. 3 shows an image of fluorescence signals obtained from an array of fluorescently labeled SNAPs.

A fluorescent image was obtained from an array of fluorescently labeled SNAPs. The distance between SNAP sites (i.e., the "site pitch") was 1.625 microns, which was approximately equal to 5 pixels in acquired images. The sites were roughly circular and the average radius for the sites was 1.5 to 2.0 pixels. The field of view was 2048×2048 pixels, which was roughly equivalent to about 665 microns by 665 microns (i.e., magnification was about 5 pixels=1.625 microns). As shown in the exemplary image of FIG. 3, the image includes several subarrays, each subarray having N×N SNAP sites (i.e., white spots) arranged in a square and separated by neighboring subarrays by 'streets' (i.e., dark regions).

The image was prepared by correcting distortions and rotational skew, thereby producing an input image for SNAP gridding.

An artifact mask image was obtained using an algorithm to search SNAP array images for features having unusual size or shape. The artifact mask was used to exclude artifacts from the SNAP gridding computation to increase robustness.

Figure 4:
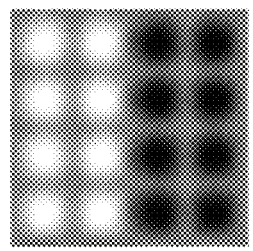
FIG. 4 shows an edge kernel representing an ideal image of SNAP sites at the edge of an array where it meets a street.
Figure 5:
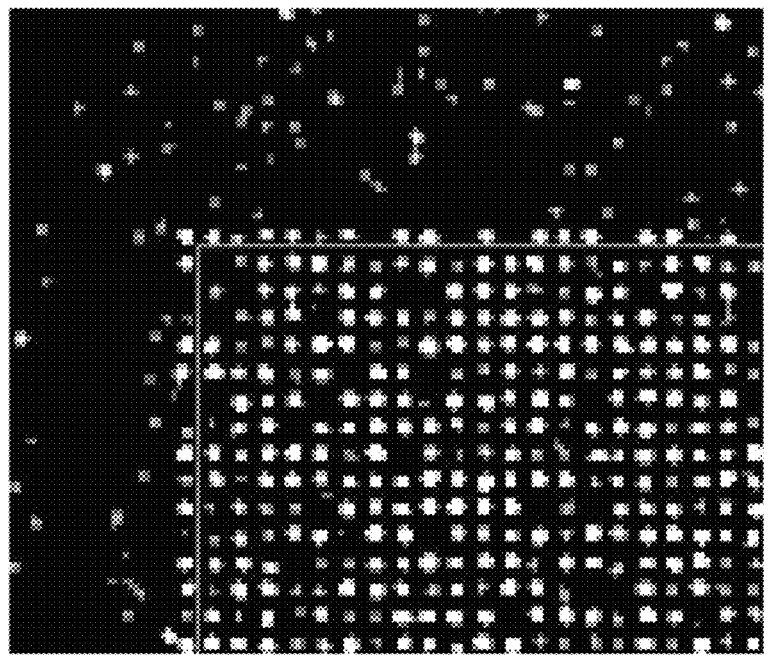
FIG. 5 shows a rough SNAP grid (dark lines) overlaid on an image of fluorescence signals obtained from an array of fluorescently labeled SNAPs.

The input image was processed in two directions (e.g., horizontal and vertical), independently as follows. An edge-detection kernel was defined for the first direction of the input image. A 4×4 grid of pads, half ON and half OFF was selected for this purpose and is shown in FIG. 4. The input image was convolved with the edge-detection kernel. For this step the artifact mask was applied such that artifact object pixels were set to 0 before the convolution, thus preventing bright artifacts from contributing to peaks in the convolution output. The image was profiled (i.e., summed along rows or columns) such that the detected edges across the image accumulated together creating a signal peak at each edge. The resulting 1-D (one-dimensional) array of sums was convolved with a kernel that had peaks separated by the distance that is expected between subarray edges (i.e., the width of the streets separating subarrays), since magnification and layout were known a priori. A signal peak was found in the result of that convolution, the signal peak corresponding to the location where the kernel best matches the image profile. This process was then repeated for a second direction of the image, the second direction being orthogonal to the first direction processed. As shown in the image of FIG. 5, the combined results for the two directions specified a location of a rough SNAP grid (shown as orthogonal straight lines) with respect to the sites (each site having a detected SNAP shown as a cluster of white pixels).

The rough SNAP grid was used as an input to a refinement process. The refinement step was carried out to improve the accuracy of the specified locations to sub-pixel resolution. The refinement step was carried out as follows. Given the rough SNAP grid location, the implied locations for sites in the SNAP grid were computed. An enhanced image was computed by convolving the input image with a standard 'site kernel'. More specifically, SNAP features in the input image were sharpened by convolving with a small, localized kernel which exemplifies an ideal SNAP signal. A 5×5 Gaussian point spread function was used to convolve the features with the kernel.

Figure 6:
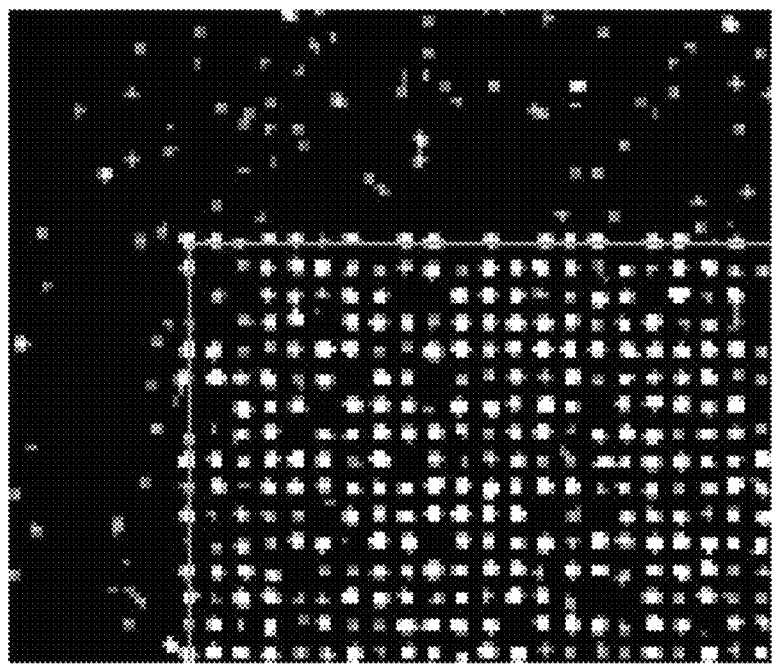
FIG. 6 shows a refined SNAP grid (dark lines) overlaid on an image of fluorescence signals obtained from an array of fluorescently labeled SNAPs.

The enhanced image facilitated a simple centroid calculation to more accurately find the "peak" in each site cell as indicated by the image in FIG. 6. The signal centroids were computed within each implied site cell on the enhanced image.

For each of two orthogonal directions (e.g., horizontal and vertical), the consensus of the horizontal and vertical deltas between theoretical site centers and found object centroids was computed. For this example, the mean of the horizontal and vertical deltas between theoretical site centers and found object centroids was used as the consensus. The resulting consensus horizontal and vertical shifts transformed the rough SNAP grid location into a final, refined SNAP grid location.

Example II

Iterative SNAP Gridding

This example describes an iterative method for SNAP gridding. The method was applied to images that were acquired, undistorted, de-rotated, pad-kernel-convolved, and artifact-masked as set forth in Example I. Iteration was then carried out as set forth in further detail below, the iterations occurring until reaching a threshold on the amount of magnification change. If the found magnification change was less than or equal to a preset threshold then iteration stopped, otherwise it continued. The magnification is expressed in pad pitch pixels, and is the same scale as the 5.0 pixel pitch for SNAP sites in acquired images. The default value for the threshold was set at 0.0001 pixel.

For each iteration the algorithm started with an input SNAP grid location (SGL), which is a combination of magnification (expressed as SNAP site pitch in pixels) and X,Y location in the image of the top left corner of the first full subarray of SNAP sites. The algorithm computed a refined estimate of the offset and magnification thus producing an updated SGL.

Figure 7A:
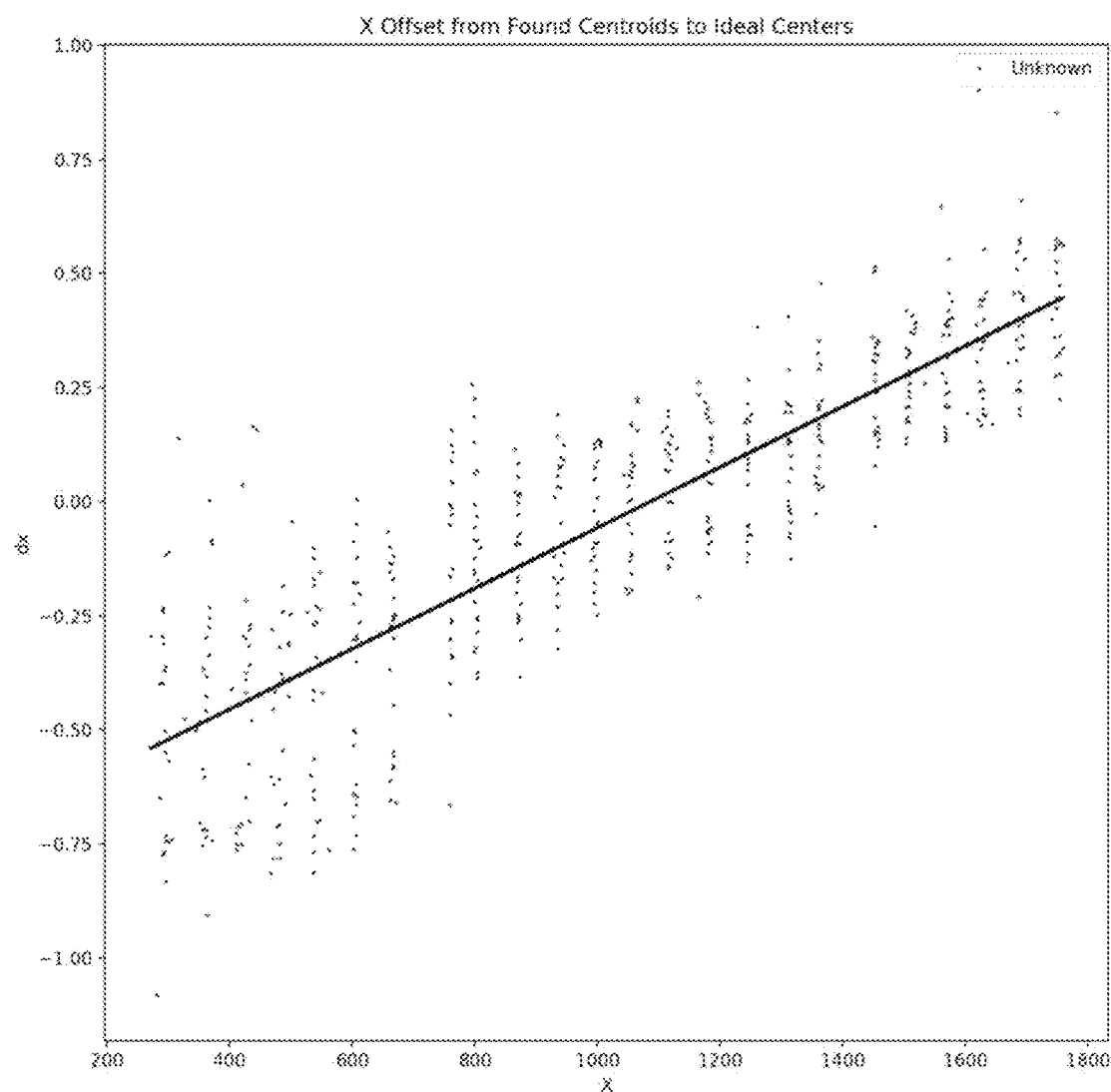
FIG. 7A shows a plot of the X offset from found centroids to ideal centers as output from a SNAP gridding algorithm.
Figure 7B:
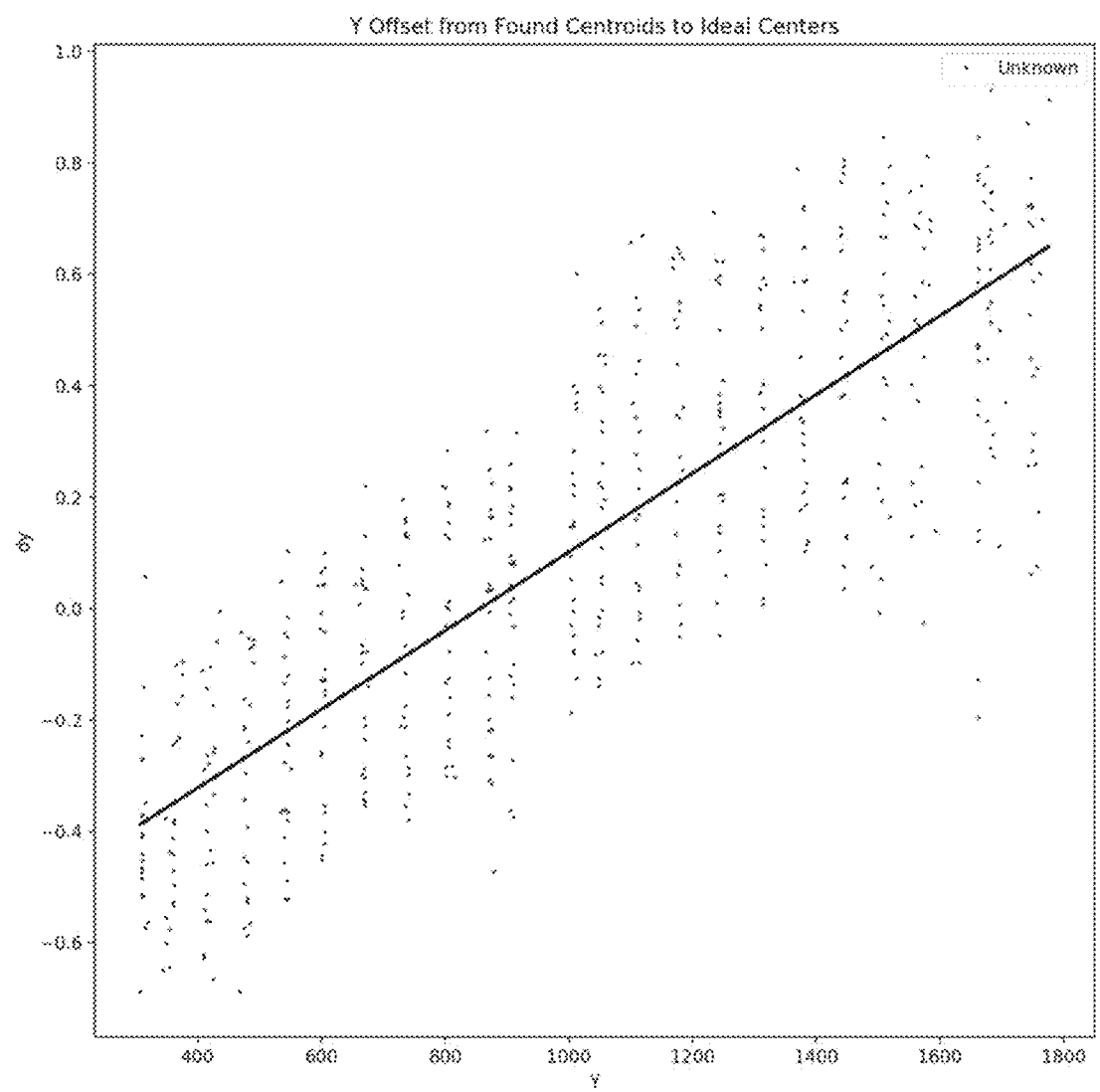
FIG. 7B shows a plot of the Y offset from found centroids to ideal centers as output from a SNAP gridding algorithm.

The following steps were performed to compute the updated SGL offset and magnification:

1. The expected pad locations ("spots") were computed and iterated based on the input SGL.
2. For each expected spot:
    a. Extract a 5×5 pixel region of interest via sub-pixel resampling, using bilinear resampling. (Resampling is optional and is performed to account for the computed expected spot locations being floating point numbers, not integral, whilst pixel locations in images are integral.)
    b. Compute the centroid of the 5×5 extracted sub-image and keep the difference (vector) between the centroid and the center of the image as the "centroid offset".
    c. Keep the highest pixel value as the "peak value" of the spot.
3. Noise was reduced in the data by omitting weak spots. Spots having peak value less than the mean peak value of all spots are omitted (i.e., the bottom half of the data is omitted). Other thresholds for omitting spots can be applied to suit a particular application or detection system.
4. A "tiled median" was performed for the remaining spots as follows:
    a. "Tiles" were defined to be 64×64 square sub-regions of the input 2048×2048 image. (All tiles, not just a subset, so 32×32=1024 tiles.)
    b. Tiles near edges of the image were excluded because edges tend to be less reliable. For example excluding a 256-wide border around the edges of the image was found to be useful.
    c. The spots were bucketed into tiles, and for each tile the median centroid offset of those spots was computed, thus filtering out noise and treating spatially separated spots separately.
    d. A representative location for the tile was computed as the median of the X and Y values of the spots it comprised.
5. Separately for X and Y axes, the tiled median centroid offsets computed above were least-squares fit, thus producing a line whose slope is the estimated magnification difference vs the original input SGL magnification. Alternatively this step can use weighted least squares based on the number of spots per tile (e.g., the number of spots that survive the above filter) or based on the sum of pixel values of the spots. A plot of the X offset from found centroids to ideal centers is shown in FIG. 7A and a plot of the Y offset from found centroids to ideal centers is shown in FIG. 7B.
6. An updated/refined magnification was computed as the mean of the computed X and Y axes magnifications.
7. An updated/refined X,Y location of the SGL was computed as the input location plus the vector offset per the fitted lines. The vector offset per each fitted line is the value at the center (pixel value 1024) of the line.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting an array of biological, chemical, or physical entities, comprising:
   (a) using a set of light sensing devices, acquiring a first set of pixel information from sites in an array, and (ii) acquiring a second set of pixel information from the sites in the array, wherein the sites comprise biological, chemical, or physical entities that produce light;
   (b) processing the pixel information to (i) register the first set of pixel information and the second set of pixel information to a common coordinate system, and (ii) identify a set of regions of interest (ROIs) corresponding to the sites in the array that produce the light in the first set of pixel information and the second set of pixel information;
   (c) classifying the pixel information for the set of ROIs into a categorical classification from among a plurality of distinct categorical classifications, thereby producing a plurality of pixel classifications; and
   (d) identifying a component of the array of biological, chemical, or physical entities based at least in part on the plurality of pixel classifications.

2. The method of claim 1, wherein individual sites of the array comprise a biological, chemical, or physical entity selected from the group consisting of: (i) a structured nucleic acid particle; (ii) a structured nucleic acid particle comprising a fluorescent label; (iii) a protein; (iv) a protein attached to a structured nucleic acid particle; (v) an affinity agent bound to a protein; and (vi) an affinity agent bound to a protein, wherein the protein is attached to a structured nucleic acid particle.

3. The method of claim 1, wherein individual sites of the array each comprise a single biological, chemical, or physical entity that produces the light.

4. The method of claim 3, wherein the single biological, chemical, or physical entity is selected from the group consisting of (i) a single structured nucleic acid particle; (ii) a single structured nucleic acid particle comprising a fluorescent label; (iii) a single-protein; (iv) a single-protein attached to a single structured nucleic acid particle; (v) an affinity agent bound to a single-protein; and (vi) an affinity agent bound to a single-protein, wherein the single-protein is attached to a single structured nucleic acid particle.

5. The method of claim 1, wherein the set of light sensing devices is configured to use four-beam interference to create a two-dimensional sine wave pattern.

6. The method of claim 1, wherein the set of light sensing devices comprises a material compatible with complementary metal-oxide semiconductor (CMOS) processing, and wherein the set of light sensing devices is configured to be functionalized.

7. The method of claim 1, wherein the set of light sensing devices comprises an array of light sensing devices, wherein a pitch of individual devices in the array of light sensing devices is matched to a pitch of sites in the array of biological, chemical, or physical entities.

8. The method of claim 1, wherein each ROI of the set of ROIs comprises pixel information corresponding to a single cluster of pixels.

9. The method of claim 8, wherein (d) further comprises applying a classifier to the set of ROIs to classify each of the pixel information into the categorical classification.

10. The method of claim 9, wherein the classifier comprises a trained machine learning classifier.

11. The method of claim 10, wherein the trained machine learning classifier comprises a supervised machine learning algorithm.

12. The method of claim 11, wherein the supervised machine learning algorithm comprises a support vector machine (SVM), a linear regression, a logistic regression, a nonlinear regression, a neural network, a Random Forest, a deep learning algorithm, a naïve Bayes classifier, or a combination thereof.

13. The method of claim 10, wherein the trained machine learning classifier comprises an unsupervised machine learning algorithm.

14. The method of claim 13, wherein the unsupervised machine learning algorithm comprises clustering analysis, principal component analysis, independent component analysis, non-negative matrix factorization, singular value decomposition, anomaly detection, neural network, expectation-maximization algorithm, method of moments, or a combination thereof.

15. The method of claim 1, wherein the plurality of distinct categorical classifications comprises a first categorical classification associated with a light signal from a site in the array indicative of a presence of a biological, chemical, or physical entity, and a second categorical classification associated with an absence of a light signal from the array indicative of an absence of a biological, chemical, or physical entity.

16. The method of claim 15, wherein the first categorical classification is indicative of presence of light produced from an affinity agent bound to a structured nucleic acid particle-protein complex.

17. The method of claim 15, wherein the second categorical classification is indicative of an absence of an affinity agent bound to a structured nucleic acid particle-protein complex.

18. The method of claim 1, wherein the common coordinate system is determined by deconvolving the first set of pixel information with an edge kernel, the edge kernel representing a signal from a set of sites at an edge of the array.

19. The method of claim 18, wherein the common coordinate system is determined by deconvolving the first set of pixel information with a site kernel, the site kernel representing a signal from a single site in the array.

20. The method of claim 1, wherein the individual sites of the array each comprise a biological entity.

21. The method of claim 20, wherein the biological entity comprises a protein.

22. The method of claim 20, wherein the biological entity comprise a protein attached to a structured nucleic acid particle.

23. The method of claim 20, wherein the biological entity comprises an affinity agent bound to a protein, wherein the protein is attached to a structured nucleic acid particle.

24. The method of claim 1, wherein the sites are arranged in a repeating pattern in the array.

25. The method of claim 1, wherein the first set of pixel information is acquired from a first detection channel and the second set of pixel information is acquired from a second detection channel, wherein the first detection channel differs from the second detection channel.

26. The method of claim 1, wherein the first set of pixel information and the second set of pixel information comprise different patterns of sites in the array that produce the light.

* * * * *